US009884813B1

(12) United States Patent
Martinez et al.

(10) Patent No.: US 9,884,813 B1
(45) Date of Patent: Feb. 6, 2018

(54) PHARMACEUTICALLY ACCEPTABLE SALTS OF B-GUANIDINOPROPIONIC ACID WITH IMPROVED PROPERTIES AND USES THEREOF

(71) Applicant: Rgenix, Inc., New York, NY (US)

(72) Inventors: Eduardo J. Martinez, Bryn Mawr, PA (US); Andreas G. Grill, Saint James, NY (US); Aniruddh Singh, Carteret, NJ (US); Padmini Kavuru, Fitchburg, MA (US); Nicholas D. Paschalides, Marlborough, MA (US); Stephen A. Wald, Valley Cottage, NY (US)

(73) Assignee: Rgenix, Inc., New York, NY (US)

( * ) Notice: Subject to any disclaimer, the term of this patent is extended or adjusted under 35 U.S.C. 154(b) by 0 days.

(21) Appl. No.: 15/449,428

(22) Filed: Mar. 3, 2017

Related U.S. Application Data

(63) Continuation of application No. PCT/US2017/020266, filed on Mar. 1, 2017.

(51) Int. Cl.
| | |
|---|---|
| *A61K 31/4439* | (2006.01) |
| *C07C 279/14* | (2006.01) |
| *C07C 57/15* | (2006.01) |
| *A61K 9/00* | (2006.01) |
| *A61K 31/155* | (2006.01) |
| *A61K 31/194* | (2006.01) |

(52) U.S. Cl.
CPC .......... *C07C 279/14* (2013.01); *A61K 9/0019* (2013.01); *A61K 31/155* (2013.01); *A61K 31/194* (2013.01); *C07C 57/15* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 3,870,709 A | 3/1975 | Hamanaka | |
| 3,933,797 A | 1/1976 | Hamanaka | |
| (Continued) | | | |

FOREIGN PATENT DOCUMENTS

| | | | |
|---|---|---|---|
| CA | 1016538 A | 8/1977 | |
| CA | 2202265 A1 | 5/1996 | |
| (Continued) | | | |

OTHER PUBLICATIONS

International Search Report and Written Opinion for International Application No. PCT/US17/20266, dated May 22, 2017 (13 pages).

*Primary Examiner* — Karl J Puttlitz
(74) *Attorney, Agent, or Firm* — Clark & Elbing LLP; Kristina Bieker-Brady

(57) ABSTRACT

The present invention relates to new pharmaceutical salts of β-GPA which exhibit improved physical properties. In particular, the invention relates to salts of β-GPA with improved flow properties (e.g., improved Carr's index and/or Hausner ratio) such as fumarate salts, succinate salts, and oxalate salts. The invention also relates to pharmaceutical compositions including a pharmaceutically effective amount of one or more salts of β-GPA, as well as methods of treating cancer including administration of a formulation including a β-GPA salt of the invention to a subject in need thereof.

28 Claims, 28 Drawing Sheets

(56) References Cited

U.S. PATENT DOCUMENTS

| | | |
|---|---|---|
| 3,972,872 A | 8/1976 | Hamanaka |
| 5,750,193 A | 5/1998 | Nass et al. |
| 5,955,617 A | 9/1999 | Larsen et al. |
| 5,994,577 A | 11/1999 | Larsen et al. |
| 6,166,080 A | 12/2000 | Larsen et al. |
| 6,177,453 B1 | 1/2001 | Larsen et al. |
| 6,184,216 B1 | 2/2001 | Larsen et al. |
| 6,242,491 B1 | 6/2001 | Kaddurah-Daouk |
| 6,274,580 B1 | 8/2001 | Larsen et al. |
| 6,329,403 B1 | 12/2001 | Odaka et al. |
| 6,329,545 B1 | 12/2001 | Larsen et al. |
| 6,348,200 B1 | 2/2002 | Nakajima et al. |
| 6,605,115 B1 | 8/2003 | Cooke et al. |
| 7,186,754 B2 | 3/2007 | Kaddurah-Daouk |
| 7,273,846 B2 | 9/2007 | Bednarek |
| 8,101,661 B2 | 1/2012 | Mickle |
| 8,118,884 B2 | 2/2012 | Ascione et al. |
| 8,685,916 B2 | 4/2014 | Jenkins et al. |
| 8,748,567 B2 | 6/2014 | Narasimhaswamy et al. |
| 8,765,115 B2 | 7/2014 | Fujiwara et al. |
| 8,927,500 B2 | 1/2015 | Guerlavais et al. |
| 8,937,090 B2 | 1/2015 | Kaminuma et al. |
| 2002/0049253 A1 | 4/2002 | Kaddurah-Daouk |
| 2002/0082448 A1 | 6/2002 | Larsen et al. |
| 2002/0086885 A1 | 7/2002 | Odaka et al. |
| 2004/0074504 A1 | 4/2004 | Cooke et al. |
| 2004/0126366 A1 | 7/2004 | Kaddurah-Daouk et al. |
| 2005/0020492 A1 | 1/2005 | Bednarek |
| 2005/0186158 A1 | 8/2005 | Kaddurah-Daouk |
| 2005/0186194 A1 | 8/2005 | Kaddurah-Daouk |
| 2005/0186195 A1 | 8/2005 | Kaddurah-Daouk |
| 2005/0226840 A1 | 10/2005 | Kaddurah-Daouk |
| 2005/0227996 A1 | 10/2005 | Kaddurah-Daouk |
| 2006/0159719 A1 | 7/2006 | Cooke et al. |
| 2006/0167402 A1 | 7/2006 | Cooke et al. |
| 2006/0241021 A1 | 10/2006 | Kaddurah-Daouk et al. |
| 2007/0027090 A1 | 2/2007 | Kaddurah-Daouk et al. |
| 2007/0253944 A1 | 11/2007 | Kaddurah-Daouk |
| 2009/0221706 A1 | 9/2009 | Kaddurah-Daouk et al. |
| 2010/0113353 A1 | 5/2010 | Cooke et al. |
| 2010/0179106 A1 | 7/2010 | Khan |
| 2010/0226870 A1 | 9/2010 | Kaddurah-Daouk |
| 2010/0233084 A1 | 9/2010 | Narasimhaswamy et al. |
| 2010/0292336 A1 | 11/2010 | Mickle |
| 2010/0292337 A1 | 11/2010 | Mickle |
| 2010/0329997 A1 | 12/2010 | Kaddurah-Daouk |
| 2011/0008272 A1 | 1/2011 | Kaddurah-Daouk |
| 2011/0021632 A1 | 1/2011 | Kaddurah-Daouk |
| 2011/0085993 A1 | 4/2011 | Kaddurah-Daouk |
| 2011/0158925 A1 | 6/2011 | Ascione et al. |
| 2011/0262355 A1 | 10/2011 | Jenkins et al. |
| 2011/0262359 A1 | 10/2011 | Jenkins et al. |
| 2012/0141391 A1 | 6/2012 | Kaddurah-Daouk |
| 2012/0232066 A1 | 9/2012 | Jenkins et al. |
| 2012/0232111 A1 | 9/2012 | Kaminuma et al. |
| 2012/0245211 A1 | 9/2012 | Clark et al. |
| 2012/0295834 A1 | 11/2012 | Jenkins et al. |
| 2012/0328561 A1 | 12/2012 | Fujiwara et al. |
| 2013/0011364 A1 | 1/2013 | Fichert et al. |
| 2013/0021085 A1 | 1/2013 | Kumar et al. |
| 2013/0040877 A1 | 2/2013 | Kofoed et al. |
| 2013/0058958 A1 | 3/2013 | Bowen et al. |
| 2013/0059914 A1 | 3/2013 | Jenkins et al. |
| 2013/0072462 A1 | 3/2013 | Khan |
| 2013/0090488 A1 | 4/2013 | Dietz |
| 2013/0123169 A1 | 5/2013 | Kawahata et al. |
| 2013/0210701 A1 | 8/2013 | Jenkins et al. |
| 2013/0210745 A1 | 8/2013 | Guerlavais et al. |
| 2013/0274205 A1 | 10/2013 | Guerlavais et al. |
| 2013/0281324 A1 | 10/2013 | Gouliaev et al. |
| 2013/0281410 A1 | 10/2013 | Renshaw |
| 2014/0045798 A1 | 2/2014 | Khan |
| 2014/0121152 A1 | 5/2014 | Jenkins et al. |
| 2014/0141069 A1 | 5/2014 | Brewster |
| 2014/0206597 A1 | 7/2014 | Jenkins et al. |
| 2014/0224737 A1 | 8/2014 | Fichert et al. |
| 2014/0294727 A1 | 10/2014 | Narasimhaswamy et al. |
| 2015/0051155 A1 | 2/2015 | Guerlavais et al. |
| 2015/0126520 A1 | 5/2015 | Chiodo et al. |
| 2017/0056352 A1* | 3/2017 | Martinez .............. A61K 31/197 |
| 2017/0056353 A1* | 3/2017 | Martinez .............. A61K 31/197 |

FOREIGN PATENT DOCUMENTS

| | | |
|---|---|---|
| CA | 2329004 A1 | 1/2000 |
| CA | 2376375 A1 | 12/2000 |
| CA | 2376943 A1 | 1/2001 |
| CA | 2473229 A1 | 7/2003 |
| CA | 2698755 A1 | 3/2009 |
| CA | 2795222 A1 | 10/2011 |
| CA | 2801624 A1 | 12/2011 |
| CA | 2827662 A1 | 9/2012 |
| CA | 2852468 A1 | 4/2013 |
| CA | 2862038 A1 | 8/2013 |
| CA | 2864120 A1 | 8/2013 |
| EP | 0260118 A1 | 3/1988 |
| EP | 1656945 A1 | 5/2006 |
| EP | 1746099 A1 | 1/2007 |
| EP | 1880711 A1 | 1/2008 |
| EP | 2397127 A1 | 12/2011 |
| EP | 2399885 A1 | 12/2011 |
| EP | 2567705 A2 | 3/2013 |
| GB | 1379502 A | 1/1975 |
| JP | 3745439 B2 | 2/2006 |
| JP | 4317599 B2 | 8/2009 |
| JP | 2010-143922 A | 7/2010 |
| JP | 2010-143928 A | 7/2010 |
| JP | 2010-260861 A | 11/2010 |
| WO | WO-96/16031 A1 | 5/1996 |
| WO | WO-97/14401 A1 | 4/1997 |
| WO | WO-97/44324 A1 | 11/1997 |
| WO | WO-00/00195 A1 | 1/2000 |
| WO | WO-00/74701 A2 | 12/2000 |
| WO | WO-01/00203 A1 | 1/2001 |
| WO | WO-03/013574 A1 | 2/2003 |
| WO | WO-03/039449 A2 | 5/2003 |
| WO | WO-03/060091 A2 | 7/2003 |
| WO | WO-03/101402 A2 | 12/2003 |
| WO | WO-2004/069232 A2 | 8/2004 |
| WO | WO-2007/014756 A1 | 2/2007 |
| WO | WO-2008/043024 A2 | 4/2008 |
| WO | WO-2008/054544 A2 | 5/2008 |
| WO | WO-2008/092591 A2 | 8/2008 |
| WO | WO-2009/033130 A1 | 3/2009 |
| WO | WO-2009/098142 A1 | 8/2009 |
| WO | WO-2010/070243 A1 | 6/2010 |
| WO | WO-2011/082076 A1 | 7/2011 |
| WO | WO-2011/121008 A1 | 10/2011 |
| WO | WO-2011/127933 A1 | 10/2011 |
| WO | WO-2011/133149 A1 | 10/2011 |
| WO | WO-2011/133150 A1 | 10/2011 |
| WO | WO-2011/133348 A1 | 10/2011 |
| WO | WO-2011/139718 A1 | 11/2011 |
| WO | WO-2011/143534 A1 | 11/2011 |
| WO | WO-2011/160857 A2 | 12/2011 |
| WO | WO-2012/024611 A1 | 2/2012 |
| WO | WO-2012/047630 A2 | 4/2012 |
| WO | WO-2012/122412 A2 | 9/2012 |
| WO | WO-2012/122420 A2 | 9/2012 |
| WO | WO-2012/122422 A2 | 9/2012 |
| WO | 2012/138214 * | 10/2012 |
| WO | WO-2012/138214 A1 | 10/2012 |
| WO | WO-2012/173846 A2 | 12/2012 |
| WO | WO-2013/016668 A2 | 1/2013 |
| WO | WO-2013/059525 A1 | 4/2013 |
| WO | WO-2013/083642 A1 | 6/2013 |
| WO | WO-2013/123266 A1 | 8/2013 |
| WO | WO-2013/123267 A1 | 8/2013 |
| WO | WO-2013/183055 A1 | 12/2013 |
| WO | WO-2014/072490 A1 | 5/2014 |
| WO | WO-2014/138492 A1 | 9/2014 |
| WO | 2017/035331 * | 3/2017 |

* cited by examiner

PHARMACEUTICALLY ACCEPTABLE SALTS OF B-GUANIDINOPROPIONIC ACID WITH IMPROVED PROPERTIES AND USES THEREOF

BACKGROUND

β-Guanidinopropionic acid (β-GPA), also referred to as guanidinopropionic acid, beta-guanidinopropionic acid or, N-(aminoiminomethyl)-beta-alanine is a creatine analog. Studies on animals (rats, monkeys, hamsters) show that acidic guanidine derivatives such as β-GPA can ameliorate hyperglycemia in animal models of noninsulin-dependent diabetes. Accordingly, it is sometimes used as a dietary supplement in diabetic patients to regulate blood sugar levels. β-GPA is a white crystalline powder that is highly soluble in water (>50 mg/mL).

β-GPA has recently been found to be effective for the suppression of metastasis, particularly liver metastasis in gastrointestinal cancers, e.g., see International Patent Publication WO2014/071067. However, due to the physical properties of β-GPA in the solid state, e.g., poor flow properties and compressibility, there exists a need for β-GPA salts and formulations with improved physical properties and handling characteristics.

SUMMARY OF THE INVENTION

The present invention features new pharmaceutical salts of β-GPA which exhibit improved physical properties. In particular, the invention features salts of β-GPA with improved flow properties (e.g., improved Carr's index and/or Hausner ratio), such as fumarate salts, succinate salts, and oxalate salts. The invention also features pharmaceutical compositions including a pharmaceutically effective amount of one or more salts of β-GPA, as well as methods of treating cancer including administration of a formulation including a β-GPA salt of the invention to a subject in need thereof.

Accordingly, in a first aspect, the invention features a pharmaceutically acceptable salt of δ-guanidinopropionic acid having a Carr's Index of less than 20 (e.g., less than 15, less than 10, less than 6) and/or a Hausner ratio of less than 1.25 (e.g., less than 1.2, less than 1.15, less than 1.1). In some embodiments, the pharmaceutically acceptable salt is a salt of a dicarboxylic acid (e.g., fumaric acid, succinic acid, or oxalic acid). In some embodiments, the pharmaceutically acceptable salt is a fumarate salt (e.g., a 2:1 fumarate salt), a succinate salt (e.g., a 2:1 succinate salt), or an oxalate salt (e.g., a 1:1 oxalate salt).

In some embodiments, the pharmaceutically acceptable salt is crystalline (e.g., a 2:1 fumarate salt with platelet-like crystal morphology). In some embodiments, the pharmaceutically acceptable salt includes less than 40% by weight (e.g., less than 30%, less than 20%, less than 10%, less than 5%, less than 1% or between 30-40%, 25-35%, 20-30%, 15-25%, 10-20%, 5-15%, 1-10%) of amorphous compound. In some embodiments, the pharmaceutically acceptable salt is substantially free of amorphous compound. In some embodiments, the pharmaceutically acceptable salt is substantially free of any other salt or crystal form of β-GPA.

In some embodiments, the pharmaceutically acceptable salt is a 2:1 fumarate salt. In some embodiments, the pharmaceutically acceptable salt has an endothermic onset at about 251° C. (e.g., from 248° C. to 253° C., 249° C. to 254° C., 250° C. to 255° C., 248° C. to 255° C.) in differential scanning calorimetry (DSC) profile. In some embodiments, the pharmaceutically acceptable salt has an endothermic onset at about 187° C. (e.g., from 185° C. to 188° C., 186° C. to 189° C., 184° C. to 187° C., 184° C. to 189° C.) in differential scanning calorimetry (DSC) profile. In some embodiments, the pharmaceutically acceptable salt has two endothermic onsets in differential scanning calorimetry (DSC) profile. In some embodiments, the pharmaceutically acceptable salt has a loss of weight from 31° C. to 140° C. of less than 5% (e.g., less than 4%, less than 3%, less than 2%, less than 1%) as measured by thermal gravimetric analysis.

In some embodiments, the pharmaceutically acceptable salt is a 1:1 fumarate salt. In some embodiments, the pharmaceutically acceptable salt has an endothermic onset at about 171° C. (e.g., from 169° C. to 173° C., 170° C. to 173° C., 169° C. to 172° C., 170° C. to 172° C.) in differential scanning calorimetry (DSC) profile. In some embodiments, the pharmaceutically acceptable salt has a loss of weight from 31° C. to 140° C. of less than 5% (e.g., less than 4%, less than 3%, less than 2%, less than 1%) as measured by thermal gravimetric analysis.

In some embodiments, the pharmaceutically acceptable salt has at least one peak at diffraction angle 2θ (°) of 20±0.5 as measured by X-ray powder diffractometry. In some embodiments, the pharmaceutically acceptable salt further has at least one peak at diffraction angle 2θ (°) of 20±0.5, 20.5±0.5, and/or 23±0.5 as measured by X-ray powder diffractometry. In some embodiments, the pharmaceutically acceptable salt has one or more (e.g., two or more, three or more, four or more, five or more, six or more, seven or more, eight or more, nine or more, ten or more, eleven or more, twelve or more, thirteen or more, fourteen or more) peaks listed in Table 1 as measured by X-ray diffractometry or calculated from X-ray diffractometry. In some embodiments, the pharmaceutically acceptable salt has all of the peaks listed in Table 1 as measured by X-ray diffractometry or calculated from X-ray diffractometry.

TABLE 1

XRPD peak list for the 1:1 fumarate salt of β-GPA

| 2θ (°) | Intensity |
|---|---|
| 11.78 | 5.5 |
| 13.95 | 6.0 |
| 17.42 | 6.4 |
| 19.22 | 12.5 |
| 19.68 | 21.1 |
| 20.02 | 8.4 |
| 20.58 | 27.4 |
| 21.01 | 6.3 |
| 22.87 | 22.4 |
| 23.74 | 6.4 |
| 24.74 | 5.5 |
| 25.57 | 5.4 |
| 26.74 | 100 |
| 28.84 | 12.3 |
| 29.48 | 7.1 |

In some embodiments, the pharmaceutically acceptable salt has one or more (e.g., two or more, three or more, four or more, five or more, six or more, seven or more, eight or more, nine or more, ten or more, eleven or more, twelve or more, thirteen or more, fourteen or more) peaks listed in Table 2 as measured by X-ray diffractometry or calculated from X-ray diffractometry. In some embodiments, the pharmaceutically acceptable salt has all of the peaks listed in Table 2 as measured by X-ray diffractometry or calculated from X-ray diffractometry.

TABLE 2

XRPD peak list for the 2:1 fumarate salt of β-GPA

| 2θ (°) | Intensity |
|---|---|
| 17.47 | 1.8 |
| 19.26 | 6.8 |
| 19.71 | 3.3 |
| 20.67 | 5.3 |
| 22.90 | 9.3 |
| 25.91 | 2.5 |
| 26.78 | 100 |
| 27.51 | 3.2 |
| 28.73 | 2.7 |
| 29.12 | 1.8 |
| 31.16 | 2.5 |
| 33.04 | 1.7 |
| 33.98 | 3.5 |
| 35.27 | 3.1 |
| 39.05 | 2.7 |
| 23.82 | 2.9 |
| 24.09 | 3.2 |
| 20.97 | 5.7 |

In some embodiments, the pharmaceutically acceptable salt when analyzed by single crystal X-ray diffractometry has a unit cell of the space group P 2$_1$/n, having dimensions of a=about 12.4541 Å, b=about 9.5447 Å, c=about 14.4013 Å and α=about 90°, β=about 100.5°, γ=about 90° and/or a cell volume of about 1683.39 Å$^3$.

In some embodiments, the pharmaceutically acceptable salt has at least one peak at 3300±1 cm$^{-1}$ as measured by Raman spectroscopy. In some embodiments, the pharmaceutically acceptable salt has at least one peak at 3188±1 cm$^{-1}$ as measured by Raman spectroscopy. In some embodiments, the pharmaceutically acceptable salt has at least one peak at 3049±1 cm$^{-1}$ as measured by Raman spectroscopy. In some embodiments, the pharmaceutically acceptable salt has at least one peak at 2941±1 cm$^{-1}$ as measured by Raman spectroscopy. In some embodiments, the pharmaceutically acceptable salt has at least one peak at 2886±1 cm$^{-1}$ as measured by Raman spectroscopy. In some embodiments, the pharmaceutically acceptable salt has at least one peak at 1713±1 cm$^{-1}$ as measured by Raman spectroscopy. In some embodiments, the pharmaceutically acceptable salt has at least one peak at 1653±1 cm$^{-1}$ as measured by Raman spectroscopy. In some embodiments, the pharmaceutically acceptable salt has at least one peak at 1483±1 cm$^{-1}$ as measured by Raman spectroscopy. In some embodiments, the pharmaceutically acceptable salt has at least one peak at 1421±1 cm$^{-1}$ as measured by Raman spectroscopy. In some embodiments, the pharmaceutically acceptable salt has at least one peak at 1382±1 cm$^{-1}$ as measured by Raman spectroscopy. In some embodiments, the pharmaceutically acceptable salt has at least one peak at 1305±1 cm$^{-1}$ as measured by Raman spectroscopy. In some embodiments, the pharmaceutically acceptable salt has at least one peak at 1268±1 cm$^{-1}$ as measured by Raman spectroscopy. In some embodiments, the pharmaceutically acceptable salt has at least one peak at 1190±1 cm$^{-1}$ as measured by Raman spectroscopy. In some embodiments, the pharmaceutically acceptable salt has at least one peak at 1084±1 cm$^{-1}$ as measured by Raman spectroscopy. In some embodiments, the pharmaceutically acceptable salt has at least one peak at 997±1 cm$^{-1}$ as measured by Raman spectroscopy. In some embodiments, the pharmaceutically acceptable salt has at least one peak at 896±1 cm$^{-1}$ as measured by Raman spectroscopy. In some embodiments, the pharmaceutically acceptable salt has at least one peak at 681±1 cm$^{-1}$ as measured by Raman spectroscopy. In some embodiments, the pharmaceutically acceptable salt has at least one peak at 625±1 cm$^{-1}$ as measured by Raman spectroscopy. In some embodiments, the pharmaceutically acceptable salt has at least one peak at 555±1 cm$^{-1}$ as measured by Raman spectroscopy. In some embodiments, the pharmaceutically acceptable salt has at least one peak at 486±1 cm$^{-1}$ as measured by Raman spectroscopy. In some embodiments, the pharmaceutically acceptable salt has one or more (e.g., two or more, three or more, four or more, five or more, six or more, seven or more, eight or more, nine or more, ten or more, eleven or more, twelve or more, thirteen or more, fourteen or more) peaks listed in Table 3 as measured by Raman spectroscopy. In some embodiments, the pharmaceutically acceptable salt has all of the peaks listed in Table 3 as measured by Raman spectroscopy.

TABLE 3

Raman spectra peak list for the 2:1 fumarate salt of β-GPA
Raman Shift (cm-1)

| |
|---|
| 3300.48 |
| 3188.58 |
| 3049.73 |
| 2941.74 |
| 2886.78 |
| 1713.28 |
| 1653.49 |
| 1483.79 |
| 1421.11 |
| 1382.54 |
| 1305.4 |
| 1268.76 |
| 1190.66 |
| 1084.59 |
| 997.81 |
| 896.56 |
| 681.53 |
| 625.6 |
| 555.21 |
| 486.79 |

In some embodiments, the pharmaceutically acceptable salt is a 1:1 oxalate salt. In some embodiments, the pharmaceutically acceptable salt has at least one peak at diffraction angle 2θ (°) of 27.5±0.5 as measured by X-ray powder diffractometry. In some embodiments, the pharmaceutically acceptable salt has one or more (e.g., two or more, three or more, four or more, five or more, six or more, seven or more, eight or more, nine or more, ten or more, eleven or more, twelve or more, thirteen or more, fourteen or more) peaks listed in Table 4. In some embodiments, the pharmaceutically acceptable salt has all of the peaks listed in Table 4 as measured by X-ray powder diffractometry.

TABLE 4

XRPD peak list for the 1:1 oxalate salt of β-GPA

| Angle (2θ) degree | Intensity % |
|---|---|
| 10.66 | 2.1 |
| 14.36 | 1.7 |
| 15.26 | 1.8 |
| 17.79 | 2.0 |
| 20.24 | 2.8 |
| 20.78 | 1.8 |
| 23.69 | 4.0 |
| 26.60 | 1.8 |
| 27.45 | 100.0 |
| 31.50 | 1.7 |
| 33.62 | 1.9 |
| 34.94 | 1.8 |

TABLE 4-continued

XRPD peak list for the 1:1 oxalate salt of β-GPA

| Angle (2θ) degree | Intensity % |
|---|---|
| 35.76 | 1.7 |
| 36.69 | 1.6 |
| 37.23 | 1.9 |

In some embodiments, the pharmaceutically acceptable salt is a 2:1 succinate salt. In some embodiments, the pharmaceutically acceptable salt has at least one peak at diffraction angle 2θ (°) of 27±0.5 as measured by X-ray powder diffractometry. In some embodiments, the pharmaceutically acceptable salt has one or more (e.g., two or more, three or more, four or more, five or more, six or more, seven or more, eight or more, nine or more, ten or more, eleven or more, twelve or more, thirteen or more, fourteen or more) peaks listed in Table 5. In some embodiments, the pharmaceutically acceptable salt has all of the peaks listed in Table 5 as measured by X-ray powder diffractometry.

TABLE 5

XRPD peak list for the 2:1 succinate salt of β-GPA

| Angle (2θ) degree | Intensity % |
|---|---|
| 4.87 | 3.9 |
| 16.29 | 4.4 |
| 19.99 | 29.3 |
| 20.62 | 14.8 |
| 22.73 | 3.9 |
| 23.13 | 4.5 |
| 25.60 | 4.5 |
| 26.23 | 4.5 |
| 26.70 | 100.0 |
| 27.26 | 12.4 |
| 31.32 | 4.4 |
| 34.24 | 4.0 |
| 35.19 | 4.6 |
| 36.41 | 4.3 |
| 38.30 | 5.6 |

In another aspect, the invention features a composition (e.g., an aqueous composition) including any of the foregoing pharmaceutically acceptable salts and a pharmaceutically acceptable excipient. In some embodiments, the pharmaceutically acceptable salt contains less than 10% by weight (e.g., less than 5%, less than 1%) of amorphous compound. In some embodiments, the pharmaceutically acceptable salt is substantially free of amorphous compound.

In another aspect, the invention features a composition (e.g., an aqueous composition) including the fumarate salt of β-guanidinopropionic acid, wherein at least 80% (at least 85%, at least 90%, at least 95%, at least 99%) of the fumarate salt of β-guanidinopropionic acid is a 2:1 salt (e.g., wherein the composition is substantially free of the 1:1 fumarate salt of β-guanidinopropionic acid) and a pharmaceutically acceptable excipient.

In some embodiments of any of the foregoing compositions, the pharmaceutically acceptable excipient includes 1,3-butanediol, mannitol, water, Ringer's solution, or isotonic sodium chloride solution. In some embodiments of any of the foregoing compositions, the composition is formulated for intravenous infusion.

In another aspect, the invention features a method for treating cancer (e.g., gastrointestinal cancer such as colon cancer or gastric cancer, pancreatic cancer, liver cancer, breast cancer, prostate cancer, lung cancer, and melanoma) in a subject in need thereof, including administering to the subject an effective amount of any of the foregoing pharmaceutically acceptable salts or compositions.

In another aspect, the invention features a method for treating metastatic cancer (e.g., metastatic gastrointestinal cancer such as colon cancer or gastric cancer) in a subject in need thereof, including administering to the subject an effective amount of any of the foregoing pharmaceutically acceptable salts or compositions. In some embodiments, the effective amount includes an amount effective to suppress metastatic colonization (e.g., metastatic colonization in the liver) of the cancer (e.g., gastrointestinal cancer such as colorectal cancer or gastric cancer).

In another aspect, the invention features a method for treating cancer (e.g., gastrointestinal cancer such as colon cancer or gastric cancer) in a subject in need thereof, comprising injecting into the subject an effective amount of an aqueous composition comprising any of the foregoing pharmaceutically acceptable salts and a pharmaceutically acceptable excipient. In some embodiments, the cancer is metastatic cancer. In some embodiments, the effective amount is an amount effective to suppress metastatic colonization of the cancer.

In another aspect, the invention features a method of treating metastatic cancer (e.g., gastrointestinal cancer such as colorectal cancer, esophageal cancer, or gastric cancer, pancreatic cancer, liver cancer, breast cancer, prostate cancer, lung cancer, and melanoma) in a subject in need thereof comprising: (a) providing a subject identified to have, or to be at risk of having, metastatic cancer on the basis of the expression level of miR-483-5p and/or miR-551a is below a predetermined reference value or the expression level of CKB and/or SLC6a8 is above a predetermined reference value; and (b) administering to the subject an effective amount of any of the foregoing pharmaceutically acceptable salt or compositions.

In some embodiments any of the foregoing methods further include administering an additional therapy (e.g., an additional therapeutic agent) to the subject. In some embodiments, the additional therapy is a therapeutic agent such as cyclocreatine, a RNAi agent, a nucleic acid, a vector, 5-fluorouracil, Oxaliplatin, Irinotecan, Capecitabine, Gemcitabine, Cetuximab, Taxol, Avastin, folinic acid (leucovorin), Regorafenib, Zaltrap, topoisomerase I inhibitors, NKTR-102, Tivantinib, PX-866, Sorafenib, Linifanib, kinase inhibitors, Telatinib, XL281 (BMS-908662), Robatumumab, or IGF1-R inhibitors.

In another aspect, the invention features a method of producing a pharmaceutically acceptable 1:1 fumarate salt of β-guanidinopropionic acid. This method includes combining β-guanidinopropionic acid and fumaric acid in an amount sufficient to produce a pharmaceutically acceptable 1:1 fumarate salt of β-guanidinopropionic acid. In some embodiments, the method includes dissolving the β-guanidinopropionic acid and the fumaric acid in a solvent and the 1:1 fumarate salt of β-guanidinopropionic acid precipitates from the solvent. In some embodiments, the method further includes recrystallization of the 1:1 fumarate salt of β-guanidinopropionic acid.

In another aspect, the invention features a method of producing a pharmaceutically acceptable 2:1 fumarate salt of β-guanidinopropionic acid. This method includes combining β-guanidinopropionic acid and fumaric acid in an amount sufficient to produce a pharmaceutically acceptable 2:1 fumarate salt of β-guanidinopropionic acid. In some embodiments, the method includes dissolving the β-guanidinopropionic acid and the fumaric acid in a solvent and the 2:1 fumarate salt of β-guanidinopropionic acid precipitates from the solvent. In some embodiments, the method further includes recrystallization of the 2:1 fumarate salt of β-guanidinopropionic acid.

BRIEF DESCRIPTION OF THE DRAWINGS

FIG. 29A) 1:1 hydrochloride salt of β-GPA; FIG. 29B) 1:1 phosphate salt of β-GPA; FIG. 29C) 1:1 mesylate salt of β-GPA; FIG. 29D) 1:1 maleate salt of β-GPA; FIG. 29E) 1:1 maleate of β-GPA; FIG. 29F) 2:1 maleate salt of β-GPA; FIG. 29G) 1:1 fumarate salt of β-GPA; FIG. 29H) 1:1 malate salt of β-GPA; FIG. 29I) 2:1 succinate salt of β-GPA; and FIG. 29J) 1:1 oxalate salt of β-GPA.

DETAILED DESCRIPTION OF THE INVENTION

Figure 1:
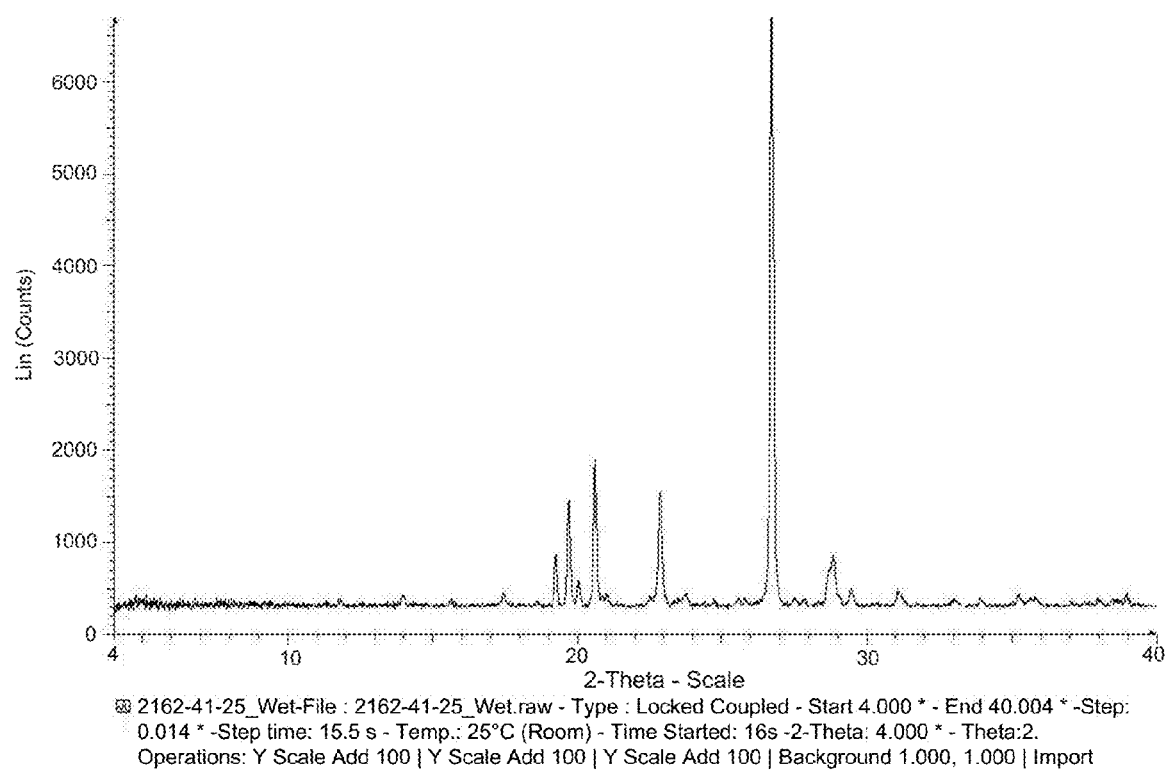
FIG. 1 is an image depicting X-ray powder diffraction (XRPD) pattern obtained for a crystalline form of the 1:1 fumarate salt of β-GPA.

To identify β-GPA salts with improved properties, the present inventors carried out salt screening experiments with 19 different counterions and eight different solvent systems. Ten of the counterions were prepared in crystalline forms and their properties assessed. Following identification of preferred salts with optimal properties, polymorph screening of these salts was conducted.

β-GPA

β-GPA has the structure:

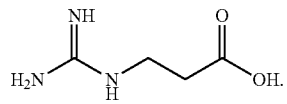

β-GPA is zwitterionic and highly soluble in water (>50 mg/mL), but has low solubility in organic solvents. β-GPA possesses a basic guanidino group, and is thus capable of forming both 1:1 (β-GPA:acid) and 2:1 (β-GPA:acid) salts with diacids. As used herein, a "2:1 salt" of β-GPA with a diacid, e.g., a 2:1 succinate salt, refers to a salt including two molecules of β-GPA and one molecule of the diacid, e.g., a "2:1 succinate salt" includes two molecules of β-GPA and one molecule of succinic acid.

Free β-GPA in solid state is highly crystalline and is generally present as an anhydrate. The crystalline form is non-hygroscopic (e.g., with ~0.3% water uptake at 80% humidity at 25° C.) with a sharp melting point at 219° C. and an endothermic event at 235° C. by DSC. The crystals of β-GPA have a plate-like crystal morphology. No degradation was observed in experiments at 40° C. at 75% humidity after 4 weeks.

The flow properties of β-GPA are sub-optimal. The bulk density is 0.389 g/cc and the tapped density is 0.627 g/cc. These measurements can be used to calculate the Carr's index and Hausner ratio for a substance. The Carr's index and Hausner ratio are indicators of flowability of a powder. As known in the art, e.g., as described in Carr R. L. Chem. Eng. 1965, 72, 163-168, the relationship to flowability of a powder to the Carr's index and Hausner ratio is based on the scale shown in Table 6 below.

TABLE 6

Prediction of powder flowability based on Carr's index and Hausner ratio values

| Carr's Index | Flow character | Hausner Ratio |
| --- | --- | --- |
| 1-10 | Excellent | 1.00-1.11 |
| 11-15 | Good | 1.12-1.18 |
| 16-20 | Fair | 1.19-1.25 |
| 21-25 | Passable | 1.26-1.34 |
| 26-31 | Poor | 1.35-1.45 |

TABLE 6-continued

Prediction of powder flowability based on Carr's index and Hausner ratio values

| Carr's Index | Flow character | Hausner Ratio |
| --- | --- | --- |
| 32-37 | Very poor | 1.46-1.59 |
| >38 | Very very poor | >1.60 |

The Carr's index and Hausner ratio for β-GPA are 37.9 (Very poor) and 1.610 (Very very poor) respectively. Experiments utilizing a Hanson Flodex instrument confirmed the poor flowability of β-GPA predicted by the Carr's index and Hausner ratio. Thus, there exists a need to find a β-GPA salt with improved physical properties.

Salts

Seventy-six salt screening experiments were carried out with 19 different counterions in different solvent systems including ethanol:water (9:1), isopropyl alcohol, acetone: water (9:1), and acetonitrile. The ten counterions that were prepared in crystalline form were salts prepared with hydrochloric acid, phosphoric acid, methanesulfonic acid, maleic acid, fumaric acid, L-malic acid, succinic acid, and oxalic acid. All of the experiments with basic compounds, e.g., L-aspartic acid, sodium hydroxide, potassium hydroxide, or magnesium hydroxide, resulted in isolation of only β-GPA or the basic compound individually.

Of the salts that were prepared, the hydrochloric acid, L-malic acid, phosphoric acid, methanesulfonic acid, and ethanesulfonic acid salts were found to be stable in dry conditions, but deliquesced under high humidity conditions. The maleic acid, fumaric acid, succinic acid, and oxalic acid salts were found to be stable in both dry and humid conditions. The maleic acid, fumaric acid, and oxalic acid salts were found to have 1:1 (β-GPA:acid) stoichiometry, whereas the succinic acid salt was found to have 2:1 (β-GPA:acid) stoichiometry. Further experiments to generate 2:1 salts with fumaric, oxalic, and maleic acid were conducted, resulting in the preparation of 2:1 salts with maleic acid and fumaric acid.

Dynamic vapor sorption experiments were conducted on the 1:1 maleate salt, the 1:1 fumarate salt, the 2:1 succinate salt, and the 1:1 oxalate salt. The fumarate, succinate, and oxalate salts were found to exhibit less than 1% moisture uptake during the DVS experiment with no form change observed by XRPD after the experiment. The maleate salt exhibited ~25% moisture uptake with no form change observed by XRPD after the experiment. Solid form stability studies of the fumarate, succinate, and oxalate salts were carried out at 40° C. and 75% humidity for seven days. All three salts were found to be stable under these conditions.

The bulk density and tapped density for the three salts was determined as shown in Table 7 below.

TABLE 7

Bulk density and tapped density measurements

| Salt | Bulk density | Tapped density |
| --- | --- | --- |
| oxalate (1:1) | 0.505 g/cc | 0.623 g/cc |
| succinate (2:1) | 0.405 g/cc | 0.472 g/cc |
| fumarate (2:1) | 0.576 g/cc | 0.613 g/cc |

The Carr's index and Hausner ratios were calculated for each of the three salts, and as shown in Table 8, the three salts exhibit greatly improved predicted flow properties compared to β-GPA. The predicted flow properties were confirmed by experiments utilizing a Hanson Flodex instrument.

TABLE 8

Flow properties of three β-GPA salts compared to β-GPA

| Compound | Carr's index | Hausner ratio | Flow character |
| --- | --- | --- | --- |
| β-GPA | 37.9 | 1.610 | Very poor |
| β-GPA oxalate (1:1) | 18.7 | 1.23 | Fair |
| β-GPA succinate (2:1) | 14.3 | 1.167 | Good |
| β-GPA fumarate (2:1) | 5.9 | 1.063 | Excellent |

Polymorph screening of the 2:1 fumarate salt of β-GPA was carried out in 15 different solvent systems at 15° C. and 45° C. and the solubility of the salt was determined gravimetrically. Most of the experiments resulted in no change in polymorph. However, a new polymorph of β-GPA (Pattern 7C) was formed upon lypohilization of the 2:1 salt and fast evaporation, or lyophilization of β-GPA and fumaric acid in 2:1 (β-GPA:acid) stiochiometry. The new polymorph was found to contain some amorphous material, and was unstable.

Crystalline β-GPA, or a pharmaceutically acceptable salt thereof, is defined as a solid comprising β-GPA, or a pharmaceutically acceptable salt thereof, in which the constituent molecules are packed in a regularly ordered repeating pattern extending in all three spatial dimensions. Identification of crystallinity is readily accomplished in a number of ways known to those skilled in the art. Microscopic examination of a test composition will reveal the presence of regular shapes suggesting ordered internal structure, e.g., the 1:1 fumarate salt of β-GPA produced in Example 2 has rod-like morphology.

Figure 43:
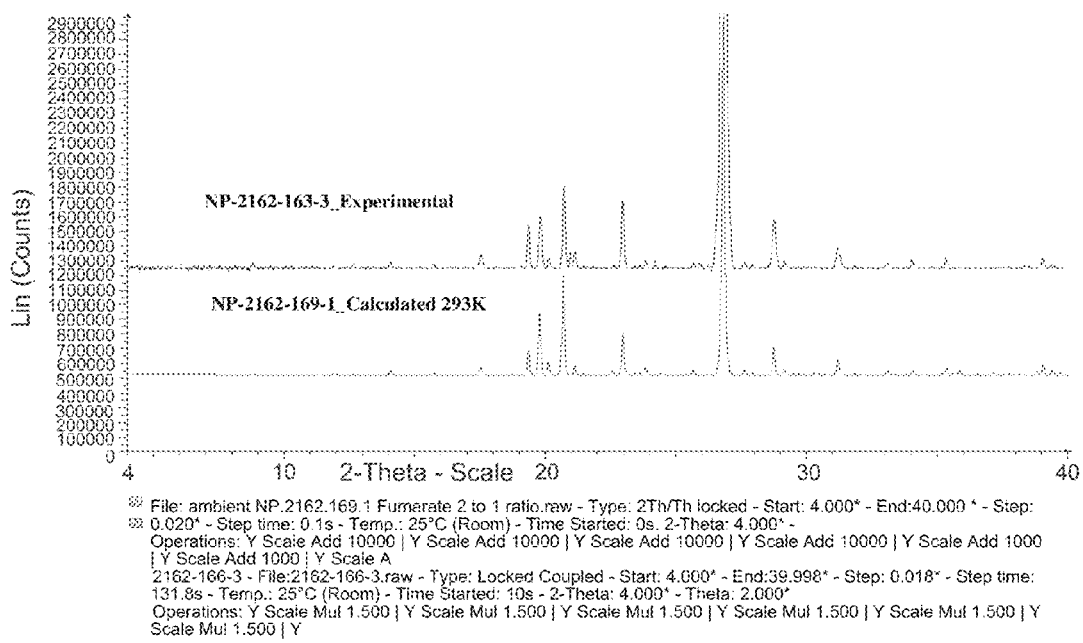
FIG. 43 is an image depicting the X-ray powder diffraction (XRPD) pattern obtained for a crystalline form of the 2:1 fumarate salt of β-GPA and the X-ray powder diffraction (XRPD) pattern calculated based on the unit cell identified during single crystal analysis (Pattern 7A).

XRPD is another method for identifying crystalline β-GPA, or pharmaceutically acceptable salts thereof. The regularly ordered structure of constituent molecules in crystal diffracts incident X-rays in a distinct pattern depicted as a spectrum of peaks. This pattern of peaks for the 2:1 fumarate salt of β-GPA is shown in FIG. 43. While the XRPD peaks for a particular crystal may vary in intensity, the same general pattern will be present in replicate XRPD analysis.

Crystalline 2:1 fumarate salt of β-GPA exhibits an XRPD dominant peak at about 27 2θ (°), ordinarily about 26.7. By "about," as used herein, is meant within the typical variation in measurement of XRPD peaks. Such variations may result from the use of different instruments, instrument settings, batches of product, post-crystallization processing such as micronization or milling, and with varying sample preparation methods. In general, about means±0.5 2θ (°).

Illustrative examples of other dominant peaks for crystalline 2:1 fumarate salt of β-GPA are at about 19, 20, 21, 23, and 29 2θ (°), ordinarily 19.2, 19.6, 20.5, 22.8, and 28.6 2θ (°). Representative peaks for crystalline 2:1 fumarate salt of β-GPA are shown in Table 2.

The identification of a crystalline form of β-GPA, or a pharmaceutically acceptable salt thereof, need not require the presence of any one or more of the dominant peaks seen in FIG. 43 or listed in Table 2. The presence or absence of dominant peaks is ordinarily taken into account with other diagnostic characteristics, e.g., DSC thermogram or TGA graph, to identify a candidate as a particular crystalline form of β-GPA, or a pharmaceutically acceptable salt thereof.

Crystalline 1:1 fumarate salt of β-GPA is also characterized by DSC thermogram which reveals an endothermic onset at 171° C. in differential scanning calorimetry profile. Typically, some variation in this measurement also will be encountered (e.g., ±1-3° C.).

Crystalline 2:1 fumarate salt of β-GPA is also characterized by DSC thermogram which reveals an endothermic onset at 187° C. and 251° C. in differential scanning calorimetry profile. Typically, some variation in this measurement also will be encountered (e.g., ±1-3° C.).

Crystalline 1:1 and 2:1 fumarate salt of β-GPA may also be characterized by thermal gravimetric analysis, e.g., by a loss of weight from 31° C. to 140° C. of less than 1%.

Treatment Methods

β-GPA has recently been found to be effective for the suppression of metastasis. The mechanism of action has been hypothesized as inhibition of creatine transport and/or creatine kinase. The phosphocreatine system promotes metastasis by enhancing the survival of disseminated cancer cells in the liver by acting as an energetic store for ATP generation to endure hepatic hypoxia. Inhibition of creatine transport into cancer cells limits the amount of phosphocreatine available to use in the production of ATP. Inhibition of creatine kinase inhibits the production of ATP through conversion of phosphocreatine to creatine.

Typical vascularized tumors that can be treated with the method include solid tumors, particularly carcinomas, which require a vascular component for the provision of oxygen and nutrients. Exemplary solid tumors include, but are not limited to, carcinomas of the lung, breast, bone, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, Kaposi's sarcoma, and sarcomas.

Treating cancer can result in a reduction in size or volume of a tumor. For example, after treatment, tumor size is reduced by 5% or greater (e.g., 10%, 20%, 30%, 40%, 50%, 60%, 70%, 80%, 90% or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90% or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with a pharmaceutically acceptable salt of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of the invention. A decrease in the mortality rate of a population may also be measured, for example, by calculating for a population the average number of disease-related deaths per unit time following completion of a first round of treatment with a pharmaceutically acceptable salt of the invention.

Compositions

Within the scope of this invention is a composition that contains a suitable excipient and one or more of the pharmaceutically acceptable salts described above. The composition can be a pharmaceutical composition that contains a pharmaceutically acceptable excipient, a dietary composition that contains a dietarily acceptable suitable excipient, or a cosmetic composition that contains a cosmetically acceptable excipient.

The term "pharmaceutical composition" refers to the combination of an active agent with a excipient, inert or active, making the composition especially suitable for diagnostic or therapeutic use in vivo or ex vivo. A "pharmaceutically acceptable excipient," after administered to or upon a subject, does not cause undesirable physiological effects. The excipient in the pharmaceutical composition must be "acceptable" also in the sense that it is compatible with the active ingredient and can be capable of stabilizing it. One or more solubilizing agents can be utilized as pharmaceutical excipients for delivery of an active compound. Examples of a pharmaceutically acceptable excipient include, but are not limited to, biocompatible vehicles, adjuvants, additives, and diluents to achieve a composition usable as a dosage form. Examples of other excipients include colloidal silicon oxide, magnesium stearate, cellulose, sodium lauryl sulfate, and D&C Yellow #10.

As used herein, the term "pharmaceutically acceptable salt" refers to those salts which are, within the scope of sound medical judgment, suitable for use in contact with the tissues of humans and lower animals without undue toxicity, irritation, or allergic response, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66:1-19 (1977). The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, fumaric, or malonic acid or by using other methods used in the art such as ion exchange. Other pharmaceutically acceptable salts, include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Representative alkali or alkaline earth metal salts include sodium, lithium, potassium, calcium, and magnesium. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutical compositions of the present invention additionally include a pharmaceutically acceptable excipient, which, as used herein, includes any and all solvents, diluents, or other liquid vehicle, dispersion or suspension aids, surface active agents, isotonic agents, thickening or emulsifying agents, preservatives, solid binders, and lubricants, as suited to the particular dosage form desired. Remington's Pharmaceutical Sciences, Sixteenth Edition, E. W. Martin (Mack Publishing Co., Easton, Pa., 1980) discloses various excipients used in formulating pharmaceutical compositions and known techniques for the preparation thereof. Except insofar as any conventional excipient medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable excipients include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; natural and synthetic phospholipids, such as soybean and egg yolk phosphatides, lecithin, hydrogenated soy lecithin, dimyristoyl lecithin, dipalmitoyl lecithin, distearoyl lecithin, dioleoyl lecithin, hydroxylated lecithin, lysophosphatidylcholine, cardiolipin, sphingomyelin, phosphatidylcholine, phosphatidyl ethanolamine, diastearoyl phosphatidylethanolamine (DSPE) and its pegylated esters, such as DSPE-PEG750 and, DSPE-PEG2000, phosphatidic acid, phosphatidyl glycerol and phosphatidyl serine. Commercial grades of lecithin which are preferred include those which are available under the trade name Phosal® or Phospholipon® and include Phosal 53 MCT, Phosal 50 PG, Phosal 75 SA, Phospholipon 90H, Phospholipon 90G and Phospholipon 90 NG; soy-phosphatidylcholine (SoyPC) and DSPE-PEG2000 are particularly preferred; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The above-described composition, in any of the forms described above, can be used for treating cancer, or any other disease or condition described herein. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment. A pharmaceutical composition of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acids, such as, but not limited to, oleic acid and its glyceride derivatives, are useful in the preparation of injectables, as are natural pharmaceutically acceptable oils, such as, but not limited to, olive oil or castor oil, orpolyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used excipients include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. In some embodiments, the pharmaceutically acceptable salts of the invention may be formulated as microparticulates such as by extrusion spheronization. In some embodiments, the pharmaceutically acceptable salts of the invention are formulated in an immediate release formulation. In some embodiments, the pharmaceutically acceptable salts of the invention are formulated in a sustained release formulation.

Pharmaceutical compositions for topical administration according to the described invention can be formulated as solutions, ointments, creams, suspensions, lotions, powders, pastes, gels, sprays, aerosols, or oils. Alternatively, topical formulations can be in the form of patches or dressings impregnated with active ingredient(s), which can optionally include one or more excipients or diluents. In some preferred embodiments, the topical formulations include a material that would enhance absorption or penetration of the active agent(s) through the skin or other affected areas.

A topical composition contains a safe and effective amount of a dermatologically acceptable excipient suitable for application to the skin. A "cosmetically acceptable" or "dermatologically-acceptable" composition or component refers a composition or component that is suitable for use in contact with human skin without undue toxicity, incompatibility, instability, or allergic response. The excipient enables an active agent and optional component to be delivered to the skin at an appropriate concentration(s). The excipient thus can act as a diluent, dispersant, solvent, or the like to ensure that the active materials are applied to and distributed evenly over the selected target at an appropriate concentration. The excipient can be solid, semi-solid, or liquid. The excipient can be in the form of a lotion, a cream, or a gel, in particular one that has a sufficient thickness or yield point to prevent the active materials from sedimenting. The excipient can be inert or possess dermatological benefits. It also should be physically and chemically compatible with the active components described herein, and should not unduly impair stability, efficacy, or other use benefits associated with the composition.

Combination Therapies

In some embodiments, the pharmaceutical composition may further include an additional compound having antiproliferative activity. The additional compound having antiproliferative activity can be selected from a group of antiproliferative agents including those shown in Table 9.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects).

By "antiproliferative agent" is meant any antiproliferative agent, including those antiproliferative agents listed in Table 9, any of which can be used in combination with a pharmaceutically acceptable salt of the invention to treat the medical conditions recited herein. Antiproliferative agents also include organo-platine derivatives, naphtoquinone and benzoquinone derivatives, chrysophanic acid and anthroquinone derivatives thereof.

TABLE 9

| | |
|---|---|
| Alkylating agents | Busulfan |
| | dacarbazine |
| | ifosfamide |
| | hexamethylmelamine |
| | thiotepa |
| | dacarbazine |
| | lomustine |
| | cyclophosphamide |
| | Chlorambucil |
| | procarbazine |
| | altretamine |
| | estramustine phosphate |
| | mechlorethamine |
| | streptozocin |
| | temozolomide |
| | Semustine |
| Platinum agents | spiroplatin |
| | tetraplatin |
| | ormaplatin |
| | iproplatin |
| | ZD-0473 (AnorMED) |
| | oxaliplatin |
| | carboplatin |
| | lobaplatin (Aeterna) |
| | satraplatin (Johnson Matthey) |
| | BBR-3464 (Hoffmann-La Roche) |
| | SM-11355 (Sumitomo) |
| | AP-5280 (Access) |
| | cisplatin |
| Antimetabolites | azacytidine |
| | Floxuridine |
| | 2-chlorodeoxyadenosine |
| | 6-mercaptopurine |
| | 6-thioguanine |
| | cytarabine |
| | 2-fluorodeoxy cytidine |
| | methotrexate |
| | tomudex |
| | fludarabine |
| | raltitrexed |
| | trimetrexate |
| | deoxycoformycin |
| | pentostatin |
| | hydroxyurea |
| | decitabine (SuperGen) |
| | clofarabine (Bioenvision) |
| | irofulven (MGI Pharma) |
| | DMDC (Hoffmann-La Roche) |
| | ethynylcytidine (Taiho) |
| | gemcitabine |
| | capecitabine |
| Topoisomerase inhibitors | amsacrine |
| | epirubicin |
| | etoposide |
| | teniposide or mitoxantrone |
| | 7-ethyl-10-hydroxy-camptothecin |
| | dexrazoxanet (TopoTarget) |
| | pixantrone (Novuspharma) |
| | rebeccamycin analogue (Exelixis) |
| | BBR-3576 (Novuspharma) |
| | rubitecan (SuperGen) |
| | irinotecan (CPT-11) |
| | topotecan |
| | exatecan mesylate (Daiichi) |
| | quinamed (ChemGenex) |
| | gimatecan (Sigma-Tau) |
| | diflomotecan (Beaufour-Ipsen) |
| | TAS-103 (Taiho) |
| | elsamitrucin (Spectrum) |
| | J-107088 (Merck & Co) |
| | BNP-1350 (BioNumerik) |
| | CKD-602 (Chong Kun Dang) |
| | KW-2170 (Kyowa Hakko) |
| | hydroxycamptothecin (SN-38) |
| Antitumor antibiotics | valrubicin |
| | therarubicin |
| | idarubicin |
| | rubidazone |
| | plicamycin |
| | porfiromycin |
| | mitoxantrone (novantrone) |
| | amonafide |
| | azonafide |
| | anthrapyrazole |
| | oxantrazole |
| | losoxantrone |
| | MEN-10755 (Menarini) |
| | GPX-100 (Gem Pharmaceuticals) |
| | Epirubicin |
| | mitoxantrone |
| | doxorubicin |
| Antimitotic agents | colchicine |
| | vinblastine |
| | vindesine |
| | dolastatin 10 (NCI) |
| | rhizoxin (Fujisawa) |
| | mivobulin (Warner-Lambert) |
| | cemadotin (BASF) |
| | RPR 109881A (Aventis) |
| | TXD 258 (Aventis) |
| | epothilone B (Novartis) |
| | T 900607 (Tularik) |
| | T 138067 (Tularik) |
| | cryptophycin 52 (Eli Lilly) |
| | vinflunine (Fabre) |
| | auristatin PE (Teikoku Hormone) |
| | BMS 247550 (BMS) |
| | BMS 184476 (BMS) |
| | BMS 188797 (BMS) |
| | taxoprexin (Protarga) |
| | SB 408075 (GlaxoSmithKline) |
| | Vinorelbine |
| | Trichostatin A |
| | E7010 (Abbott) |
| | PG-TXL (Cell Therapeutics) |
| | IDN 5109 (Bayer) |
| | A 105972 (Abbott) |
| | A 204197 (Abbott) |
| | LU 223651 (BASF) |
| | D 24851 (ASTAMedica) |
| | ER-86526 (Eisai) |
| | combretastatin A4 (BMS) |
| | isohomohalichondrin-B (PharmaMar) |
| | ZD 6126 (AstraZeneca) |
| | AZ10992 (Asahi) |
| | IDN-5109 (Indena) |
| | AVLB (Prescient NeuroPharma) |
| | azaepothilone B (BMS) |
| | BNP-7787 (BioNumerik) |
| | CA-4 prodrug (OXiGENE) |
| | dolastatin-10 (NIH) |
| | CA-4 (OXiGENE) |
| | docetaxel |
| | vincristine |
| | paclitaxel |
| Aromatase inhibitors | aminoglutethimide |
| | atamestane (BioMedicines) |
| | letrozole |
| | anastrazole |
| | YM-511 (Yamanouchi) |
| | formestane |
| | exemestane |
| Thymidylate synthase inhibitors | pemetrexed (Eli Lilly) |
| | ZD-9331 (BTG) |
| | nolatrexed (Eximias) |
| | CoFactor ™ (BioKeys) |
| DNA antagonists | trabectedin (PharmaMar) |
| | glufosfamide (Baxter International) |
| | albumin + 32P (Isotope Solutions) |
| | thymectacin (NewBiotics) |
| | edotreotide (Novartis) |
| | mafosfamide (Baxter International) |
| | apaziquone (Spectrum Pharmaceuticals) |
| | O6 benzyl guanine (Paligent) |
| Farnesyltransferase inhibitors | arglabin (NuOncology Labs) |
| | lonafarnib (Schering-Plough) |
| | BAY-43-9006 (Bayer) |
| | tipifarnib (Johnson & Johnson) |
| | perillyl alcohol (DOR BioPharma) |

TABLE 9-continued

| | |
|---|---|
| Pump inhibitors | CBT-1 (CBA Pharma) |
| | tariquidar (Xenova) |
| | MS-209 (Schering AG) |
| | zosuquidar trihydrochloride (Eli Lilly) |
| | biricodar dicitrate (Vertex) |
| Histone acetyltransferase inhibitors | tacedinaline (Pfizer) |
| | SAHA (Aton Pharma) |
| | MS-275 (Schering AG) |
| | pivaloyloxymethyl butyrate (Titan) |
| | depsipeptide (Fujisawa) |
| Metalloproteinase inhibitors | Neovastat (Aeterna Laboratories) |
| | marimastat (British Biotech) |
| | CMT-3 (CollaGenex) |
| | BMS-275291 (Celltech) |
| Ribonucleoside reductase inhibitors | gallium maltolate (Titan) |
| | triapine (Vion) |
| | tezacitabine (Aventis) |
| | didox (Molecules for Health) |
| TNF alpha agonists/antagonists | virulizin (Lorus Therapeutics) |
| | CDC-394 (Celgene) |
| | revimid (Celgene) |
| Endothelin A receptor antagonist | atrasentan (Abbott) |
| | ZD-4054 (AstraZeneca) |
| | YM-598 (Yamanouchi) |
| Retinoic acid receptor agonists | fenretinide (Johnson & Johnson) |
| | LGD-1550 (Ligand) |
| | alitretinoin (Ligand) |
| Immuno-modulators | interferon |
| | oncophage (Antigenics) |
| | GMK (Progenics) |
| | adenocarcinoma vaccine (Biomira) |
| | CTP-37 (AVI BioPharma) |
| | IRX-2 (Immuno-Rx) |
| | PEP-005 (Peplin Biotech) |
| | synchrovax vaccines (CTL Immuno) |
| | melanoma vaccine (CTL Immuno) |
| | p21 RAS vaccine (GemVax) |
| | MAGE-A3 (GSK) |
| | nivolumab (BMS) |
| | abatacept (BMS) |
| | pembrolizumab |
| | avelumab |
| | CTL019 |
| | MIW815 |
| | MCS-110 |
| | Anti-IL6 |
| | Anti-LAG3 |
| | Anti-PD1 |
| | Anti-TIM3 |
| | Anti-VISTA |
| | TLR7/8 dual agonist |
| | TReg inhibitors |
| | Anti-OX40 |
| | Anti-SLAMF7 |
| | Anti-CD40 |
| | Anti-CD47 |
| | Anti-CSF-1R |
| | Anti-KIR |
| | Anti-NKG2A |
| | STING agonists |
| | dexosome therapy (Anosys) |
| | pentrix (Australian Cancer Technology) |
| | ISF-154 (Tragen) |
| | cancer vaccine (Intercell) |
| | norelin (Biostar) |
| | BLP-25 (Biomira) |
| | MGV (Progenics) |
| | β-alethine (Dovetail) |
| | CLL therapy (Vasogen) |
| | Ipilimumab (BMS), |
| | CM-10 (cCam Biotherapeutics) |
| | MPDL3280A (Genentech) |
| | MEDI4736 |
| | PDR001 |
| | LAG525 |
| | CAR-T therapies |
| | Anti-CD73 |
| | Anti-CTLA4 |
| | Anti-IL10 |
| | Anti-PDL1 |
| | Anti-TIGIT |
| | STAT3 inhibitors |
| | TGF beta inhibitors |
| | Anti-CD137 (4-1BB) |
| | Anti-GITR |
| | A2aR antagonist |
| | Anti-CCR2 |
| | Anti-CCR4 |
| | Anti-CXCR2 |
| | Anti-CXCR4 |
| | IDO/TDO inhibitors |
| Hormonal and antihormonal agents | estrogens |
| | conjugated estrogens |
| | ethinyl estradiol |
| | chlortrianisen |
| | idenestrol |
| | hydroxyprogesterone caproate |
| | medroxyprogesterone |
| | testosterone |
| | testosterone propionate; |
| | fluoxymesterone |
| | methyltestosterone |
| | diethylstilbestrol |
| | megestrol |
| | bicalutamide |
| | flutamide |
| | nilutamide |
| | dexamethasone |
| | prednisone |
| | methylprednisolone |
| | prednisolone |
| | aminoglutethimide |
| | leuprolide |
| | octreotide |
| | mitotane |
| | P-04 (Novogen) |
| | 2-methoxyestradiol (EntreMed) |
| | arzoxifene (Eli Lilly) |
| | tamoxifen |
| | toremofine |
| | goserelin |
| | Leuporelin |
| | bicalutamide |
| Photodynamic agents | talaporfin (Light Sciences) |
| | Theralux (Theratechnologies) |
| | motexafin gadolinium (Pharmacyclics) |
| | Pd-bacteriopheophorbide (Yeda) |
| | lutetium texaphyrin (Pharmacyclics) |
| | hypericin |
| Kinase Inhibitors | imatinib (Novartis) |
| | leflunomide (Sugen/Pharmacia) |
| | ZD1839 (AstraZeneca) |
| | erlotinib (Oncogene Science) |
| | canertinib (Pfizer) |
| | squalamine (Genaera) |
| | SU5416 (Pharmacia) |
| | SU6668 (Pharmacia) |
| | ZD4190 (AstraZeneca) |
| | ZD6474 (AstraZeneca) |
| | vatalanib (Novartis) |
| | PKI166 (Novartis) |
| | GW2016 (GlaxoSmithKline) |
| | EKB-509 (Wyeth) |
| | trastuzumab (Genentech) |
| | OSI-774 (Tarceva ™) |
| | CI-1033 (Pfizer) |
| | SU11248 (Pharmacia) |
| | RH3 (York Medical) |
| | Genistein |
| | Radicinol |
| | Met-MAb (Roche) |
| | SR-27897 (CCK A inhibitor, Sanofi-Synthelabo) |
| | tocladesine (cyclic AMP agonist, Ribapharm) |
| | alvocidib (CDK inhibitor, Aventis) |
| | CV-247 (COX-2 inhibitor, Ivy Medical) |
| | P54 (COX-2 inhibitor, Phytopharm) |
| | CapCell ™ (CYP450 stimulant, Bavarian Nordic) |
| | GCS-100 (gal3 antagonist, GlycoGenesys) |
| | G17DT immunogen (gastrin inhibitor, Aphton) |
| | efaproxiral (oxygenator, Allos Therapeutics) |

TABLE 9-continued

PI-88 (heparanase inhibitor, Progen)
tesmilifene (histamine antagonist, YM BioSciences)
histamine (histamine H2 receptor agonist, Maxim)
tiazofurin (IMPDH inhibitor, Ribapharm)
cilengitide (integrin antagonist, Merck KGaA)
SR-31747 (IL-1 antagonist, Sanofi-Synthelabo)
CCI-779 (mTOR kinase inhibitor, Wyeth)
exisulind (PDE V inhibitor, Cell Pathways)
dabrafenib
midostaurin (PKC inhibitor, Novartis)
bryostatin-1 (PKC stimulant, GPC Biotech)
CDA-II (apoptosis promotor, Everlife)
SDX-101 (apoptosis promotor, Salmedix)
rituximab (CD20 antibody, Genentech
carmustine
Mitoxantrone
Bleomycin
CP-461 (PDE V inhibitor, Cell Pathways)
AG-2037 (GART inhibitor, Pfizer)
WX-UK1 (plasminogen activator inhibitor, Wilex)
PBI-1402 (PMN stimulant, ProMetic LifeSciences)
bortezomib (proteasome inhibitor, Millennium)
SRL-172 (T cell stimulant, SR Pharma)
TLK-286 (glutathione S transferase inhibitor, Telik)
PT-100 (growth factor agonist, Point Therapeutics)
Chrysophanic acid
Cesium oxides
BRAF inhibitors,
PDL1 inhibitors
MEK inhibitors
bevacizumab
angiogenesis inhibitors
Absinthin
EKB-569 (Wyeth)
kahalide F (PharmaMar)
CEP-701 (Cephalon)
CEP-751 (Cephalon)
MLN518 (Millenium)
PKC412 (Novartis)
Phenoxodiol (Novogen)
C225 (ImClone)
rhu-Mab (Genentech)
MDX-H210 (Medarex)
2C4 (Genentech)
MDX-447 (Medarex)
ABX-EGF (Abgenix)
IMC-1C11 (ImClone)
Tyrphostins
Gefitinib (Iressa)
PTK787 (Novartis)
EMD 72000 (Merck)
Emodin
Radicinol
Vemurafenib (B-Raf enzyme inhibitor, Daiichi Sankyo)
ceflatonin (apoptosis promotor, ChemGenex)
BCX-1777 (PNP inhibitor, BioCryst)
ranpirnase (ribonuclease stimulant, Alfacell)
galarubicin (RNA synthesis inhibitor, Dong-A)
tirapazamine (reducing agent, SRI International)
N-acetylcysteine (reducing agent, Zambon)
R-flurbiprofen (NF-kappaB inhibitor, Encore)
3CPA (NF-kappaB inhibitor, Active Biotech)
seocalcitol (vitamin D receptor agonist, Leo)
131-I-TM-601 (DNA antagonist, TransMolecular)
eflornithine (ODC inhibitor, ILEX Oncology)
minodronic acid (osteoclast inhibitor, Yamanouchi)
indisulam (p53 stimulant, Eisai)
aplidine (PPT inhibitor, PharmaMar)
CRS-207
CHS-828 (cytotoxic agent, Leo)
trans-retinoic acid (differentiator, NIH)
MX6 (apoptosis promotor, MAXIA)
apomine (apoptosis promotor, ILEX Oncology)
sorafenib
BRAF inhibitors
urocidin (apoptosis promotor, Bioniche)
Ro-31-7453 (apoptosis promotor, La Roche)
gemtuzumab (CD33 antibody, Wyeth Ayerst)
PG2 (hematopoiesis enhancer, Pharmagenesis)

TABLE 9-continued

Immunol ™ (triclosan oral rinse, Endo)
triacetyluridine (uridine prodrug, Wellstat)
SN-4071 (sarcoma agent, Signature BioScience)
TransMID-107 ™ (immunotoxin, KS Biomedix)
PCK-3145 (apoptosis promotor, Procyon)
doranidazole (apoptosis promotor, Pola)
cafestol
kahweol
caffeic acid
Tyrphostin AG
PD-1 inhibitors
CTLA-4 inhibitors
brostallicin (apoptosis promotor, Pharmacia)
β-lapachone
gelonin

EXAMPLES

General Methods

Differential Scanning Calorimetry

Differential Scanning calorimetry (DCS) data were collected using a TA Instruments Q10 DSC. Typically, samples (2-8 mg) were placed in unsealed, but covered hermetic alodined aluminum sample pans and scanned from 30 to 300° C. at a rate of 10° C./min using a nitrogen purge of 50 mL/min.

Thermal Gravimetric Analysis

Thermal Gravimetric Analysis (TGA) data were collected using a TA Instruments TGA Q500. Typically, samples (~10 mg) were placed in an open, pre-tared aluminum sample pan and scanned from 25 to 300° C. at a rate of 10° C./min using a nitrogen purge at 60 mL/min.

X-Ray Powder Diffractometer

X-ray powder diffraction patterns were obtained using a Bruker D8 Advance equipped with a Cu Kα radiation source (A=1.54° Å), a 9-position sample holder and a LYNXEYE super speed detector.

Samples were placed on zero-background, silicon plate holders.

Dynamic Vapor Sorption

Samples were analyzed using an Aquadyne DVS-2 gravimetric water sorption analyzer. The relative humidity was adjusted between 2-95% and the weight of the sample was continuously monitored and recorded.

Proton-Nuclear Magnetic Resonance

Sample was prepared by dissolving the compound in deuterated dimethylsulfoxide with 0.05% (v/v) tetramethylsilane (TMS). Spectra were collected at ambient temperature on a Bruker Avance 300 MHz NMR with TopSpin software. The number of scans was 16 for proton NMR.

Karl Fischer

The apparent water content in samples was determined by Karl Fischer titration using a Mettler Toledo DL39 Coulometric KF Titrator. HYDRANAL-Coulomat AD was used as the titrant. About 20 mg of the solid was used for titration. The analytical parameters are presented in Table 10.

TABLE 10

Karl Fischer parameters

| KF Parameter | Value |
| --- | --- |
| Speed [%] | 40 |
| Mix time [sec] | 10 |
| Auto start | No |
| Blank [µg] | 0 |

TABLE 10-continued

| Karl Fischer parameters | |
|---|---|
| KF Parameter | Value |
| Drift [µg/min] | 5 |
| Calculation | Ug |
| Standby | Yes |
| Initial drift [µg/min] | <10 |
| Initial Potential [mV] | 100 |

Optical Microscopy

Samples were analyzed using an Olympus BX53 polarized light microscope equipped with a PAXcam 3 digital microscope camera.

Example 1. Profiling of Solid-State β-GPA

Figure 2:
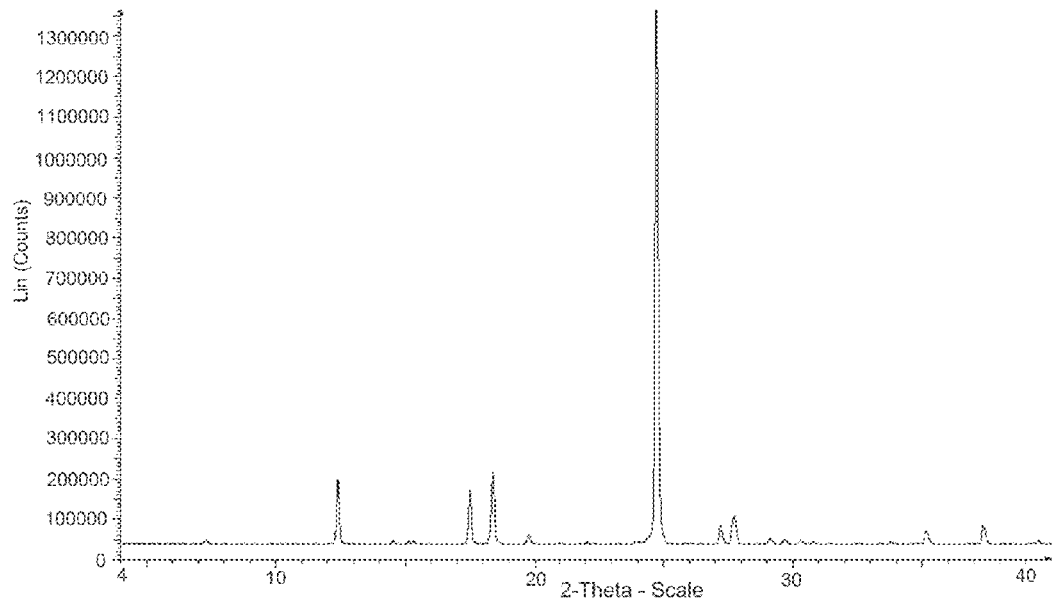
FIG. 2 is an image depicting X-ray powder diffraction (XRPD) pattern obtained for a crystalline form of β-GPA.
Figure 3:
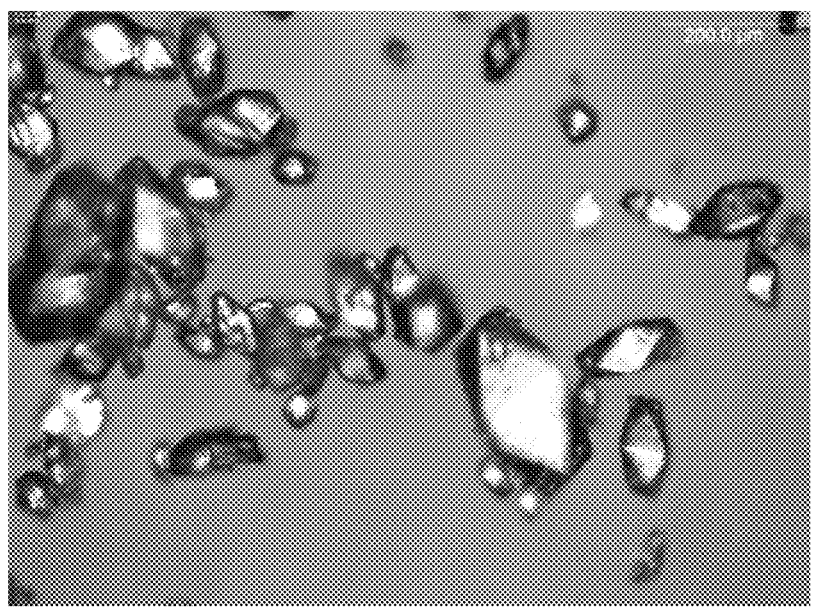
FIG. 3 is an image of β-GPA crystals under a polarized microscope.
Figure 4:
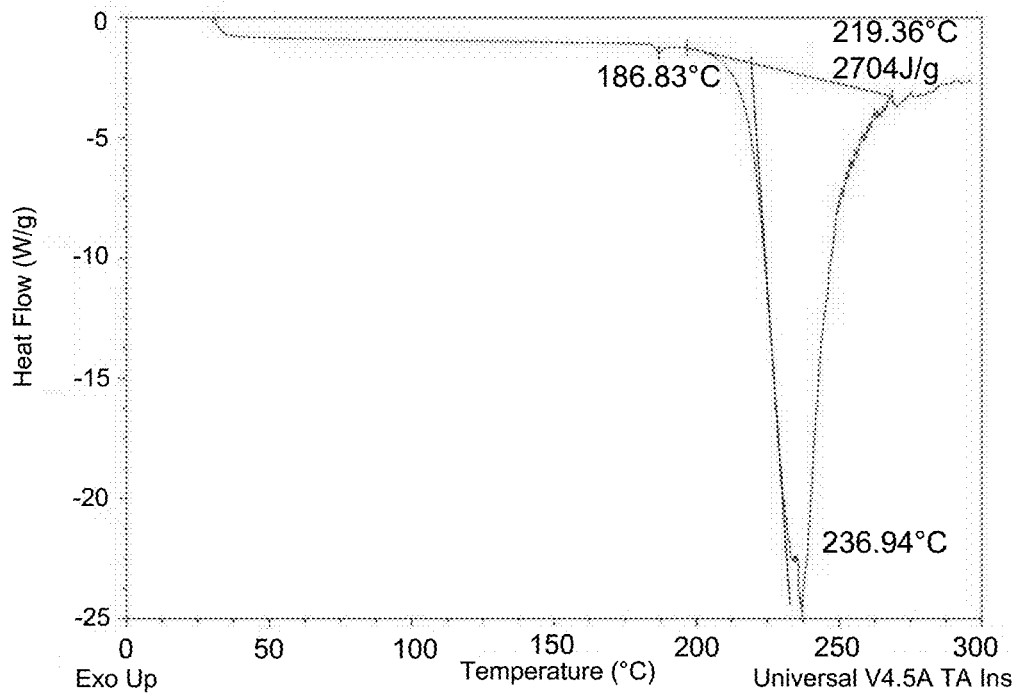
FIG. 4 is an image depicting a DSC thermogram obtained for a crystalline form of β-GPA.

Solid-state β-GPA was analyzed by XRPD (FIG. 2) and was also observed under a polarized microscope (FIG. 3). The material was found to be crystalline A DSC thermogram of β-GPA is illustrated in FIG. 4. The melting onset of β-GPA was found to be around 219° C. followed by an endothermic event at around 237° C. and immediate possible degradation. However, another tiny endothermic event at 187° C. was also exhibited by the material (possible traces of another form of β-GPA).

Figure 5:
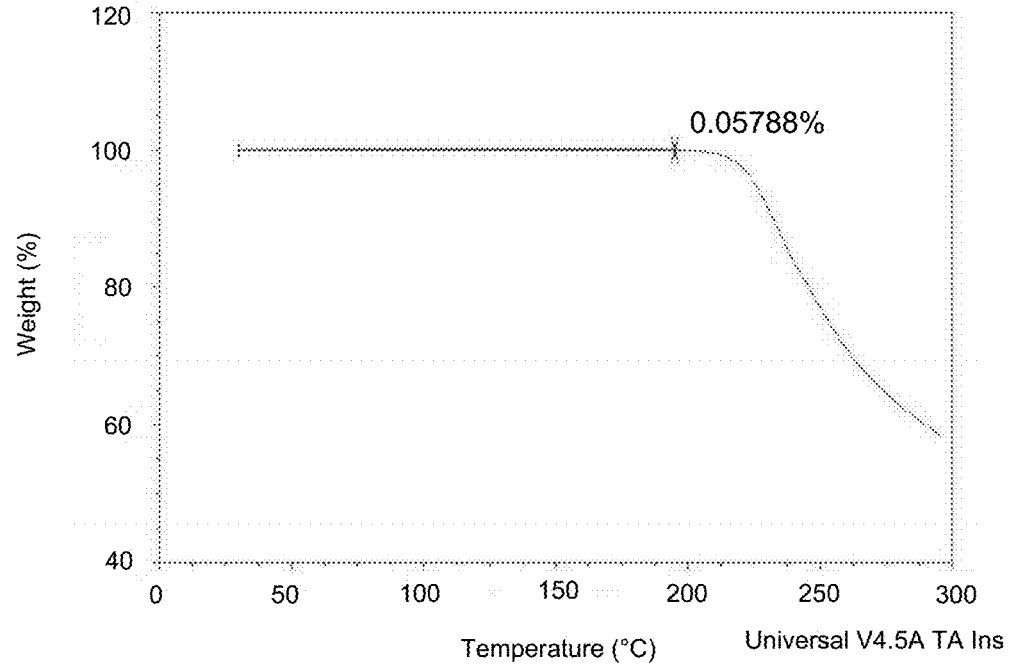
FIG. 5 is an image depicting TGA analysis obtained for a crystalline form of β-GPA.

TGA analysis reveals that there is less than 0.1% weight loss in the sample from 30 to 145° C. as illustrated in FIG. 5.

Figure 6:
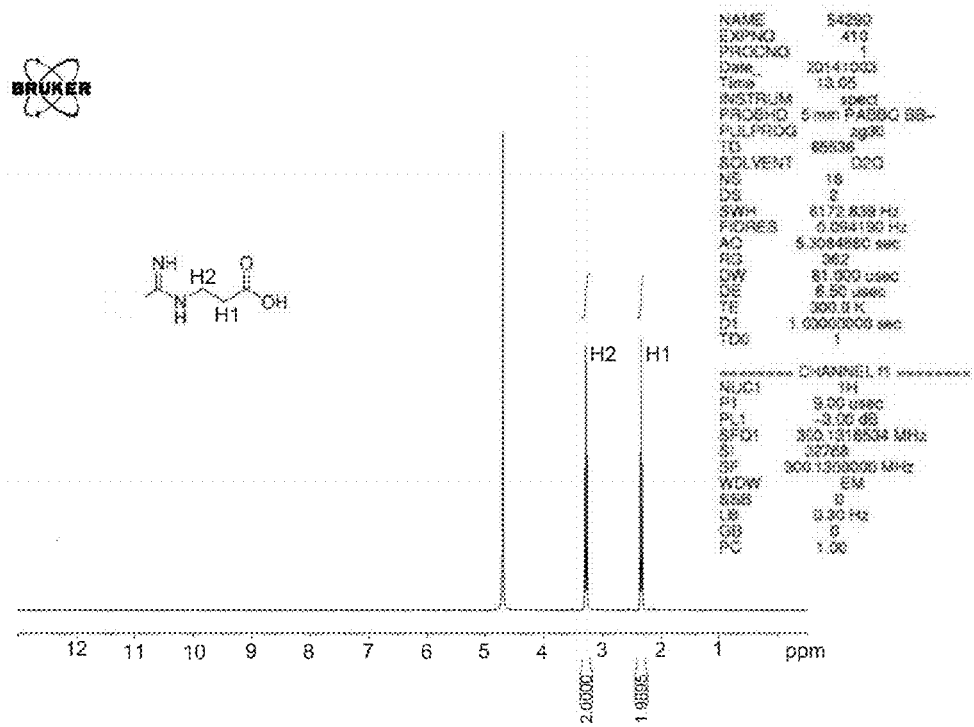
FIG. 6 is an image depicting a $^1$H NMR spectra of a crystalline form β-GPA.

The $^1$H NMR of β-GPA is shown in FIG. 6.

Figure 7:
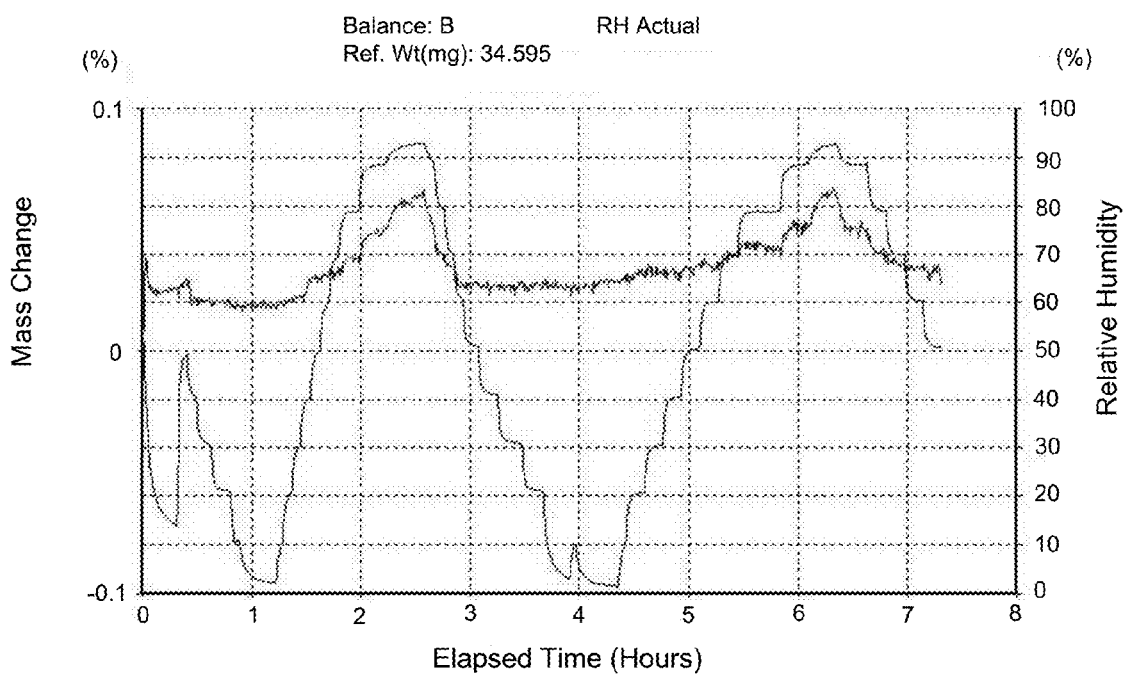
FIG. 7 is an image depicting a DVS analysis for a crystalline form of β-GPA.
Figure 8:
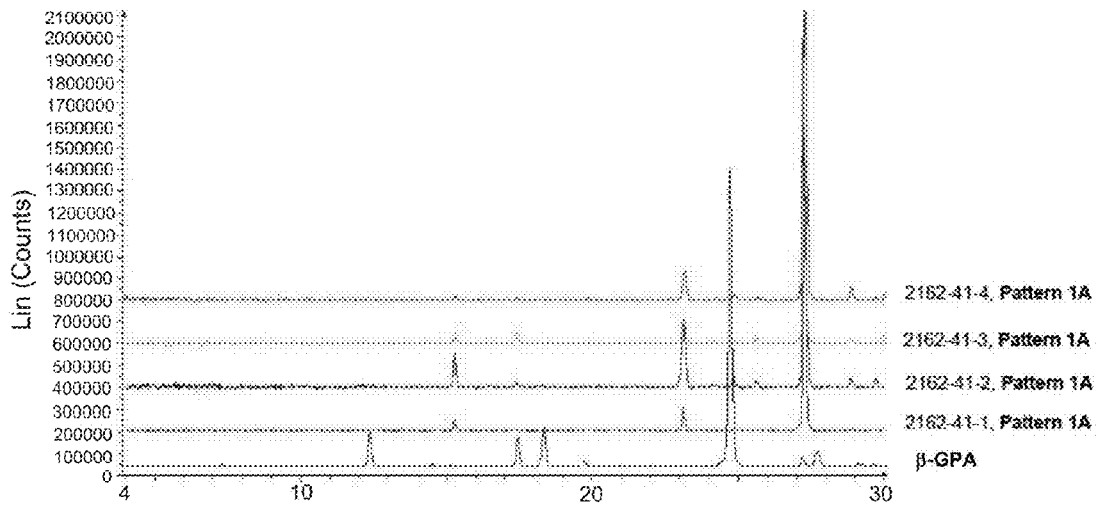
FIG. 8 is an image depicting X-ray powder diffraction (XRPD) pattern obtained for a crystalline form of the 1:1 hydrochloride salt of β-GPA.
Figure 9:
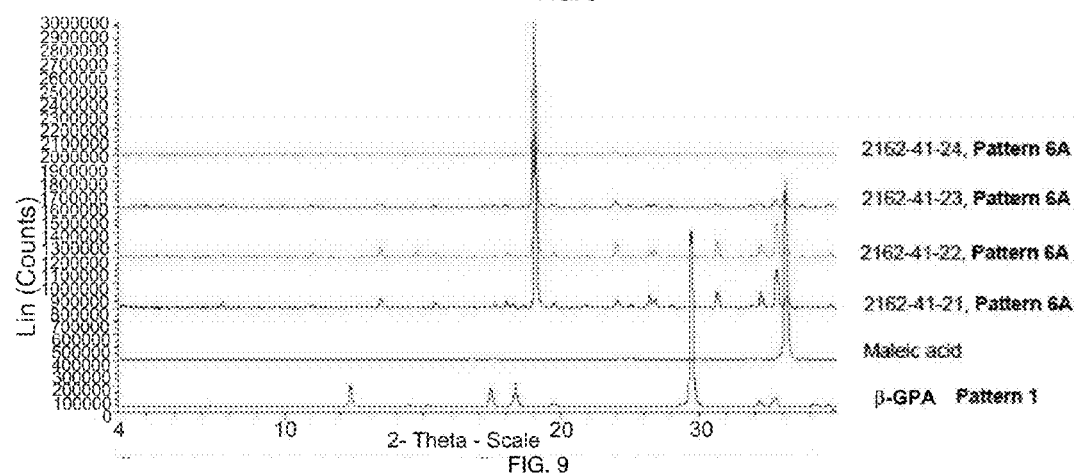
FIG. 9 is an image depicting X-ray powder diffraction (XRPD) pattern obtained for a crystalline form of the 1:1 maleate salt of β-GPA.
Figure 10:
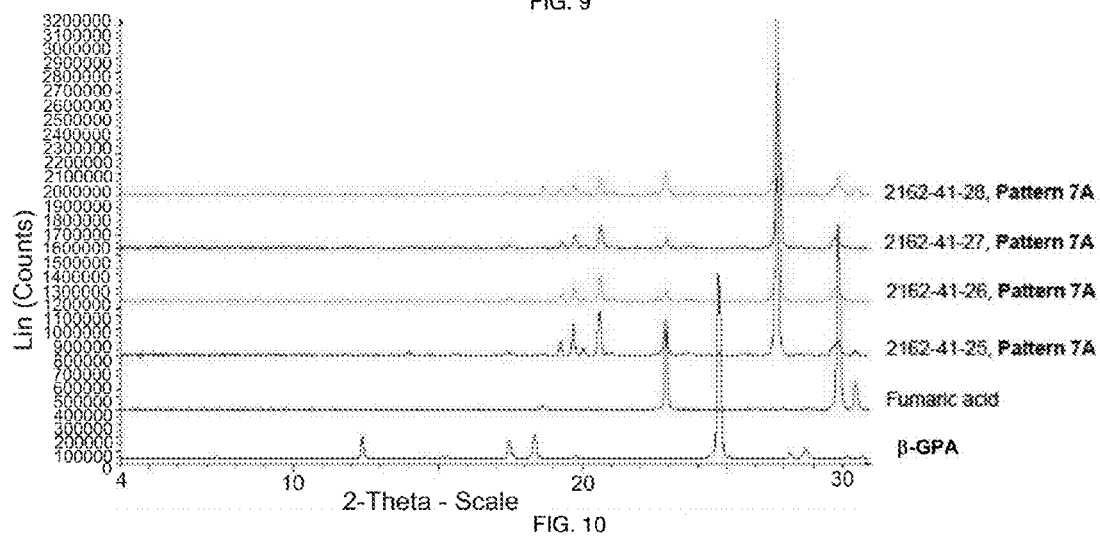
FIG. 10 is an image depicting X-ray powder diffraction (XRPD) pattern obtained for a crystalline form of the 1:1 fumarate salt of β-GPA.
Figure 11:
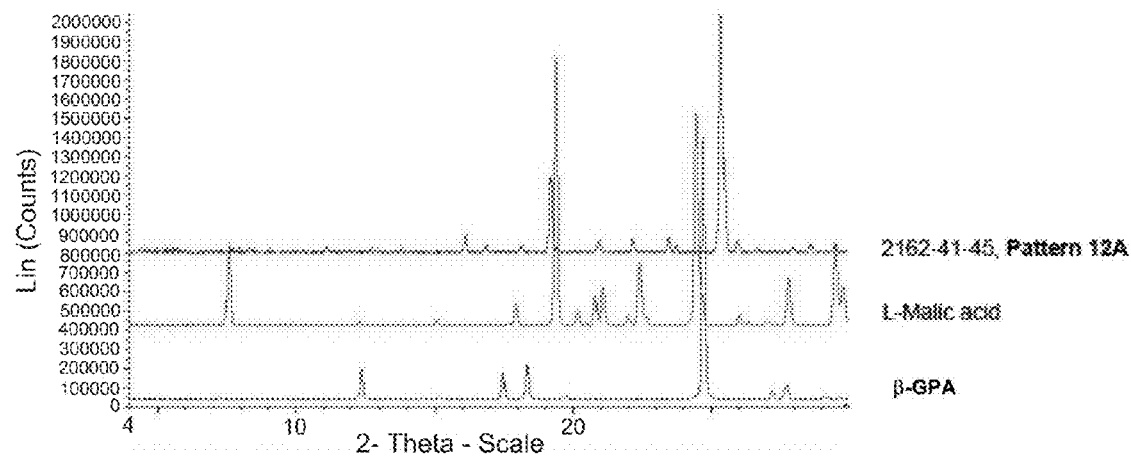
FIG. 11 is an image depicting X-ray powder diffraction (XRPD) pattern obtained for a crystalline form of the 1:1 L-malic acid salt of β-GPA.
Figure 12:
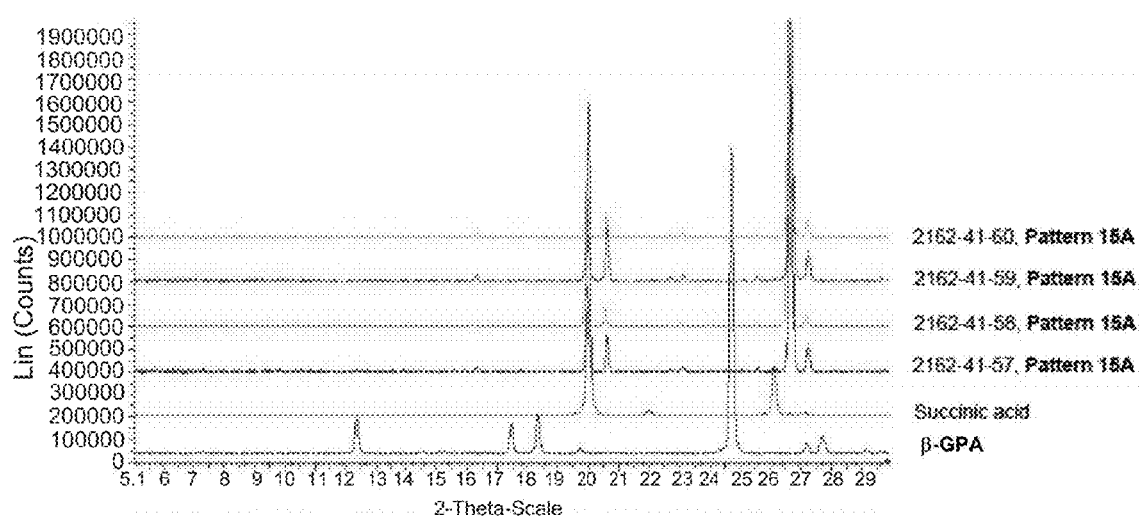
FIG. 12 is an image depicting X-ray powder diffraction (XRPD) pattern obtained for a crystalline form of the 2:1 succinate salt of β-GPA.
Figure 13:
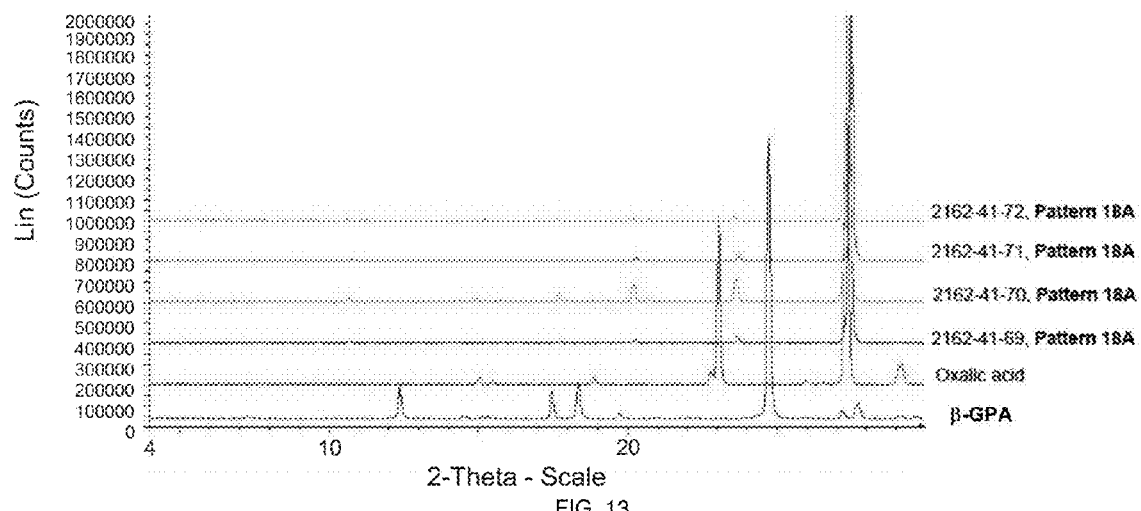
FIG. 13 is an image depicting X-ray powder diffraction (XRPD) pattern obtained for a crystalline form of the 1:1 oxalate salt of β-GPA.

The DVS experiment of β-GPA revealed around 0.1% moisture absorbed and desorbed when exposed to relative humidity between 0-95 percent (FIG. 7). No change in the solid form was observed after the DVS experiment as confirmed by XRPD.

Example 2. Salt Screening

Stage I

Table 11 illustrates the selected counter ions for the salt screening of β-GPA. Salt screening experiments were designed in 1:1.1 equivalence (eq) for β-GPA to counter ion.

TABLE 11

| List of selected counterions | | | | |
|---|---|---|---|---|
| Sample ID | β-GPA (mg) | Counterion | Counterion sequence # | Counterion molecular wt |
| 2162-42-1 to 4 | 30 | Hydrochloric acid (36-38%)* | 1 | 36.46 |
| 2162-42-5 to 8 | 30 | Hydrobromic acid (48%)* | 2 | 80.91 |
| 2162-42-9 to 12 | 30 | Sulfuric acid (95-98%)* | 3 | 98.08 |
| 2162-42-13 to 16 | 30 | Phosphoric acid (85%)* | 4 | 98.00 |
| 2162-42-17 to 20 | 30 | Methane sulfonic acid (98%)* | 5 | 96.11 |
| 2162-42-21 to 24 | 30 | Maleic acid | 6 | 116.07 |
| 2162-42-25 to 28 | 30 | Fumaric acid | 7 | 116.07 |
| 2162-42-29 to 32 | 30 | Tartaric acid | 8 | 150.09 |
| 2162-42-33 to 36 | 30 | Ethanesulfonic acid | 9 | 110.13 |
| 2162-42-37 to 40 | 30 | Ethanedisulfonic acid | 10 | 190.20 |
| 2162-42-41 to 44 | 30 | Citric acid | 11 | 192.12 |
| 2162-42-45 to 48 | 30 | Malic acid | 12 | 134.09 |
| 2162-42-49 to 52 | 30 | Lactic acid | 13 | 90.08 |
| 2162-42-53 to 56 | 30 | Aspartic acid | 14 | 133.1 |
| 2162-42-57 to 60 | 30 | Succinic acid | 15 | 118.09 |
| 2162-42-61 to 64 | 30 | Sodium hydroxide | 16 | 40.00 |
| 2162-42-65 to 68 | 30 | Potassium hydroxide | 17 | 56.11 |
| 2162-42-69 to 72 | 30 | Oxalic acid | 18 | 90.03 |
| 2162-45-1 to 4 | 30 | Magnesium hydroxide | 19 | 58.32 |

76 salt screening experiments of β-GPA with 19 different counter ions were set up with 30 mg of β-GPA. Sets of four vials for each counterion were set up with four different solvents (0.3 mL): ethanol:water (9:1), isopropanol, acetone:water (9:1) and acetonitrile.

Appropriate amounts of β-GPA and the counterion were dissolved in the respective solvents and heated to 70-75° C. until dissolved. An additional 0.1 mL of water was added to the samples containing isopropanol, acetone:water (9:1) and acetonitrile. To samples containing L-aspartic acid, around 1.5 mL of water was required to dissolve the solids. After a clear solution was obtained, the samples were left for stirring at room temperature. Solids were observed in the following samples: 2163-42-4, 25, 26, 27, 28, 45 and 53 through 75. The solids were filtered and analyzed by XRPD immediately as wet sample. The samples that did not yield solids were placed in the oven at 50° C. for drying. The following samples resulted in solids after overnight drying: 2162-42-2, 1, 2, 3 and 21 through 24. The experiments with L-aspartic acid, sodium hydroxide, potassium hydroxide, and magnesium hydroxide resulted in the precipitation of either β-GPA or the counterion. All the experimental observations were recorded after every step and are listed in Table 12.

TABLE 12

| Results of Salt screening | | | | | |
|---|---|---|---|---|---|
| Sample ID | Counterion | Solvent | After 24 hours | After Drying | XRPD |
| 2162-42-1 | Hydrochloric Acid | EtOH:H$_2$O (9:1) | Clear Solution | White Solid | Pattern 1A |
| 2162-42-2 | | IPA | Clear Solution | White Solid | |
| 2162-42-3 | | Acetone:H$_2$O (9:1) | Clear Solution | White Solid | |
| 2162-42-4 | | MeCN | White Solid | N/A | |
| 2162-42-5 | Hydrobromic Acid | EtOH:H$_2$O (9:1) | Clear Solution | Gel | N/A |
| 2162-42-6 | | IPA | Clear Solution | Gel | N/A |
| 2162-42-7 | | Acetone:H$_2$O (9:1) | Clear Solution | Gel | N/A |

TABLE 12-continued

Results of Salt screening

| Sample ID | Counterion | Solvent | After 24 hours | After Drying | XRPD |
|---|---|---|---|---|---|
| 2162-42-8 | Sulfuric Acid | MeCN | Clear Solution | Gel | N/A |
| 2162-42-9 | | EtOH:H$_2$O (9:1) | Clear Solution | Gel | N/A |
| 2162-42-10 | | IPA | Clear Solution | Gel | N/A |
| 2162-42-11 | | Acetone:H$_2$O (9:1) | Clear Solution | Gel | N/A |
| 2162-42-12 | | MeCN | Clear Solution | Gel | N/A |
| 2162-42-13 | Phosphoric Acid | EtOH:H$_2$O (9:1) | Clear Solution | Gel | N/A |
| 2162-42-14 | | IPA | Clear Solution | Gel | N/A |
| 2162-42-15 | | Acetone:H$_2$O (9:1) | Clear Solution | Gel | N/A |
| 2162-42-16 | | MeCN | Clear Solution | Gel | N/A |
| 2162-42-17 | Methanesulfonic Acid | EtOH:H$_2$O (9:1) | Clear Solution | Gel | N/A |
| 2162-42-18 | | IPA | Clear Solution | Gel | N/A |
| 2162-42-19 | | Acetone:H$_2$O (9:1) | Clear Solution | Gel | N/A |
| 2162-42-20 | | MeCN | Clear Solution | Gel | N/A |
| 2162-42-21 | Maleic Acid | EtOH:H$_2$O (9:1) | Clear Solution | White Solid | Pattern 6A |
| 2162-42-22 | | IPA | Clear Solution | White Solid | |
| 2162-42-23 | | Acetone:H$_2$O (9:1) | Clear Solution | White Solid | |
| 2162-42-24 | | MeCN | Clear Solution | White Solid | |
| 2162-42-25 | Fumaric Acid | EtOH:H$_2$O (9:1) | White Solid | N/A | Pattern 7A |
| 2162-42-26 | | IPA | White Solid | N/A | |
| 2162-42-27 | | Acetone:H$_2$O (9:1) | White Solid | N/A | |
| 2162-42-28 | | MeCN | White Solid | N/A | |
| 2162-42-29 | L-Tartaric Acid | EtOH:H$_2$O (9:1) | Clear Solution | Gel | N/A |
| 2162-42-30 | | IPA | Clear Solution | Gel | N/A |
| 2162-42-31 | | Acetone:H$_2$O (9:1) | Clear Solution | Gel | N/A |
| 2162-42-32 | | MeCN | Clear Solution | Gel | N/A |
| 2162-42-33 | Ethanesulfonic Acid | EtOH:H$_2$O (9:1) | Clear Solution | Gel | N/A |
| 2162-42-34 | | IPA | Clear Solution | Gel | N/A |
| 2162-42-35 | | Acetone:H$_2$O (9:1) | Clear Solution | Gel | N/A |
| 2162-42-36 | | MeCN | Clear Solution | Gel | N/A |
| 2162-42-37 | Ethanedisulfonic Acid | EtOH:H$_2$O (9:1) | Clear Solution | Gel | N/A |
| 2162-42-38 | | IPA | Clear Solution | Gel | N/A |
| 2162-42-39 | | Acetone:H$_2$O (9:1) | Clear Solution | Gel | N/A |
| 2162-42-40 | | MeCN | Clear Solution | Gel | N/A |
| 2162-42-41 | Citric Acid | EtOH:H$_2$O (9:1) | Clear Solution | Gel | N/A |
| 2162-42-42 | | IPA | Clear Solution | Gel | N/A |
| 2162-42-43 | | Acetone:H$_2$O (9:1) | Clear Solution | Gel | N/A |
| 2162-42-44 | | MeCN | Clear Solution | Gel | N/A |
| 2162-42-45 | L-Malic Acid | EtOH:H$_2$O (9:1) | White Solid | N/A | Pattern 12A |
| 2162-42-46 | | IPA | Clear Solution | Gel | N/A |
| 2162-42-47 | | Acetone:H$_2$O (9:1) | Clear Solution | Gel | N/A |
| 2162-42-48 | | MeCN | Clear Solution | Gel | N/A |
| 2162-42-49 | L-Latic Acid | EtOH:H$_2$O (9:1) | Clear Solution | Gel | N/A |
| 2162-42-50 | | IPA | Clear Solution | Gel | N/A |
| 2162-42-51 | | Acetone:H$_2$O (9:1) | Clear Solution | Gel | N/A |
| 2162-42-52 | | MeCN | Clear Solution | Gel | N/A |
| 2162-42-53 | L-Aspartic Acid | EtOH:H$_2$O (9:1) | White Solid | N/A | L-Aspartic Acid |
| 2162-42-54 | | IPA | White Solid | N/A | |
| 2162-42-55 | | Acetone:H$_2$O (9:1) | White Solid | N/A | |
| 2162-42-56 | | MeCN | White Solid | N/A | |
| 2162-42-57 | Succinic Acid | EtOH:H$_2$O (9:1) | White Solid | N/A | Pattern 15A |
| 2162-42-58 | | IPA | White Solid | N/A | |
| 2162-42-59 | | Acetone:H$_2$O (9:1) | White Solid | N/A | |
| 2162-42-60 | | MeCN | White Solid | N/A | |
| 2162-42-61 | Sodium Hydroxide | EtOH:H$_2$O (9:1) | White Solid | N/A | β-GPA |
| 2162-42-62 | | IPA | White Solid | N/A | |
| 2162-42-63 | | Acetone:H$_2$O (9:1) | White Solid | N/A | |
| 2162-42-64 | | MeCN | White Solid | N/A | |
| 2162-42-65 | Potassium Hydroxide | EtOH:H$_2$O (9:1) | White Solid | N/A | β-GPA |
| 2162-42-66 | | IPA | White Solid | N/A | |
| 2162-42-67 | | Acetone:H$_2$O (9:1) | White Solid | N/A | |
| 2162-42-68 | | MeCN | White Solid | N/A | |
| 2162-42-69 | Oxalic Acid | EtOH:H$_2$O (9:1) | White Solid | N/A | Pattern 18A |
| 2162-42-70 | | IPA | White Solid | N/A | |
| 2162-42-71 | | Acetone:H$_2$O (9:1) | White Solid | N/A | |
| 2162-42-72 | | MeCN | White Solid | N/A | |
| 2162-45-1 | Magnesium Hydroxide | EtOH:H$_2$O (9:1) | White Solid | N/A | β-GPA |
| 2162-45-2 | | IPA | White Solid | N/A | |
| 2162-45-3 | | Acetone:H$_2$O (9:1) | White Solid | N/A | |
| 2162-45-4 | | MeCN | White Solid | N/A | |

EtOH = ethanol; IPA = isopropanol; MeCN = acetonitrile

FIGS. 8 through 13 represents the XRPDs of the new crystalline forms isolated from slurry/slow evaporation experiments.

Stage II

The samples that resulted in gels in Stage I of the salt screening experiments were considered for Stage II, where another set of four new solvent systems (methanol, water, ethyl acetate, and trifluoroethanol) were used. The gels were dissolved in the respective solvents (Table 11) at 70° C. and were allowed to stir overnight. If a precipitate was observed the following day the stirring was stopped and XRPD analysis was carried out on the samples. If there was no precipitation, then the samples were dried in the oven at 50° C. Three experiments, hydrobromic acid in methanol and ethyl acetate and L-lactic acid in methanol, resulted in the precipitation β-GPA as confirmed by XRPD analysis. Crystalline forms were prepared with phosphoric acid (from ethyl acetate and trifluoroethanol), methanesulfonic acid (from ethyl acetate), ethanesulfonic acid (from all four solvents), and L-malic acid (from trifluoroethanol).

Example 3. Salt Screening Experiments in 2:1 (β-GPA:Acid) Molar Ratio

Salt screening experiments of β-GPA with maleic, fumaric, and oxalic acids in 2:1 (β-GPA:acid) ratio were set up. Around 0.3 mL of water was used to dissolve β-GPA (120 mg) and the counterion in 2:1 (β-GPA:acid) ratio at 90° C. for oxalic and maleic acid. However, for the experiment with fumaric acid, 0.2 mL of methanol was used to dissolve the counterion at 65° C. All the experiments resulted in the precipitation of white solids within 10 minutes. However, the vials were left for stirring over the weekend. Solids were filtered and rinsed with around 0.5 mL of isopropanol during filtration followed by XRPD analysis. Results are tabulated in Table 13.

TABLE 13

Results of Salt Screening Experiments in 2:1 (β-GPA:acid) molar ratio

| Sample ID | Counterion | Ratio of β-GPA to counterion | Solvent(s) used | Result |
|---|---|---|---|---|
| 2162-48-4 | Fumaric acid | 2:1 | 0.3 mL H₂O to dissolve β-GPA + 0.2 mL methanol to dissolve fumaric acid | 1:1 salt was formed (Pattern 7A) |
| 2162-48-5 | Oxalic acid | 2:1 | 0.3 mL H₂O | Mixture of 1:1 salt and β-GPA |
| 2162-48-6 | Maleic acid | 2:1 | 0.3 mL H₂O | 2:1 salt was formed (Pattern 6B) |

Figure 14:
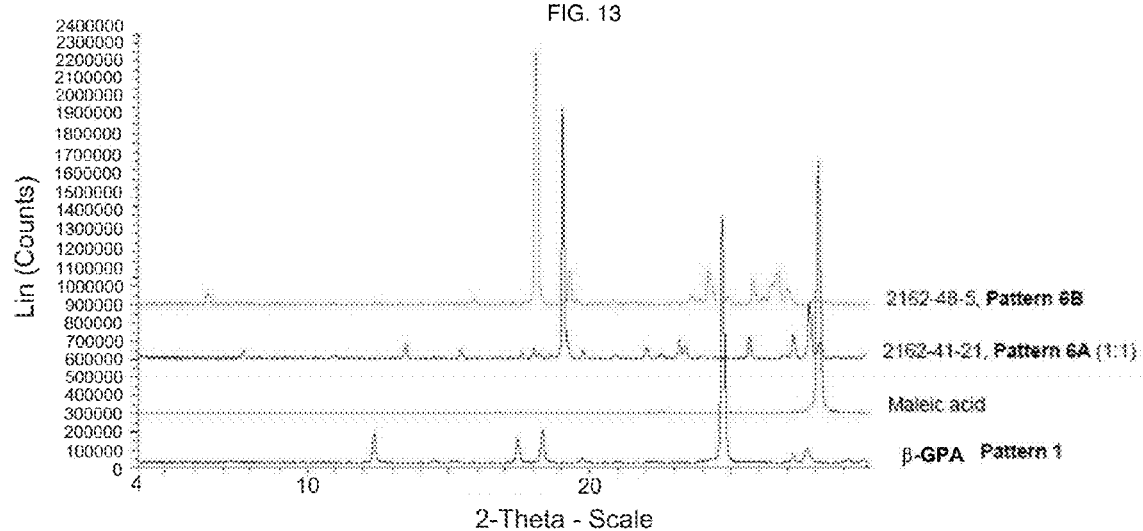
FIG. 14 is an image depicting X-ray powder diffraction (XRPD) pattern obtained for a crystalline form of the 2:1 maleate salt of β-GPA.
Figure 15:
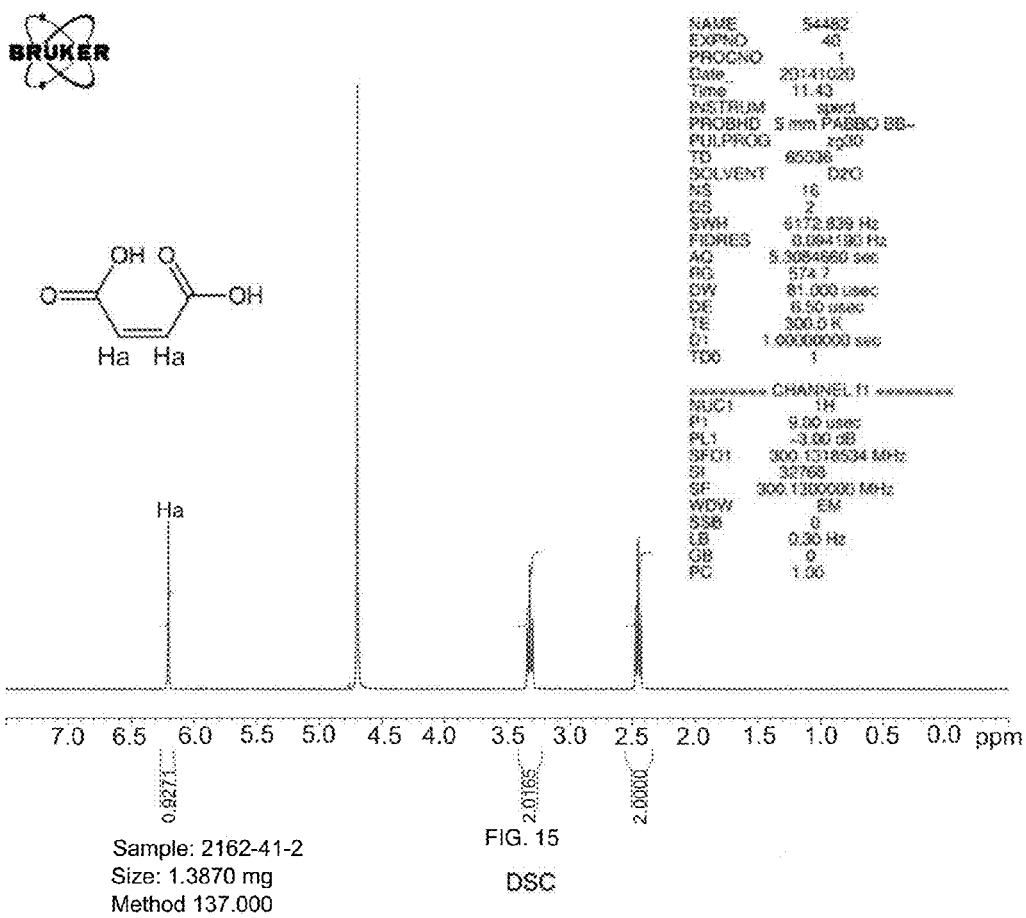
FIG. 15 is an image depicting a $^1$H NMR spectra of a crystalline form of the 2:1 maleate salt of β-GPA.

XRPD analysis revealed a new XRPD pattern for the maleic acid experiment (Pattern 6B, FIG. 14). The 1H-NMR revealed that a 2:1 salt was formed between β-GPA and maleic acid (FIG. 15).

Example 4. Physical and Thermal Characterization of β-GPA

Hydrochloric Acid Salt

Figure 16:
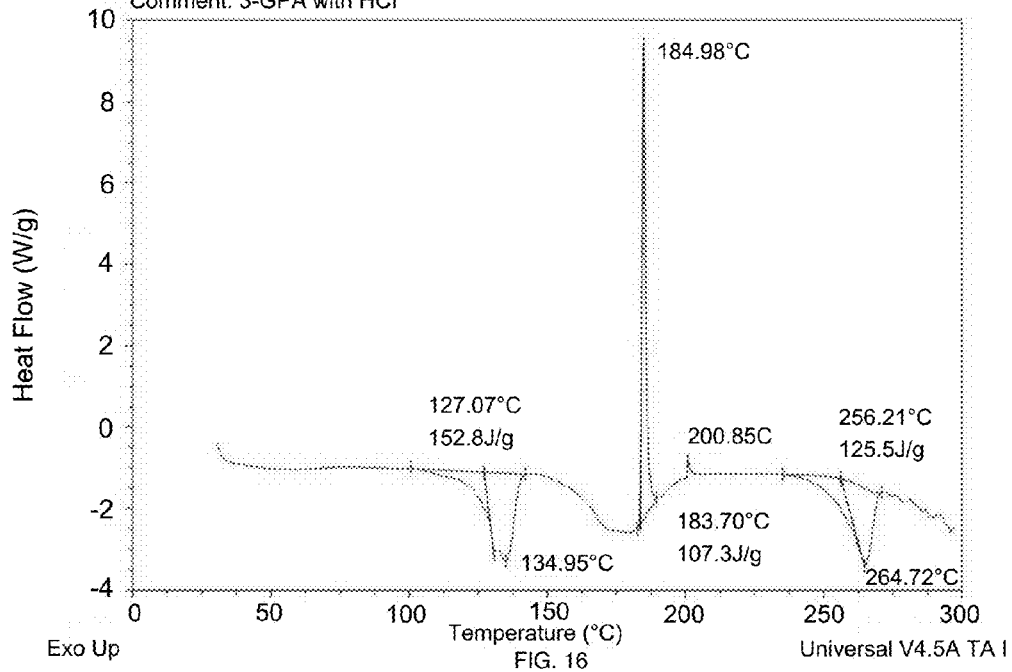
FIG. 16 is an image depicting a DSC thermogram obtained for a crystalline form of the 1:1 hydrochloride salt of β-GPA.
Figure 17:
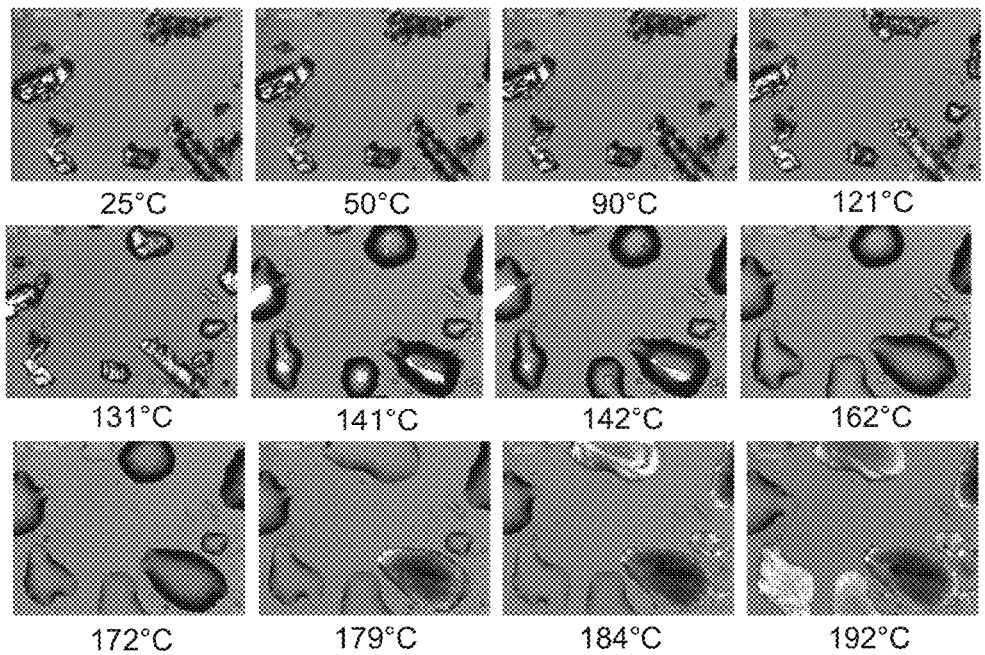
FIG. 17 is an image of a crystalline form of the 1:1 hydrochloride salt of β-GPA by hot stage microscopy.

The DSC of β-GPA-HCl salt (Sample ID: 2162-42-2) revealed the presence of an endothermic event at around 135° C. followed by an exothermic event at around 185° C. and an endotherm at 265° C. (FIG. 16). The exothermic event in the DSC arises from the recrystallization of the sample as confirmed by hot stage microscopy (FIG. 17). The TGA analysis revealed a weight loss of around 11% from 31° C. to 210° C.

Phosphoric Acid Salt

Even though there were some differences in the XRPD patterns of two samples that resulted in crystalline material of β-GPA with phosphoric acid, the DSC and TGA analysis were almost identical. Both samples exhibited a melting point at around 138° C. and a weight loss <1%. The phosphate analysis by Inductively Coupled Plasma/Optical Emission Spectrometry (ICP-OES) for the salt was found to be around 16% (Experimental value: 14%) and therefore it is likely a 1:1 salt.

Maleic Acid Salt (1:1 Salt)

Figure 18:
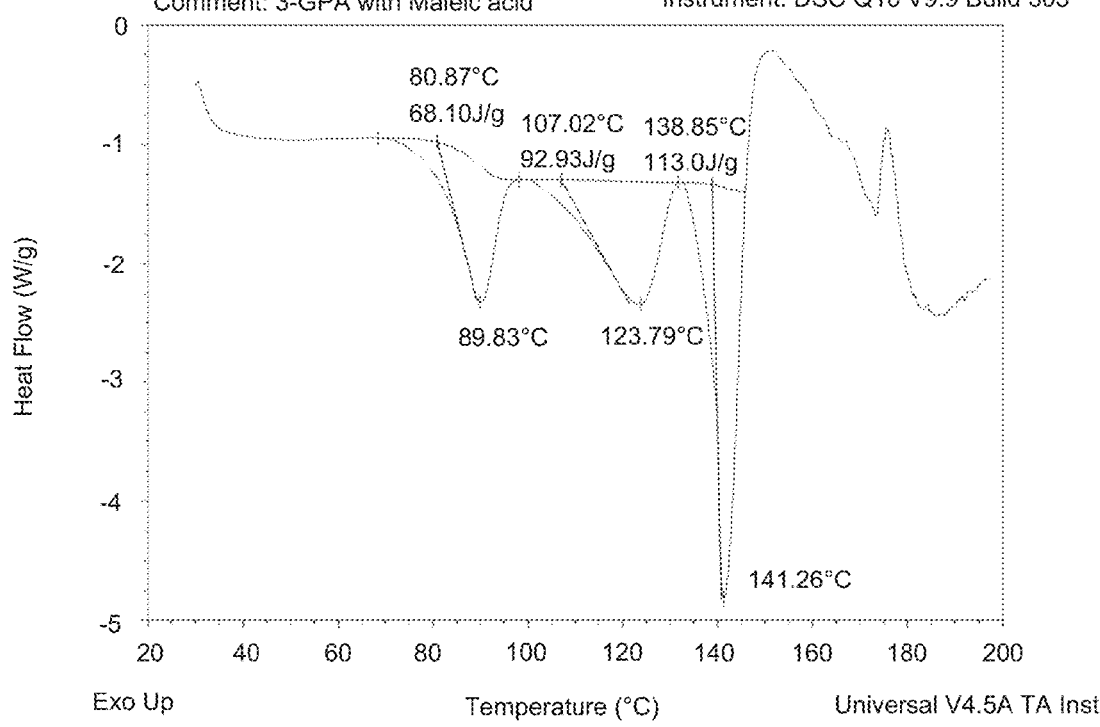
FIG. 18 is an image depicting a DSC thermogram obtained for a crystalline form of the 1:1 maleate salt of β-GPA.

The β-GPA-maleic acid salt (Sample ID: 2162-42-21) exhibited three endotherms at the following temperatures: 90, 124 and 141° C. (FIG. 18). TGA analysis revealed a weight loss of around 1.2% from 31 to 105° C. (1st endotherm) and a weight loss of around 5.4% from 105 to 138° C. (2nd endotherm).

Maleic Acid Salt (2:1 Salt)

The β-GPA-maleic acid salt (Sample ID: 2162-48-6) exhibited two endotherms at 85 and 155° C. respectively. However, the dried sample exhibited only one endotherm at 155° C. From the DSC analysis it is evident that a hydrate was formed in the prior case whereas an anhydrous form was yielded as a result of drying. TGA analysis revealed a weight loss of <0.1% from 31 to 145° C.

Figure 19:
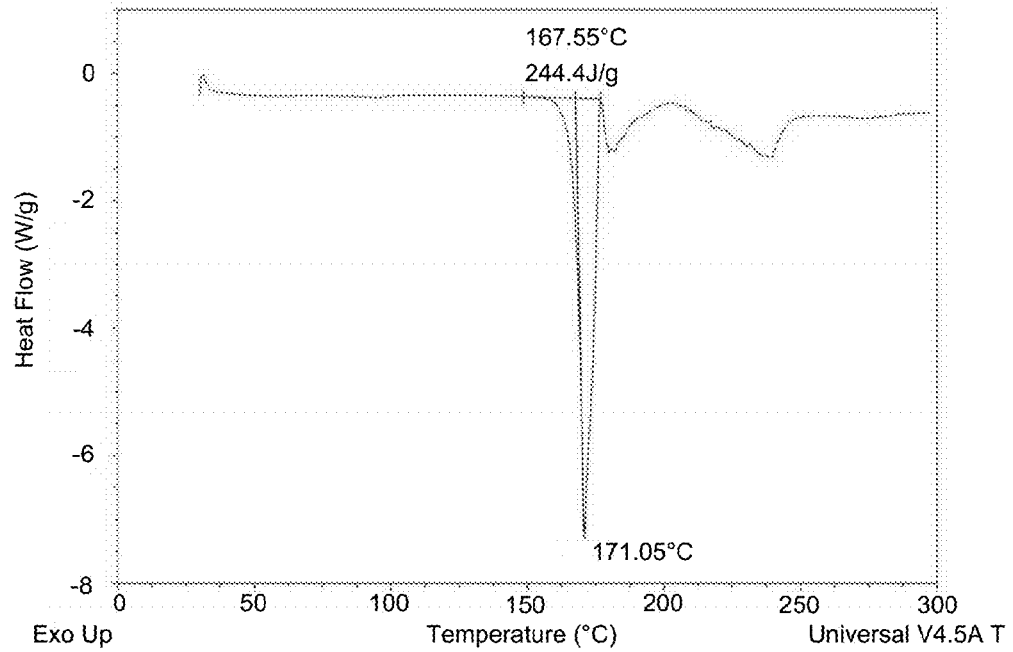
FIG. 19 is an image depicting a DSC thermogram obtained for a crystalline form of the 1:1 fumarate salt of β-GPA.
Figure 20:
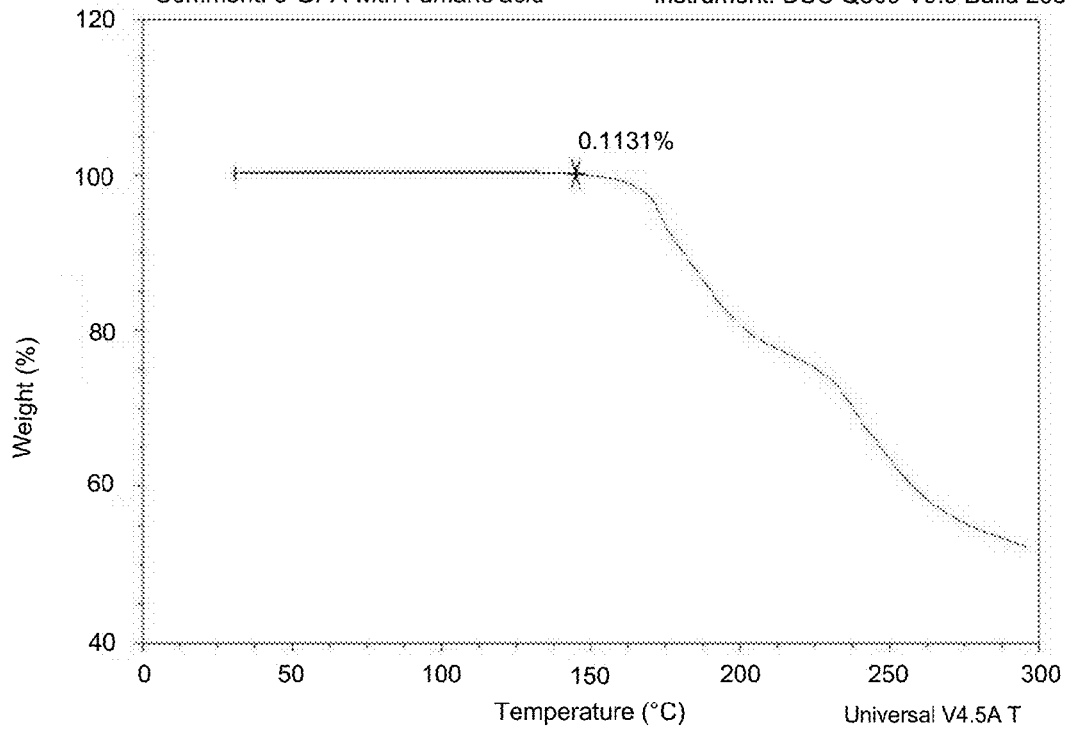
FIG. 20 is an image depicting TGA analysis obtained for a crystalline form of the 1:1 fumarate salt of β-GPA.
Figure 21:
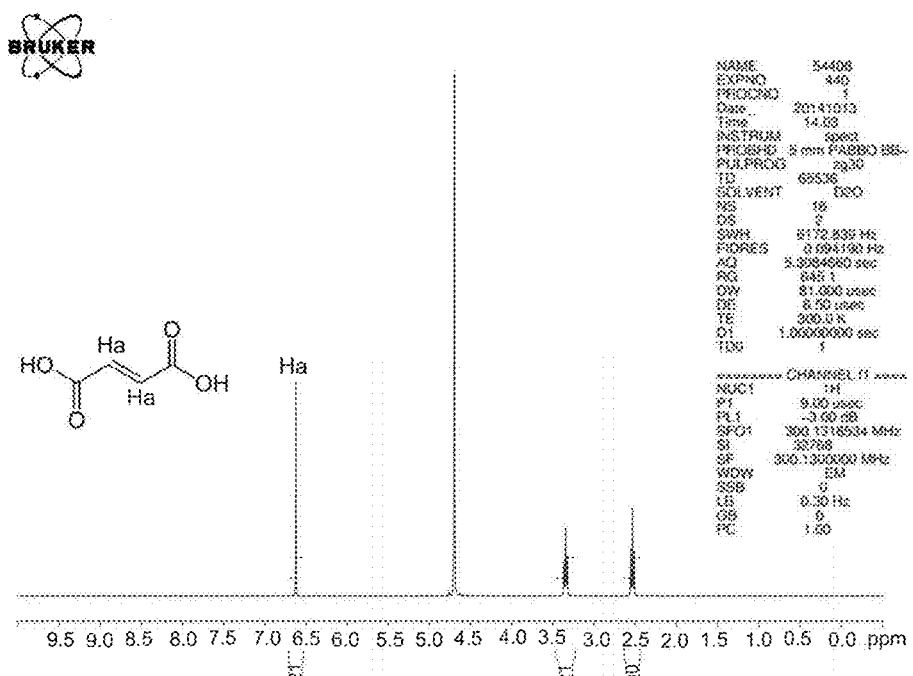
FIG. 21 is an image depicting a $^1$H NMR spectra of a crystalline form of the 1:1 fumarate salt of β-GPA.

Fumaric Acid Salt (1:1 Salt)

β-GPA—fumaric acid salt (Sample ID: 2162-42-25) exhibited an endotherm at 171° C. (FIG. 19) followed by possible decomposition of the salt. TGA analysis revealed a weight loss <1% from 31° C. to 145° C. (FIG. 20). The ¹H NMR of the 1:1 fumarate salt is shown in FIG. 21.

Figure 39:
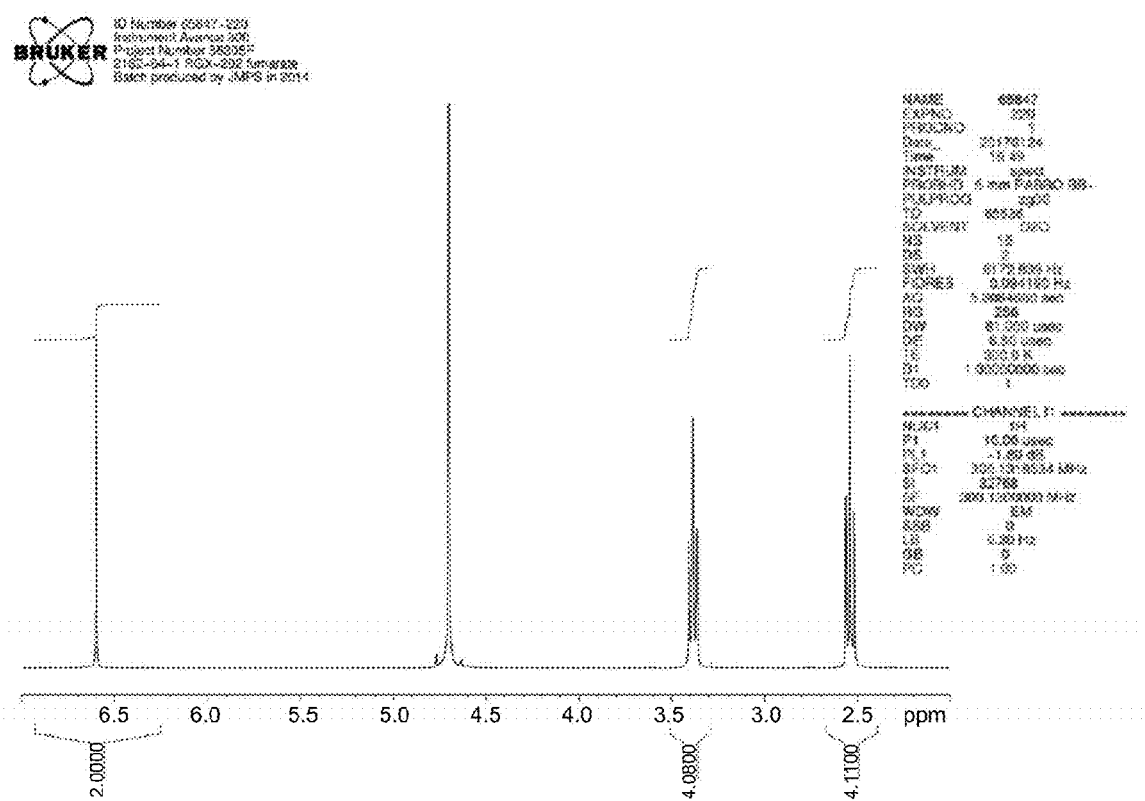
FIG. 39 is an image depicting a $^1$H NMR spectra of a crystalline form of the 2:1 fumarate salt of β-GPA (Pattern 7A).
Figure 40:
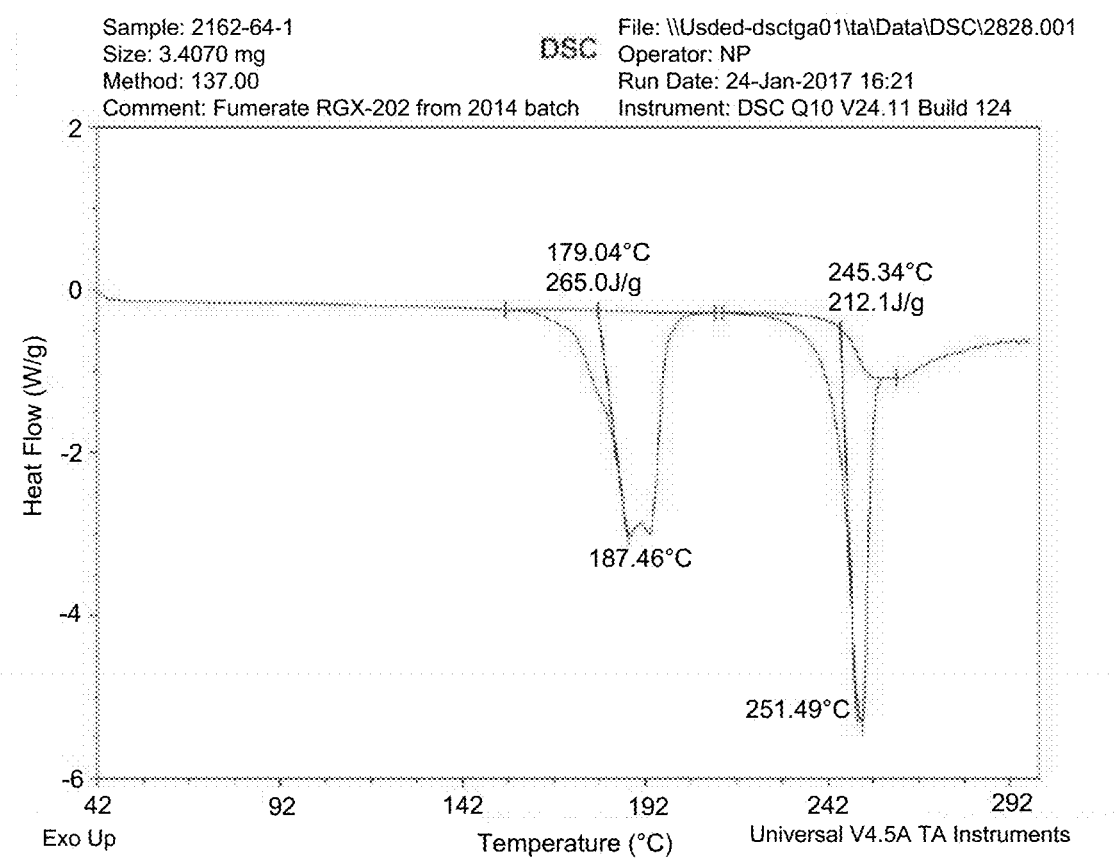
FIG. 40 is an image depicting a DSC thermogram obtained for a crystalline form of the 2:1 fumarate salt of β-GPA (Pattern 7A).
Figure 41:
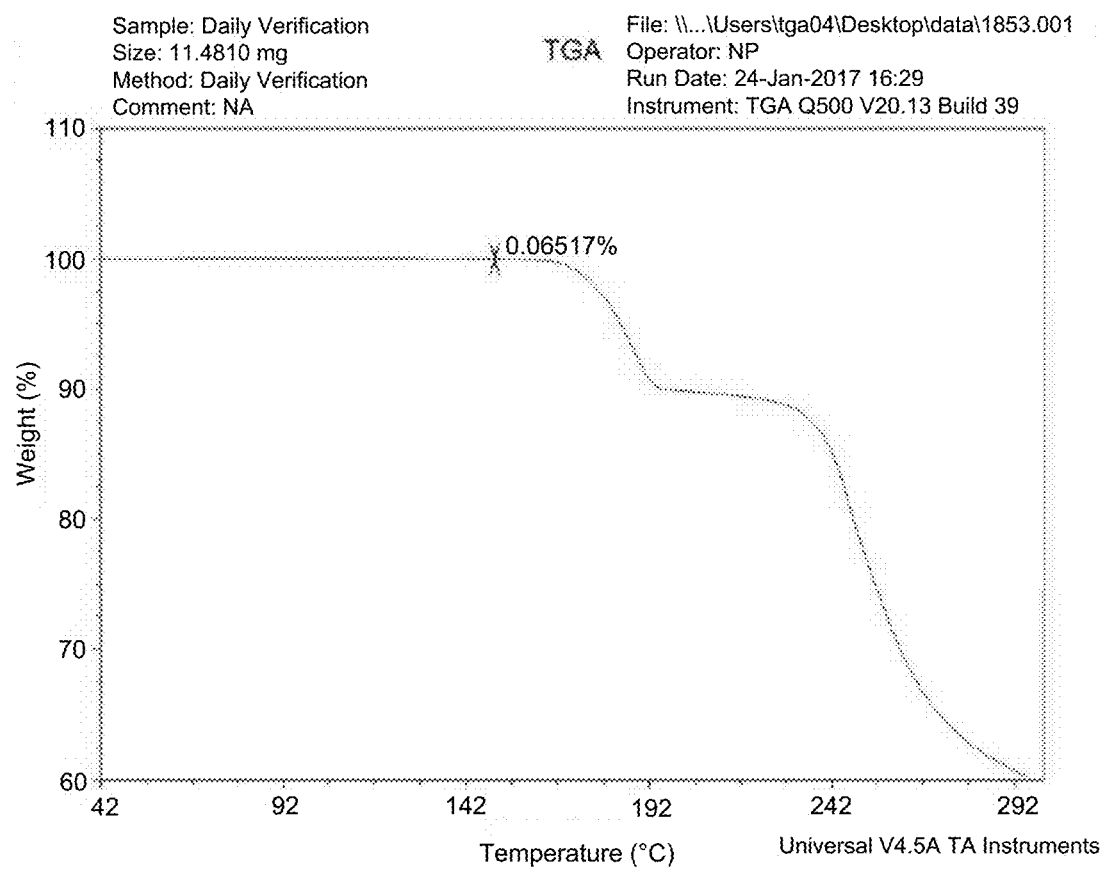
FIG. 41 is an image depicting TGA analysis obtained for a crystalline form of the 2:1 fumarate salt of β-GPA (Pattern 7A).

Fumaric Acid Salt (2:1 Salt)

β-GPA—fumaric acid salt (Sample ID: 2162-64-1) exhibited an endotherm at 187° C. and 251° C. (FIG. 40). TGA analysis revealed a weight loss <1% from 31° C. to 145° C. (FIG. 41). The ¹H NMR of the 2:1 fumarate salt is shown in FIG. 39.

Ethanesulfonic Acid Salt

The crystalline material that resulted from the experiment between β-GPA and ethanesulfonic acid did not dry out completely even after drying for more than two days in the oven at 50° C. (all the four vials).

When the sample was analyzed by DSC, a broad endothermic event was observed followed by decomposition and the TGA also revealed a weight loss from the starting point (31° C.). The ¹H-NMR of the sample revealed no traces of ethanesulfonic acid in the sample. Therefore, the crystalline material could have been a product of chemical reaction between β-GPA and ethanesulfonic acid.

L-Malic Acid Salt

β-GPA—L-malic acid salt (Sample ID: 2162-42-45) exhibited an endotherm at 110° C. followed by possible decomposition of the salt. TGA analysis revealed a weight loss <1% from 31° C. to 145° C. The ¹H-NMR of the salt confirmed it was a 1:1 salt.

Succinic Acid Salt (2:1 Salt)

Figure 22:
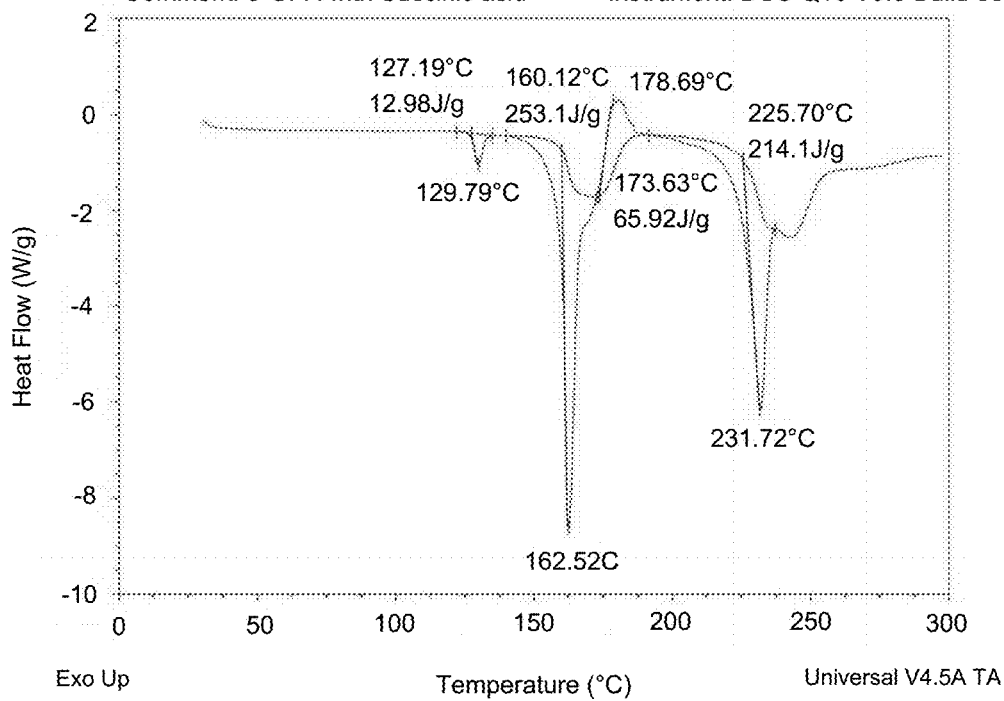
FIG. 22 is an image depicting a DSC thermogram obtained for a crystalline form of the 2:1 succinate salt of β-GPA.
Figure 23:
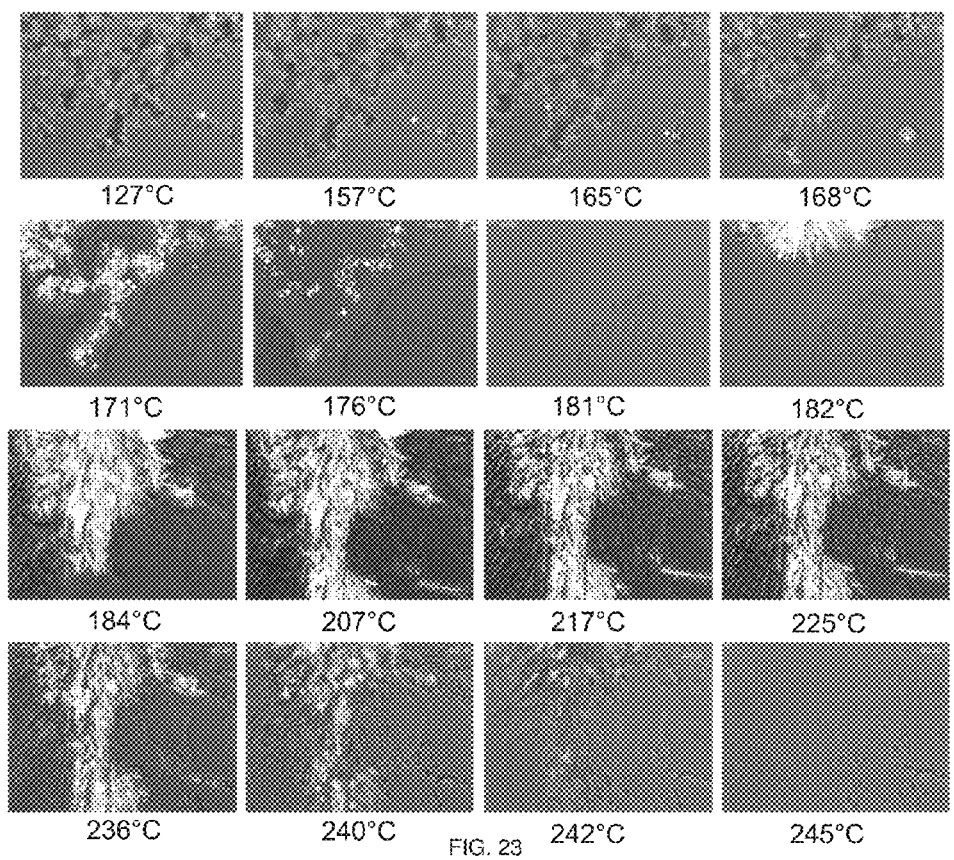
FIG. 23 is an image of a crystalline form of the 2:1 succinate salt of β-GPA by hot stage microscopy.
Figure 24:
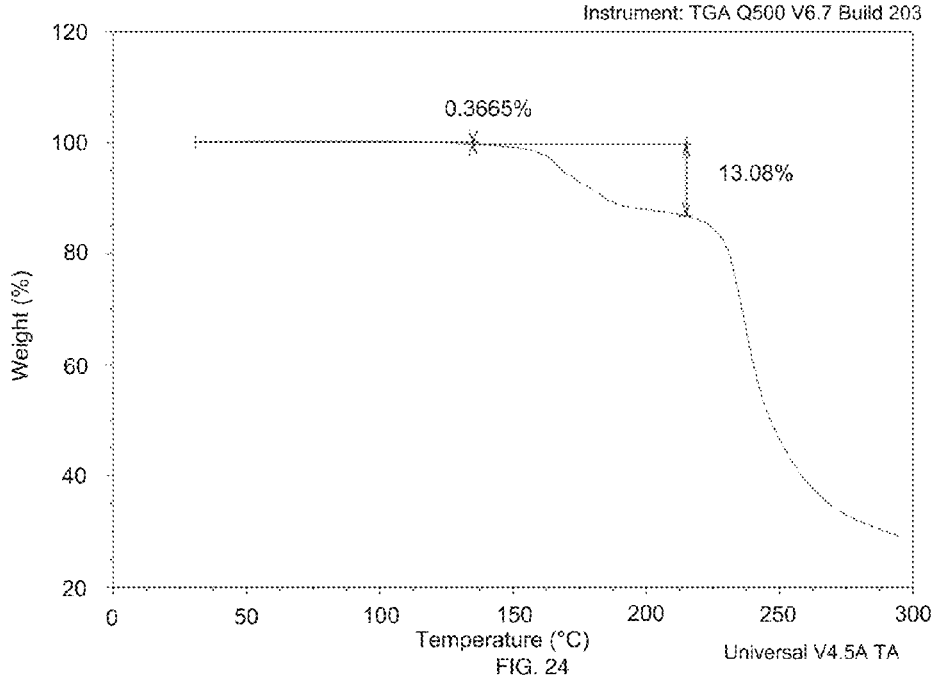
FIG. 24 is an image depicting TGA analysis obtained for a crystalline form of the 2:1 succinate salt of β-GPA.
Figure 25:
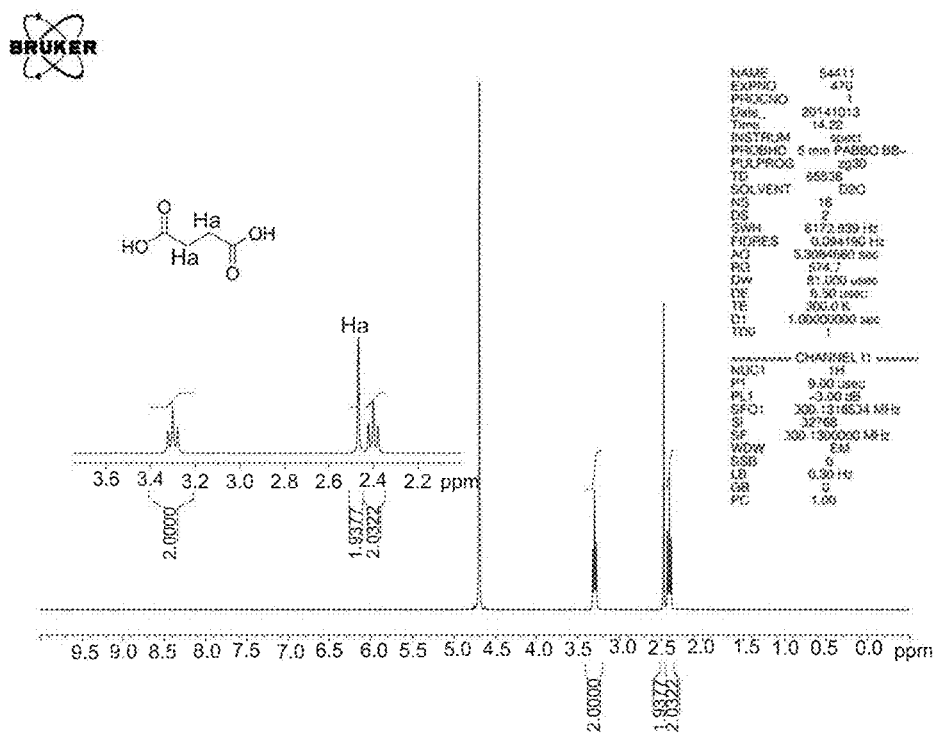
FIG. 25 is an image depicting a $^1$H NMR spectra of a crystalline form of the 2:1 succinate salt of β-GPA.

The DSC of β-GPA—succinic acid salt (sample ID: 2162-42-59) revealed the presence of an endothermic event at around 130° C. followed by another endothermic event at around 175° C. An exothermic event was observed at around 179° C. (FIG. 22) followed by an endothermic event at 232° C. To verify the endothermic and exothermic events in the DSC, hot stage microscopy was performed on the sample and illustrated in FIG. 23. The TGA analysis revealed a weight loss of around 0.4% from 31° C. to 135° C. and 13% from 135 to 215° C. (FIG. 24). The ¹H-NMR revealed that the salt formed between β-GPA and succinic acid was in 2:1 (β-GPA:acid) molar ratio (FIG. 25).

Oxalic Acid Salt (1:1 Salt)

Figure 26:
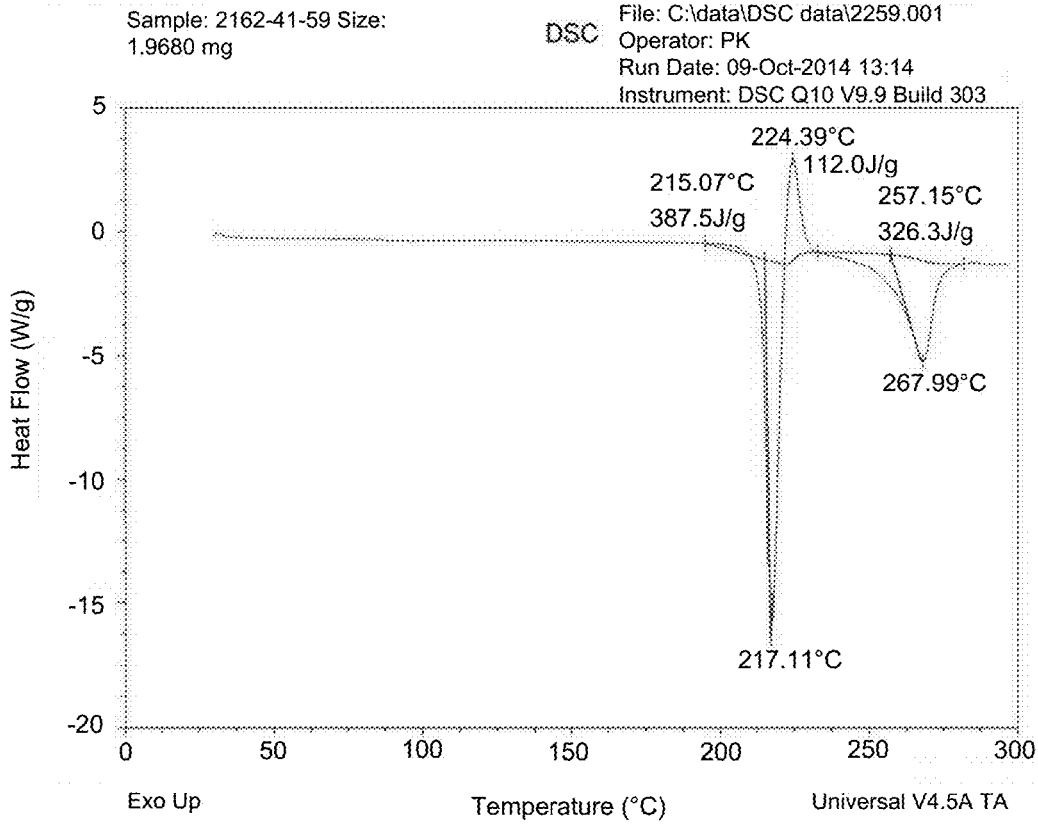
FIG. 26 is an image depicting a DSC thermogram obtained for a crystalline form of the 1:1 oxalate salt of β-GPA.
Figure 27:
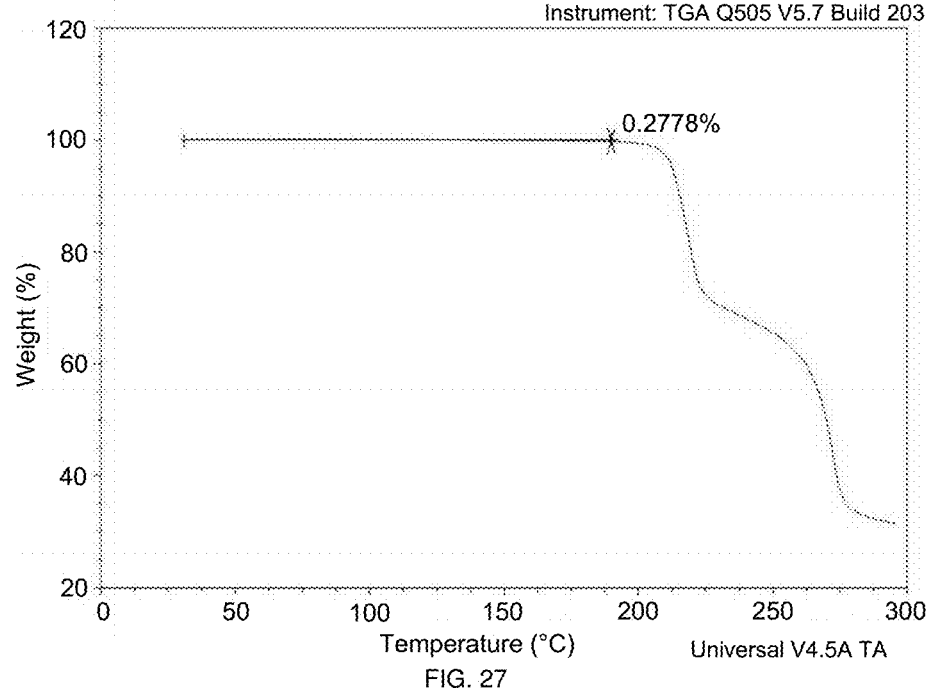
FIG. 27 is an image depicting TGA analysis obtained for a crystalline form of the 1:1 oxalate salt of β-GPA.
Figure 28:
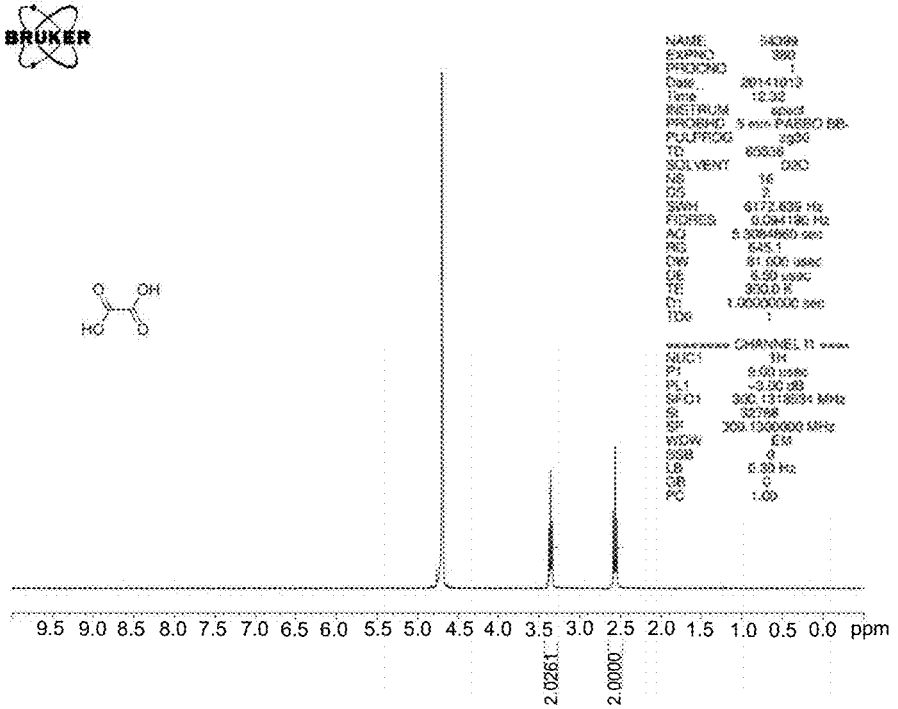
FIG. 28 is an image depicting a $^1$H NMR spectra of a crystalline form of the 1:1 oxalate salt of β-GPA.
Figure 29A:
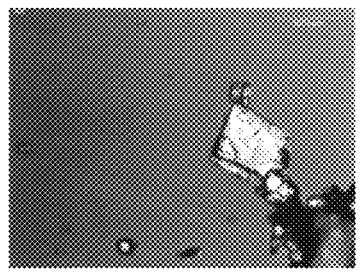
FIG. 29A-FIG. 29J are images of crystalline forms of β-GPA salts.
Figure 29B:
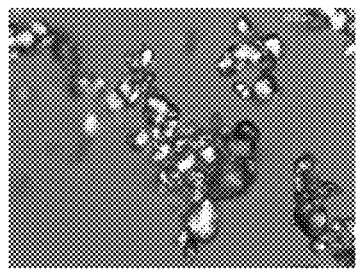
Figure 29C:
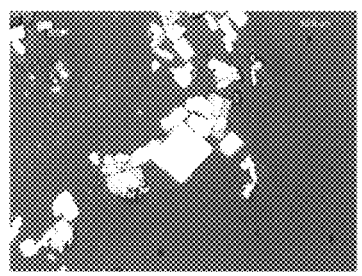
Figure 29D:
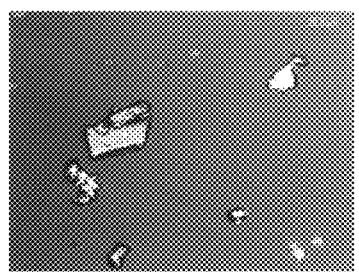
Figure 29E:
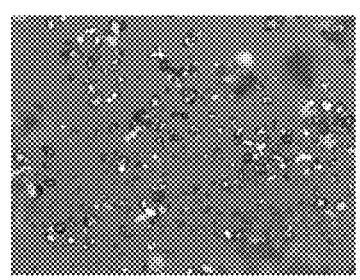
Figure 29F:
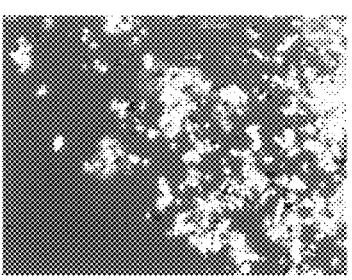
Figure 29G:
Figure 29H:
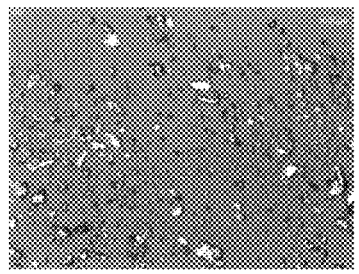
Figure 29I:
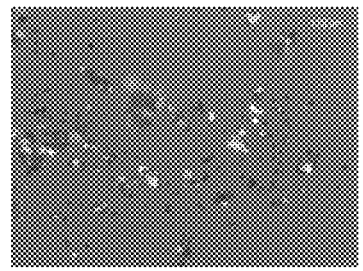
Figure 29J:
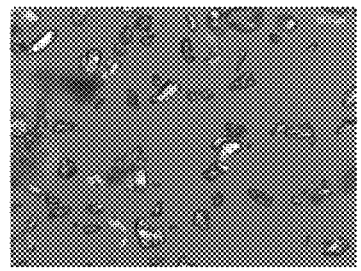

The β-GPA—oxalic acid (Sample ID: 2162-42-69) when analyzed by DSC revealed a presence of an endothermic event at around 217° C. followed by an exothermic peak at around 224° C. and an endotherm at 268° C. as represented in FIG. 26. The TGA analysis revealed a weight loss of <0.3% from 31 to 195° C. (FIG. 27). When the material was observed under hot-stage microscope, at 216 to 226° C. there were very few crystals that appeared to melt however, there was no visible recrystallization event which was observed. From 268° C. melting of the crystals started to occur until 291° C. The ¹H-NMR of β-GPA oxalate is presented in FIG. 28. From the elemental analysis the stoichiometric ratio of β-GPA to oxalic acid was found to be 1:1 (Intertek).

Example 5. Optical Microscopic Imagery

Figure 30:
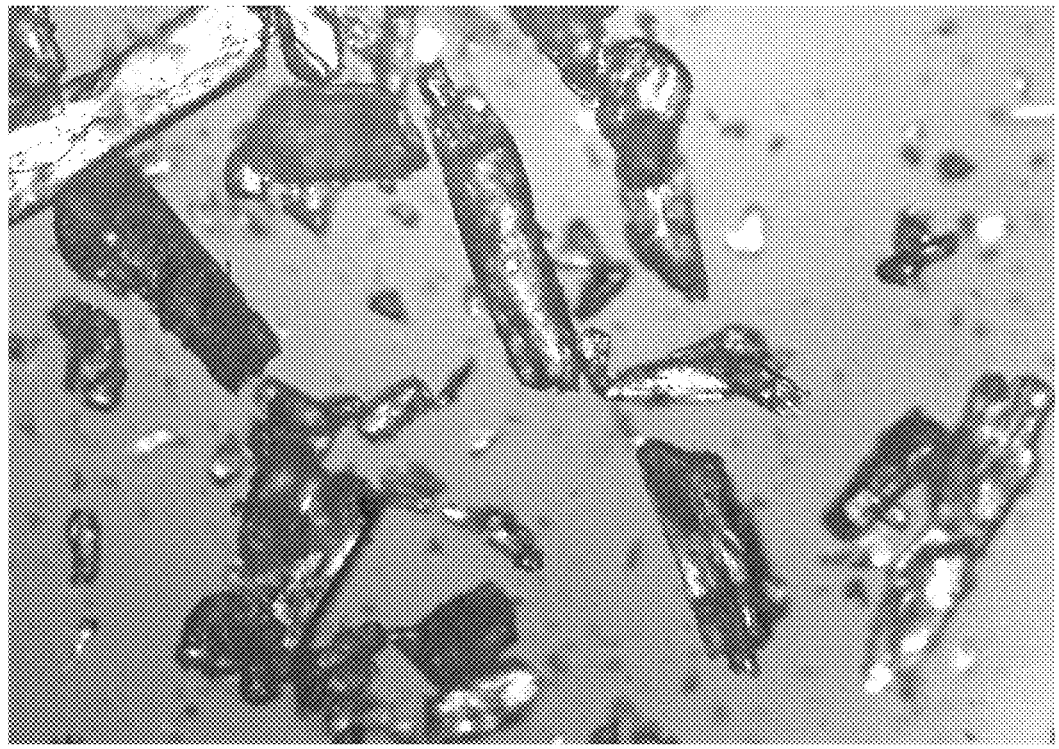
FIG. 30 is an image depicting the rod-like crystal morphology of 1:1 fumarate salt of β-GPA (Pattern 7A).

Salts of β-GPA were also analyzed by optical microscopy. Optical microscopic images of β-GPA salts are presented from FIG. 29A to 29J. As shown in FIG. 30, β-GPA fumarate (1:1) has a rod-like crystal morphology.

Example 6. Stability Testing of β-GPA Salts Under Stressed Conditions

The solid form stability of each salt was studied by XRPD under stressed conditions: wet, dry (45° C. under vacuum) and high humidity (RH >95%). The results are tabulated in Table 14.

TABLE 14

Results of Stability Studies

| Salt | Wet_XRPD pattern | Dry_XRPD pattern | Humid_XRPD pattern |
|---|---|---|---|
| β-GPA hydrochloride | Pattern 1A | Pattern 1A | Deliquesce |
| β-GPA phosphate | Pattern 4A | Pattern 4A | Deliquesce |
| β-GPA methanesulfonate | Pattern 19A | Pattern 19A | Deliquesce |
| β-GPA maleate (1:1) Form I | Pattern 6A | Pattern 6A | Pattern 6A |
| β-GPA maleate (1:1) Form II | Pattern 6D | Pattern 6D | Pattern 6D |
| β-GPA maleate (2:1) | Pattern 6B | Pattern 6C | Pattern 6B |
| β-GPA fumarate (1:1) | Pattern 7A | Pattern 7A | Pattern 7A |
| β-GPA malate (1:1) | Pattern 12A | Pattern 12A | Deliquesce |
| β-GPA succinate (2:1) | Pattern 15A | Pattern 15A | Pattern 15A |
| β-GPA oxalate (1:1) | Pattern 18A | Pattern 18A | Pattern 18A |

Example 7. DVS Experiments

Four salts: β-GPA maleate (1:1) Form II, β-GPA fumarate (1:1), β-GPA maleate (2:1), β-GPA succinate (2:1) and β-GPA oxalate (1:1) were analyzed by DVS experiment followed by XRPD analysis of the sample at the end of the experiment.

1:1 β-GPA maleate (Pattern 6D) exhibited an increase in the moisture uptake from 60% RH and at around 95% RH there was around 25% moisture uptake, however, there was no form change after the end of the experiment as confirmed by XRPD.

Figure 31:
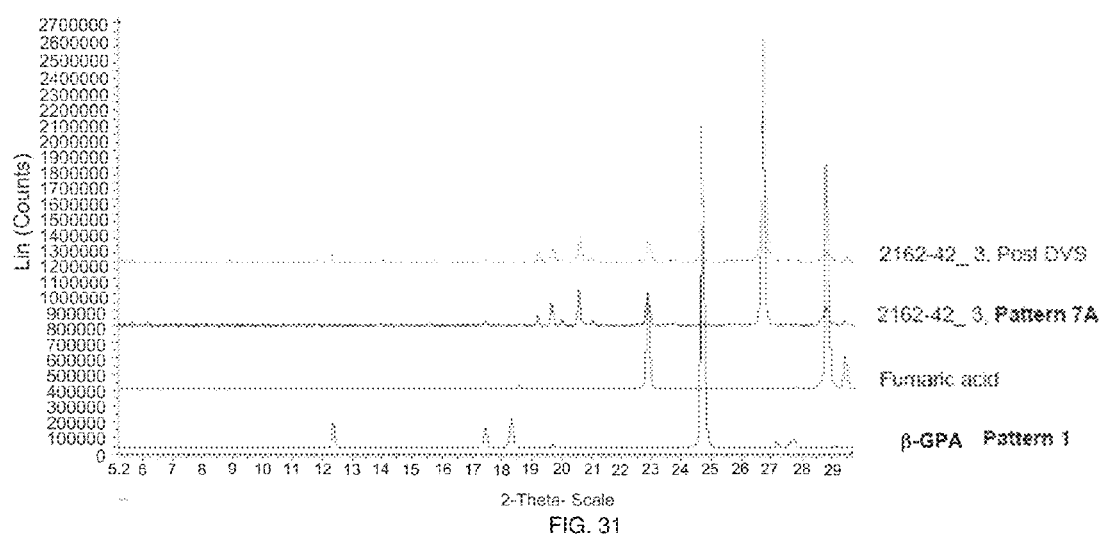
FIG. 31 is an image depicting a comparison of XRPD analysis before and after DVS of 1:1 fumarate salt of β-GPA (Pattern 7A).

1:1 β-GPA fumarate exhibited <1% moisture uptake during the DVS experiment. XRPD analysis on the Post DVS sample revealed the presence of β-GPA peaks along with Pattern 7A (FIG. 31).

Both the 2:1 β-GPA succinate and 1:1 β-GPA oxalate salts revealed <0.5% moisture uptake during the DVS experiment and no form change was observed after the end of the experiment.

Example 8. Solid Form Stability of Salts in Different Solvents

Three salts were studied for solid form stability in water (disproportionation test), methanol, acetonitrile, and acetone:water (9:1) for 48 hours at room temperature.

1:1 β-GPA oxalate and 1:1 β-GPA fumarate salts retained their XRPD pattern after 48 hours slurry in water. 2:1 β-GPA succinate started showing up peaks from β-GPA after 6 hours slurry in water and thus the experiment was stopped after 6 hours.

After slurrying the 1:1 β-GPA fumarate and 1:1 β-GPA oxalate salts in methanol, acetonitrile, and acetone:water (9:1), the salts were found to retain their XRPD pattern.

After slurrying the 2:1 β-GPA succinate in methanol and acetonitrile, the salt was found to retain its XRPD pattern. However, the slurry in acetone:water (9:1) revealed the presence of β-GPA after 48 hours.

Example 9. Solid Form Stability of Salts at 40° C. and 75% Humidity

Solid form stability studies of β-GPA fumarate, succinate, and oxalate were carried out at 40° C. and 75% RH for seven days. Around 30 mg of the salts were placed in 4 mL vials which were placed in a saturated solution of sodium chloride (2 mL) with lids closed at 40° C. The samples were left for a week followed by XRPD analysis of the salts. All three salts retained their original XRPD pattern.

Example 10. Purity of Salts

The purity of β-GPA salts was determined by HPLC using the method below.

The HPLC method is described below:

Column: SeQuant ZIC Hilic PEEK column (250×4.6 mm, 5 μm)

Mobile Phase A: 0.02M Phosphate buffer, pH 3.0

The mobile phase was prepared by dissolving 2.72 g of monobasic potassium phosphate in 1L of deionized water and the adjusting the desired pH by 85% (w/w) phosphoric acid.

Mobile Phase B: 100% Acetonitrile

Gradient used:

Time (minutes) A % B %
0 25 75
15.0 25 75
23.0 80 20
25.0 80 20
25.1 25 75
30.0 25 75

Flow rate: 1 mL/min
Injection volume: 10 μL
Detector wavelength: 210 nm
Run time: 30 minutes
Column temperature: 40° C.
Diluent: Acetonitrile:water (1:1)

The counterions were also analyzed by HPLC under the same concentrations as they were present in the respective salts.

The purity of β-GPA salts is listed in Table 15.

TABLE 15

Purity of Salts

| β-GPA salt | Purity by HPLC |
|---|---|
| β-GPA fumarate (1:1) | 97.7% |
| β-GPA succinate (2:1) | 98.1% |
| β-GPA oxalate (1:1) | 98.4% |

Example 11. Scale-Up of Salts

Oxalate Salt

Around 7.2 g (0.055 moles) of β-GPA was added to an EasyMax reaction vessel containing 30 mL water. The reaction mixture was stirred at 90° C. until a clear solution was obtained. To this solution, around 5.4 g (0.06 moles) of oxalic acid was added slowly and the temperature of the reactor was brought down to 20° C. Around 20 mL of isopropanol was added to the reaction mixture was left for overnight stirring. Sample ID: 2162-64-2.

The following day, the slurry was filtered and the solid was washed twice with 10 mL of isopropanol. The cake was placed in a vacuum oven at 45° C. for drying. Yield=11.4 g (94%). The solid was analyzed by XRPD and β-GPA oxalate salt, Pattern 18A, formation was confirmed.

Succinate Salt

Around 72 g (0.55 moles) of β-GPA was added to 400 mL of ethanol:water (9:1) in 500 mL jacketed vessel at 75° C. and a slurry was made. To this, a slurry of succinic acid, prepared by adding 71.2 g (0.6 moles) in 200 mL ethanol:water (9:1) at 65° C., was added. The temperature of the reactor was brought down to 18° C. and the reaction mixture was left for overnight stirring. Sample ID: 2162-62-1.

The following day, the slurry was filtered and the solid was washed twice with 20 mL of isopropanol. The cake was placed in a vacuum oven at 45° C. for drying. Yield=101.3 g (97%). The solid was analyzed by XRPD and the formation of β-GPA succinate (Pattern 15 A) was confirmed.

Fumarate Salt

Around 48 g (0.37 moles) of β-GPA was added to 120 mL of water in 500 mL jacketed vessel at 90° C. and a clear solution was obtained. To this solution, a solution of fumaric acid, prepared by dissolving 46.8 g (0.40 moles) in 220 mL methanol at 65° C., was added. The temperature of the reactor was brought down to 18° C. and the reaction mixture was left for overnight stirring. Sample ID: 2162-64-1.

The following day, the slurry was filtered and the solid was washed twice with 20 mL of isopropanol. The cake was placed in a vacuum oven at 45° C. for drying. Yield=61.5 g (90%). The solid was analyzed by XRPD and the formation of β-GPA fumarate (Pattern 7A) was confirmed. After NMR analysis this salt was determined to be the 2:1 fumarate salt. After further analysis, it was determined that the 2:1 and 1:1 fumarate salts have similar XRPD patterns.

Example 12. Determination of Bulk and Tapped Density

The bulk density of β-GPA oxalate (Pattern 18 B), succinate (Pattern 15A), and fumarate (Pattern 7A) were determined by pouring in a known amount of salt (g) into a measuring cylinder. The volume ($V_i$) occupied by the salt was recorded and the bulk density ($\rho_B$) was determined using equation 1.

$$\rho_B = g/V_i \quad (1)$$

The tapped densities of the salts were determined using a Tap density analyzer. A known amount of salt was poured (g) into a measuring cylinder and the initial volume was recorded and tapped using a Tap density analyzer. The final volume ($V_f$) after tapping was recorded and the tapped density ($\rho_T$) was calculated by using equation 2.

$$\rho_T = g/V_f \quad (2)$$

Table 16 lists the bulk and tapped density of β-GPA and salts thereof.

TABLE 16

Bulk and Tapped Densities

| Sample | Bulk density (ρB) | Tapped density (ρT) |
|---|---|---|
| β-GPA | 0.389 g/cc | 0.627 g/cc |
| β-GPA oxalate (1:1) | 0.505 g/cc | 0.623 g/cc |
| β-GPA succinate (2:1) | 0.405 g/cc | 0.472 g/cc |
| β-GPA fumarate (2:1) | 0.576 g/cc | 0.613 g/cc |

Example 13. Determination of Carr's Index and Hausner Ratio

Carr's index or Carr's compressibility index (C) is an indication of the compressibility of a powder. It can be calculated using the equation below:

$$\text{Carr's index } (C) = 100(V_i - V_f)/V_i \quad (3)$$

A Carr's index greater than 25 is considered to be an indication of poor flowability while a value below 15 is an indication of good flowability.

The Hausner ratio is a number that is correlated to the flowability of a powder or granular material. It is calculated by using the equation below:

$$\text{Hausner ratio} = V_i/V_f \quad (4)$$

Table 17 lists the Carr's index and Hausner ratio corresponding to the flow character of a powder proposed by R. L. Carl.

TABLE 17

Flow Characteristics Based on Carr's Index and Hausner Ration

| Carr index | Flow character | Hausner ratio |
|---|---|---|
| 1-10 | Excellent | 1.00-1.11 |
| 11-15 | Good | 1.12-1.18 |
| 16-20 | Fair | 1.19-1.25 |
| 21-25 | Passable | 1.26-1.34 |
| 26-31 | Poor | 1.35-1.45 |
| 32-37 | Very poor | 1.46-1.59 |
| >38 | Very very poor | >1.60 |

Table 18 lists the Carr's index and Hausner ratio for β-GPA and salts thereof.

TABLE 18

Carr's Index and Hausner Ratio for β-GPA and Salts Thereof

| Sample | Carr index | Flow character | Hausner ratio |
|---|---|---|---|
| β-GPA | 37.9 | Very very poor | 1.610 |
| β-GPA oxalate (1:1) (Pattern 18A, original salt) | 18.7 | Fair | 1.23 |
| β-GPA succinate (2:1) (Pattern 15A) | 14.3 | Good | 1.167 |
| β-GPA fumarate (2:1) (Pattern 7A) | 5.9 | Excellent | 1.063 |

Example 14. Flowability Measurement Using Hanson Flodex Unit

Method: A cylindrical vessel is secured to the stand and above that a funnel is also secured such that the bottom of the funnel is close to the vessel. A powder load of ≈50-60 g is then poured through the funnel into the middle of the cylinder. The lever device is pulled to open the hole in the disk quickly and without vibration. If a powder slowly flows through the small-diameter holes, leaving a cavity shaped like an upside-down, truncated cone, the test is considered positive. If a powder flocculates in bulk and falls abruptly, forming a cylindrical cavity, the test is considered negative. If a powder does not fall through the small-diameter holes, the test is considered negative. If the experiment is negative, the powder is tested again with a disk having a larger hole. Tables 19-22 list the flowability test results for β-GPA and salts thereof.

TABLE 19

Flowability Test Results for β-GPA

| Run # | Disc pore Size mm | Did solid pass? |
|---|---|---|
| 1 | 18 | No |
| 2 | 20 | No |
| 3 | 28 | No |
| 4 | 32 | Yes, but the powder fell abruptly forming a cylindrical cavity (flocculation). Thus, the test was considered negative. |
| 5 | 30 | No |
| 6 | 34 | Yes |

TABLE 20

Flowability Test Results for the Oxalate Salt

| Run # | Disc pore Size mm | Did solid pass? |
|---|---|---|
| 1 | 12 | No |
| 2 | 18 | No |
| 3 | 24 | No |
| 4 | 30 | Yes |
| 5 | 28 | Yes |
| 6 | 26 | Yes |

TABLE 21

Flowability Test Results for the Succinate Salt

| Run # | Disc pore Size mm | Did solid pass? |
|---|---|---|
| 1 | 24 | Yes |
| 2 | 22 | Yes |
| 3 | 20 | Yes |
| 4 | 18 | Yes |
| 5 | 10 | Yes |
| 6 | 8 | Yes |
| 7 | 7 | Yes |
| 8 | 5 | No |
| 9 | 6 | No |

TABLE 22

Flowability Test Results for the Fumarate Salt

| Run # | Disc pore Size mm | Did solid pass? |
|---|---|---|
| 1 | 12 | Yes |
| 2 | 6 | Yes |
| 3 | 4 | No |
| 4 | 5 | Yes |

Example 15. DVS and Stability at High Humidity of the 2:1 Fumarate Salt

Sample 2162-64-1 was analyzed by DVS in triplicate and the post DVS samples were characterized by XRPD to identify the form at the end of the experiment. In all the three experiments, the moisture uptake by β-GPA fumarate was found to be less than 0.1%. In all the three experiments, the XRPDs were found to be identical to β-GPA fumarate (Pattern 7A) and no appearance of β-GPA peaks were observed, unlike sample 2162-42-3 post DVS (FIG. 30).

The solid form stability of 2162-64-1 was also studied at RH >95% at room temperature. β-GPA fumarate was found to retain its original XRPD pattern (Pattern 7A) after 48 hours.

Summary of Salt Screening Experiments

Ten salts of β-GPA namely, β-GPA HCl. β-GPA phosphate, β-GPA mesylate, β-GPA maleate (1:1, Pattern 6A), β-GPA maleate (1:1, Pattern 6D), β-GPA maleate (2:1, Pattern 6B), β-GPA fumarate, β-GPA malate, β-GPA succinate and β-GPA oxalate, were isolated from salt screening experiments (Stages I and II).

Of the ten salts, six of the salts, β-GPA HCl, β-GPA phosphate, β-GPA mesylate, β-GPA maleate (1:1, Pattern 6A), β-GPA malate, and β-GPA maleate (2:1, Pattern 6B), were excluded from further studies owing to their deliquescent nature, non-reproducibility, or purity issues.

Foursalts of β-GPA were selected after performing the DVS experiments: β-GPA maleate (1:1), fumarate (1:1), succinate (2:1) and oxalate (1:1) and the form stability was determined by XRPD.

β-GPA fumarate, succinate and oxalate retained their XRPD after the DVS experiment. However, β-GPA fumarate revealed the presence of two peaks from the β-GPA indicating dissociation of the salt.

The scaled-up sample of β-GPA fumarate, which was determined to be the 2:1 salt, was again analyzed by DVS three times and in these experiments the sample did not exhibit any dissociation of the salt. Indicating that the 2:1 fumarate salt is more stable than the 1:1 salt. Additional solid form stability testing of β-GPA fumarate at RH >95% at 20° C. also revealed that the salt was stable.

The purity assessment for the salts was carried out by HPLC and the purity of the salts was as follows: β-GPA fumarate—97.7%, β-GPA succinate—98.1% and β-GPA oxalate—98.4%.

Stability studies of salts were also carried out by slurrying them in water (test for disproportionation), methanol, acetonitrile, and acetone:water (9:1) for 48 hours at room temperature. The following results were obtained:

β-GPA maleate, fumarate and oxalate retained their XRPD patterns after 48 hours slurry in water while, β-GPA succinate showed two peaks from β-GPA after 6 hours slurry in water.

After 48 hours slurry, β-GPA maleate in methanol and acetonitrile was found to retain its XRPD pattern. However, the slurry in acetone:water (9:1) matched with the original pattern of the salt (Pattern 6D) along with some additional peaks in the XRPD analysis.

After 48 hours slurry, β-GPA succinate in methanol and acetonitrile salt was found to retain its original form. However, the slurry in acetone:water (9:1) revealed the presence of β-GPA after 48 hours along with the salt by XRPD analysis.

Solid form stability studies of β-GPA fumarate, succinate, and oxalate were carried out at 40° C. and 75% RH for seven days. All the three salts were found to be stable and retained their original XRPD patterns.

Three salts of β-GPA were scaled up to 60-100 g scale. β-GPA fumarate and succinate were scaled-up successfully; however β-GPA oxalate resulted in an ethanol solvate of the salt (confirmed by $^1$H-NMR). The mole percent of ethanol to β-GPA was found to be 0.22 to 1 (Pattern 18 B).

Nevertheless, by changing the solvent system from ethanol:water (9:1) to water and isopropanol the original β-GPA oxalate salt was produced, but the XPRD pattern confirmed the presence of new additional peaks in minor quantities.

The bulk and tapped densities of β-GPA and its salts: β-GPA oxalate (Patterns 18A and B), fumarate, and succinate were determined using density analyzer unit. Likewise, flowability measurements for the salts were measured using Hanson Flodex unit.

From the experimental data β-GPA and β-GPA oxalate (Pattern 18B) were found to exhibit poor flow character whereas, β-GPA oxalate (Pattern 18A) was fair whilst, β-GPA succinate was good, and β-GPA fumarate exhibited excellent flow characteristics.

Based on the solid form stability, reproducibility, density and flowability properties the 2:1 β-GPA fumarate salt appears to have the best properties of the salts screened.

Example 16. Polymorph Screening of the 2:1 β-GPA Fumarate Salt

Solid Form Stability of the 2:1β-GPA Fumarate Salt

The solid form stability of β-GPA fumarate was studied at various temperature/humidity conditions as listed in Table 23 for a week using saturated salt solution chambers. The samples were analyzed by XRPD after a week. The XRPD analysis of the stability samples for β-GPA fumarate under various temperature/RH conditions indicated that β-GPA fumarate retained the original XRPD pattern (Pattern 7A)

TABLE 23

Stability Study Results

| Sample ID | Temperature (° C.) | Relative humidity | Saturated salt solution* | XRPD |
|---|---|---|---|---|
| 2162-75-1 | 20 | 43% | Potassium carbonate | Pattern 7A |
| 2162-75-2 | 20 | 59% | Sodium bromide | Pattern 7A |
| 2162-75-3 | 20 | 73% | Sodium chloride | Pattern 7A |
| 2162-75-4 | 40 | 82% | Potassium chloride | Pattern 7A |
| 2162-75-5 | 60 | 50% | Sodium bromide | Pattern 7A |
| 2162-75-6 | 60 | 80% | Potassium chloride | Pattern 7A |
| 2162-75-7 | 20 | >95% | Water | Pattern 7A |

Solubility of the 2:1 β-GPA Fumarate Salt

Solubility of β-GPA fumarate was measured gravimetrically in fifteen different solvents and solvent mixtures at 15 and 45° C. About 100 mg of the compound was dispensed in ten volumes (1 mL) of the solvent/solvent mixture and slurried for 48 hours. Table 24 represents the solubility of β-GPA fumarate in different solvents. After 48 hours the vials were centrifuged. The supernatant was collected and left for slow evaporation under vacuum at 45° C. and solubility was determined. The solids obtained after centrifugation and evaporation were analyzed by XRPD. The XRPD analysis of the precipitates after 48 hours slurries revealed no form transformations for 2:1 β-GPA fumarate.

TABLE 24

Results of Solubility Study

| Solvent | Temp (° C.) | Sample ID | Solubility (mg/mL) |
|---|---|---|---|
| Water | 15 | 2162-74-1A | 30 |
| | 45 | 2162-74-1B | >100 |
| IPA:H$_2$O (9:1) | 15 | 2162-74-2A | 1.64 |
| | 45 | 2162-74-2B | 2.1 |
| MeOH:H$_2$O (9:1) | 15 | 2162-74-3A | 9.2 |
| | 45 | 2162-74-3B | 11.2 |
| Acetone:H$_2$O (9:1) | 15 | 2162-74-4A | 2.5 |
| | 45 | 2162-74-4B | 4.1 |
| THF:H$_2$O (9:1) | 15 | 2162-74-5A | 2.08 |
| | 45 | 2162-74-5B | 4.12 |
| MeOH | 15 | 2162-74-6A | ~1 |
| | 45 | 2162-74-6B | 2.73 |
| EtOH | 15 | 2162-74-7A | <1 |
| | 45 | 2162-74-7B | <1 |
| IPA | 15 | 2162-74-8A | <1 |
| | 45 | 2162-74-8B | <1 |
| EtOAc | 15 | 2162-74-9A | <1 |
| | 45 | 2162-74-9B | <1 |
| MeCN | 15 | 2162-74-10A | <1 |
| | 45 | 2162-74-10B | <1 |
| Acetone | 15 | 2162-74-11A | <1 |
| | 45 | 2162-74-11B | <1 |
| DCM | 15 | 2162-74-12A | <1 |
| | 45 | 2162-74-12B | 0.5 |
| Heptane | 15 | 2162-74-13A | <1 |
| | 45 | 2162-74-13B | <1 |
| TBME | 15 | 2162-74-14A | 3.0 |
| | 45 | 2162-74-14B | 28.9 |
| H$_2$O:MeOH:IPA (3:5.5:5) | 15 | 2162-74-15A | <1 |
| | 45 | 2162-74-15B | <1 |

Figure 32:
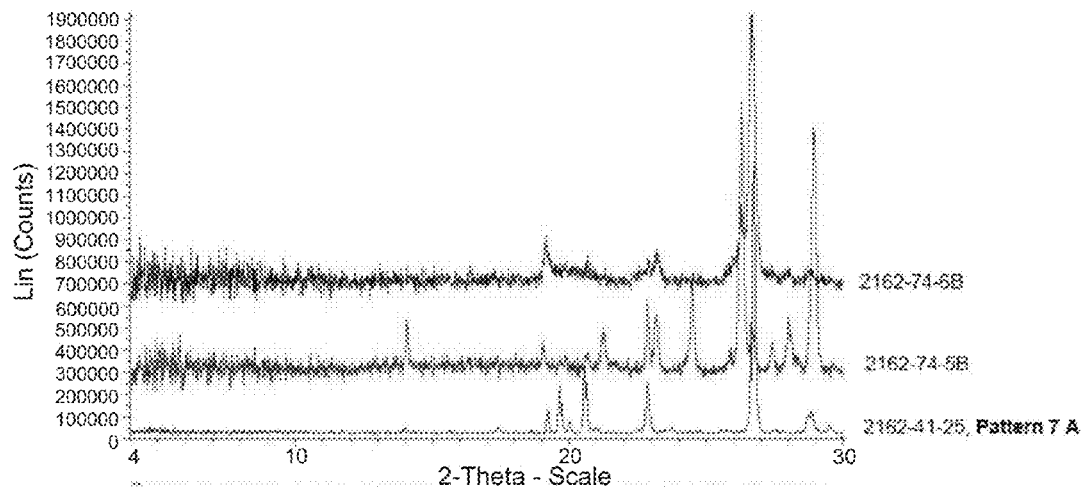
FIG. 32 is an image depicting X-ray powder diffraction (XRPD) pattern obtained for a crystalline form of the 1:1 fumarate salt of β-GPA after slow evaporation of solvent.
Figure 33:
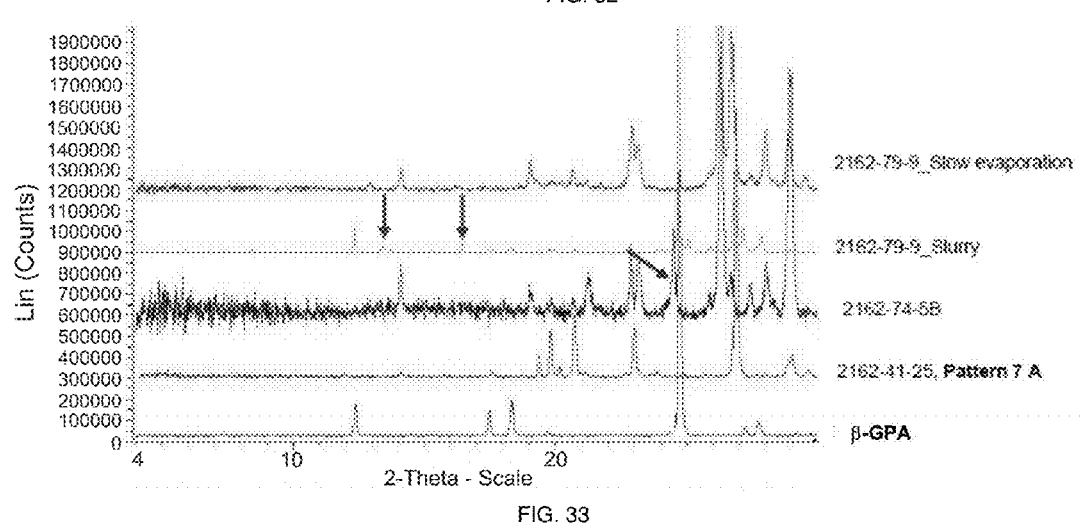
FIG. 33 is an image depicting an X-ray powder diffraction (XRPD) pattern obtained for a crystalline form of the 1:1 fumarate salt of β-GPA after slurry experiment in tetrahydrofuran:water (1:1) for 48 hours.

IPA = isopropanol; EtOH = ethano; EtOAc = ethyl acetate; DCM = dichloromethane; TBME = t-butylmethyl ether; MeOH = methanol; MeCN = Acetonitrile For ten of fourty-five samples the XRPDs after the slow evaporation of the filtrates from the slurry experiments resulted in Pattern 7A. Seventeen samples did not have enough solids for XRPD analysis. Sample 2162-74-5B resulted in a new crystalline form after slow evaporation of the filtrate and sample 2162-74-6B resulted in mixed XRPDs of Patterns 7A and 7B (FIG. 32).

β-GPA fumarate was slurried in tetrahydrofuran:water (1:1) for 48 hours. The filtrate was set up for evaporation at 45° C. under vacuum, and after overnight evaporation an off-white solid was obtained. Both the solids from the slurry and the solids obtained after slow evaporation were analyzed by XRPD (FIG. 33).

Pattern 7B, obtained by slow evaporation (45° C.) of the filtrate of β-GPA fumarate from the slurry experiment in tetrahydrofuran:water (1:1), was analyzed by DSC and ¹H-NMR. The DSC revealed the presence of an endotherm at 161° C. and also traces of Pattern 7A (the original β-GPA fumarate salt).

Anti-Solvent Addition Experiments

Anti-solvent addition experiments for 2:1 β-GPA fumarate were performed by using different anti-solvents. A given amount of 2:1 β-GPA fumarate was dissolved in the solvent at 50° C. Around 1 mL of ice cold anti-solvent was added to salt solution and continued stirring in ice bath for 2 hours followed by overnight stirring at 20° C. None of the experiments resulted in a new form of β-GPA fumarate.

Neat and Solvent Drop Grinding Experiments

Neat and solvent drop grinding experiments were also performed as a part of polymorph screening. Around 30 mg of the sample was ground in the presence of 20 μL of solvent (tetrahydrofuran, isopropanol, acetone, water, or t-butylmethylether) for 5 minutes using mortar and pestle. After grinding, the samples were analyzed by XRPD. All the experiments resulted in XRPDs that were identical to Pattern 7A.

Figure 34:
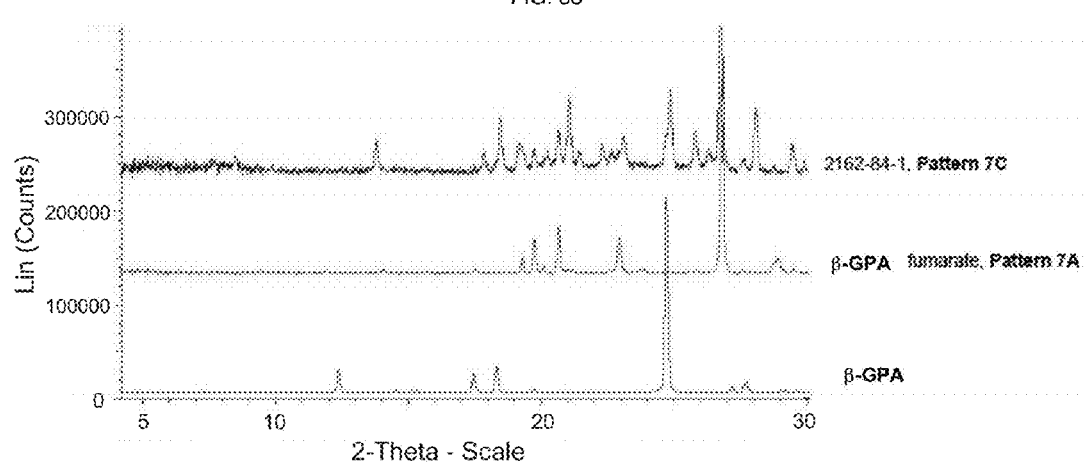
FIG. 34 is an image depicting X-ray powder diffraction (XRPD) pattern obtained for a polymorph of the 2:1 fumarate salt of β-GPA (Pattern 7C).
Figure 35:
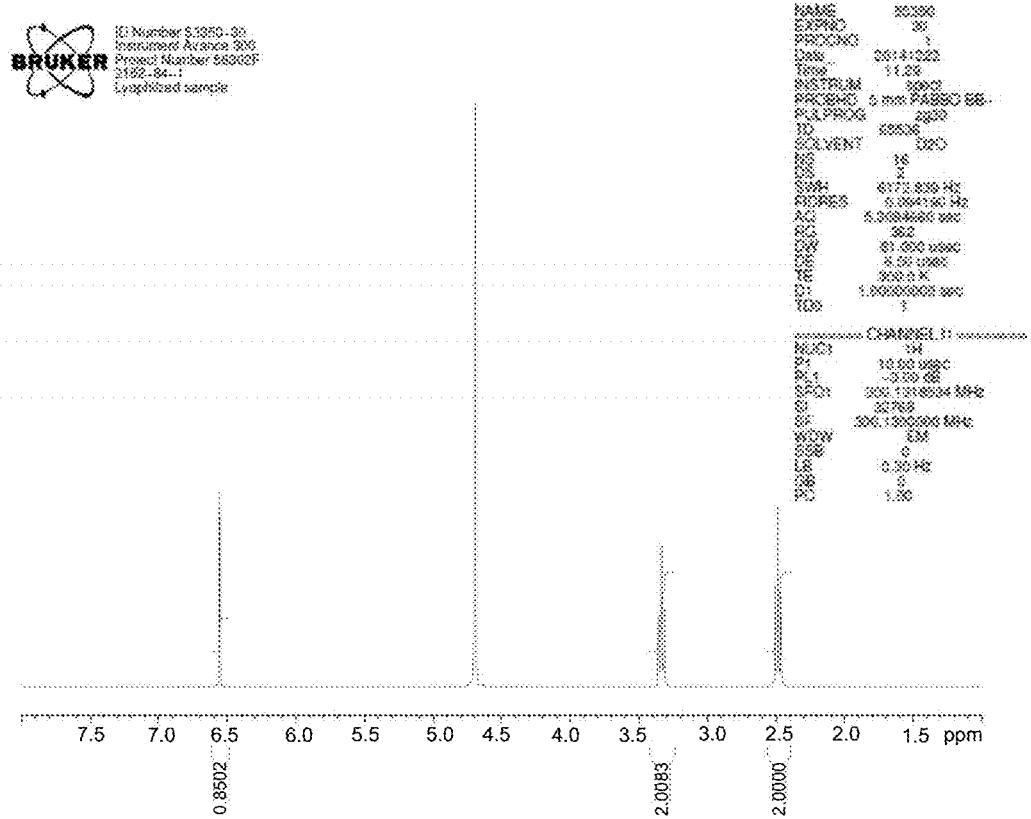
FIG. 35 is an image depicting a $^1$H NMR spectra of a polymorph of the 2:1 fumarate salt of β-GPA (Pattern 7C).

Attempts to Generate Amorphous Form of β-GPA Fumarate 1 g of 2:1 β-GPA fumarate was dissolved in 10 mL of water at 50° C. in a round bottom flask. The round bottom flask was placed in the dry ice/acetone cooling bath (−78° C.) until the sample solidified followed by lyophilization for 48 hours. A white solid was obtained which was analyzed by XRPD, DSC and ¹H-NMR. Sample ID: 2162-84-1. The XRPD analysis revealed a new XRPD pattern for 2162-84-1 (Pattern 7C) as shown in FIG. 34. The 1H-NMR of 2162-84-1 revealed that the solid obtained after lyophilization resulted in the formation of a polymorph of 2:1 β-GPA fumarate (FIG. 35). However, the microscopic image of the sample revealed the presence of some amorphous material. It could be possible that excess of fumaric acid after the formation of 2:1 β-GPA fumarate salt might have transformed to amorphous as seen in the microscopic image of the lyophilized sample To confirm the above hypothesis the following experiments (Table 25) were performed on the lyophilized sample (Pattern 7C):

TABLE 25

Results of Experiments Performed on 2:1 Fumarate Salt

| Sample ID | Experiment | Result |
|---|---|---|
| 2162-86-2 | 10 mg of Pattern 7C (lyophilized sample) and Pattern 7A were mixed in a vial and left undisturbed at room temperature (48 hours). The mixture was later analyzed by XRPD. | Pattern 7C to Pattern 7A |
| 2162-86-3 | Vial containing 20 mg of Pattern 7C was heated at 50° C. 5-10 minutes and later analyzed by XRPD. | Pattern 7C to Pattern 7A |
| 2162-86-4 | Vial containing 20 mg of Pattern 7C was placed in a humidity chamber with RH >95% for 48 hours. Sample was later analyzed by XRPD. | Pattern 7C to Pattern 7A |

TABLE 25-continued

Results of Experiments Performed on 2:1 Fumarate Salt

| Sample ID | Experiment | Result |
|---|---|---|
| 2162-87-1 | 50 mg of Pattern 7C was slurried in 0.2 mL of water. | Pattern 7C to Pattern 7A (within 10 minutes) |

Figure 36:
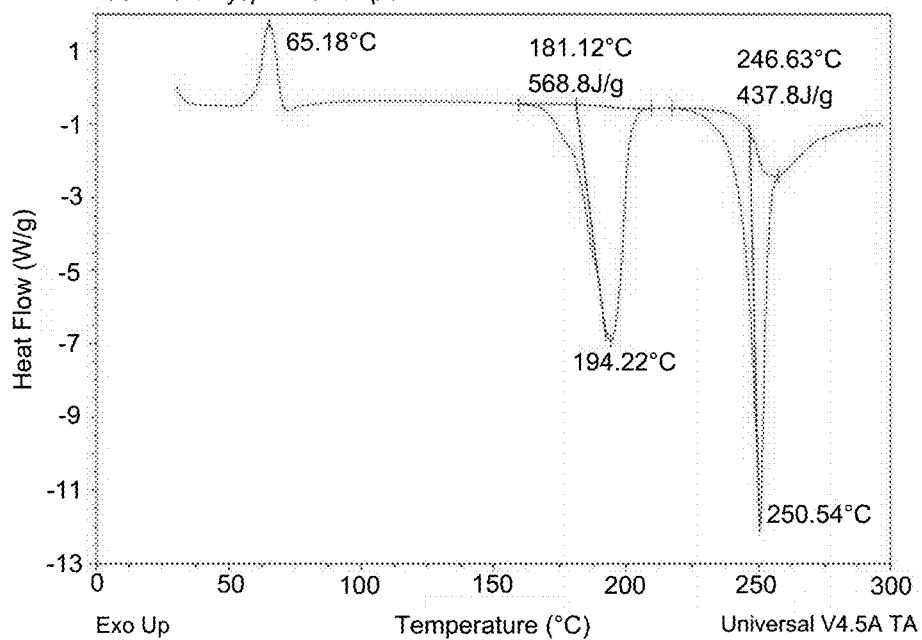
FIG. 36 is an image depicting a DSC thermogram obtained for a polymorph of the 2:1 fumarate salt of β-GPA (Pattern 7C).

The DSC of the lyophilized sample revealed the presence of an exothermic event (possible recrystallization or solid phase transformation) followed by two endothermic events (FIG. 36). The first endothermic event could be the 2:1 β-GPA fumarate salt followed by the melting of possible side product which might have formed after the melting of 2:1 β-GPA fumarate salt.

1 g of 2:1 β-GPA fumarate was dissolved in 10 mL of water at 50° C. and was placed under vacuum at 100° C. for fast evaporation. Sample ID: 2162-84-2. The solid obtained was analyzed by XRPD and sample was found to retain the original β-GPA fumarate powder pattern (Pattern 7A).

Temperature Cycling Experiments

The following (Table 26) experiments were performed to isolate possible polymorphic forms of 2:1 β-GPA fumarate.

TABLE 26

Temperature Cycling Results

| Sample ID | Experiment | Result |
|---|---|---|
| 2162-84-3 | Vial containing 50 mg of β-GPA fumarate was placed in vacuum oven at 130° C. for 2 hours and brought to room temperature (RT) and placed back in the oven at 130° C. for 48 hours and again to RT. | Pattern 7A |
| 2162-84-4 | Vial containing 50 mg of β-GPA fumarate was placed on the hot plate at 50° C. for 2 hours and brought to room temperature and placed back in the oven at 50° C. for 48 hours and again to RT. | Pattern 7A |
| 2162-84-5 | Vial containing 50 mg of β-GPA fumarate was placed in the dry ice-acetone mixture for 30 minutes and was brought to room temperature and again placed back in the dry ice-acetone mixture for additional 30 min and again to RT. | Pattern 7A |
| 2162-84-6 | 50 mg of β-GPA fumarate was heated in a vial to 150° C. and brought to room temperature. This cycle was repeated three times and the sample was analyzed later by XRPD. | Pattern 7A |
| 2162-84-7 | 50 mg of β-GPA fumarate was heated in an aluminum cup to 165° C. and immediately placed in dry ice/acetone cooling bath for 15 min. Later, the sample was analyzed later by XRPD. | The started turned yellow to brown in color upon heating. Pattern 7D |

Heating of β-GPA fumarate (2162-84-7) at 160-165° C. resulted in a yellow to brownish solid (possible side reaction followed by decomposition) which was further analyzed by 1H-NMR and XRPD.

Several cooling experiments were conducted all of which resulted in no form change, or resulted in the isolation of fumaric acid-β form or a mixture of fumaric acid-α and β forms concomitantly.

Lyophilization Experiments

Around 264 mg of β-GPA and 118 mg fumaric acid were dissolved in 10 mL of water at 65° C. The solution was solidified using dry ice-acetone mixture followed by freeze drying for 48 hours. This resulted in the isolation of a polymorph of the 2:1 salt.

Diffusion Experiments

Diffusion experiments for 2:1 β-GPA fumarate were set up dissolving around 1 g of the salt in 10 mL of water. For every diffusion experiment, 1 mL of the above solution was dispensed in a small 4 mL vial and was placed in a 20 mL scintillation vial containing the different solvents. None of the experiments resulted in a new form of β-GPA fumarate.

Reverse Anti-Solvent Addition Experiments

Reverse anti-solvent addition experiments for 2:1 β-GPA fumarate were performed by using different anti-solvents. A given amount of 2:1 β-GPA fumarate was dissolved in 1 mL of solvent at 40° C. This solution was added to a known amount of an anti-solvent and stirred at room temperature until solids precipitated out. None of the experiments resulted in a new form of β-GPA fumarate.

Summary of Polymorph Screening Experiments

Based on the available data obtained from the screening experiments, Pattern 7A appears to be the most stable form.

Example 17. Raman Spectroscopy of 2:1 β-GPA Fumarate Salt

Figure 37:
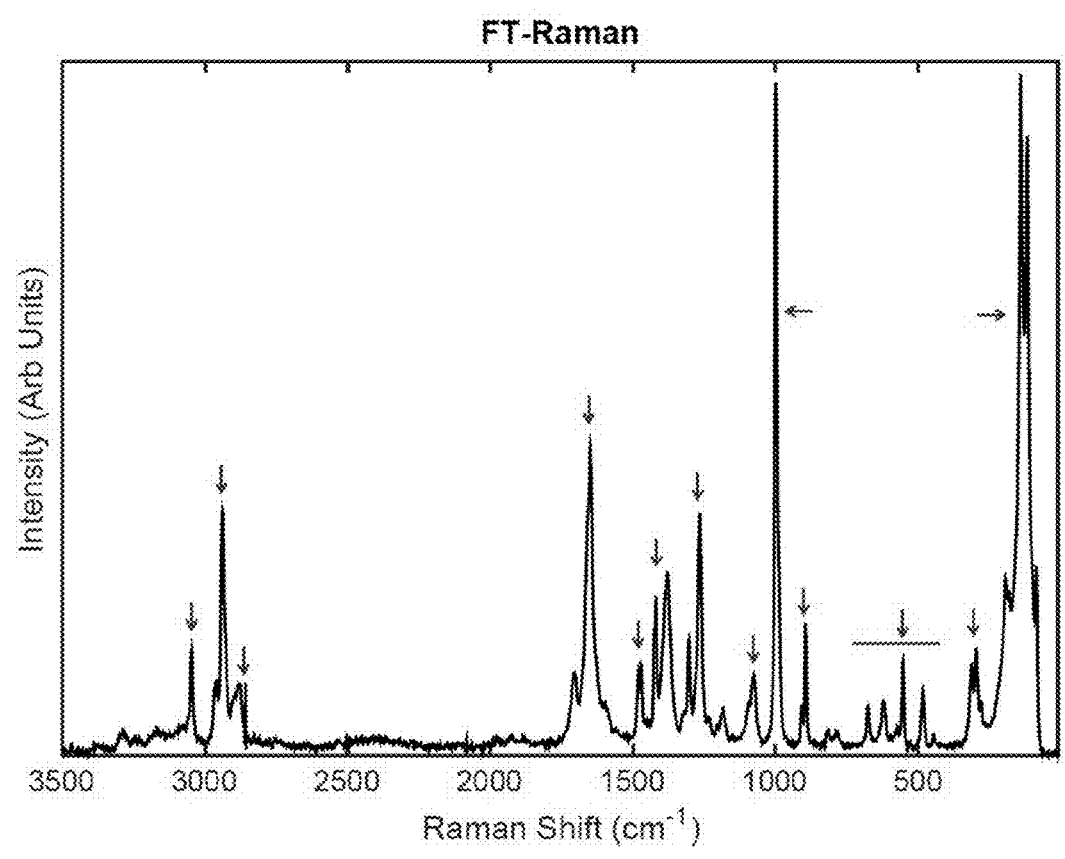
FIG. 37 is an image depicting the Raman spectra of a crystalline form of the 2:1 fumarate salt of β-GPA (Pattern 7A).
Figure 38:
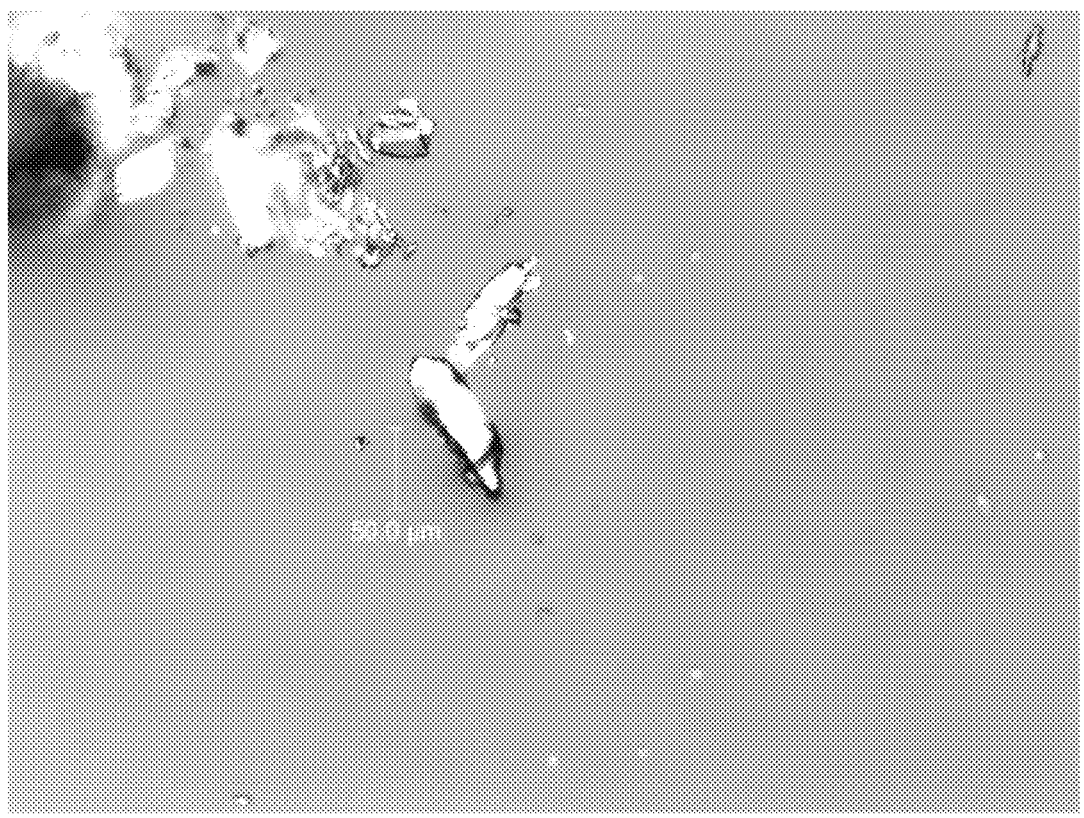
FIG. 38 is an image of crystals of the 2:1 fumarate salt of β-GPA under a polarized microscope (Pattern 7A).

Raman spectroscopy of the 2:1 β-GPA fumarate salt (Pattern 7A) was carried out on a Bruker IFS 66V/S FT-IR/FT-Raman spectrometer equipped with a 1064 nm laser (FIG. 37). The peak list of the Raman spectra is listed in Table 27.

TABLE 27

Raman Spectra Peak List
2:1 fumarate β-GPA fumarate salt

| Raman Shift (cm-1) | Functional group |
|---|---|
| 3300.48 | COOH/NH |
| 3188.58 | |
| 3049.73 | C=C—H |
| 2941.74 | CH2 |
| 2886.78 | |
| 1713.28 | C=O, υ(C=C), υ(C=N) |
| 1653.49 | |
| 1483.79 | N=N-R |
| 1421.11 | N=N |
| 1382.54 | |
| 1305.4 | Alkene In-plane bending |
| 1268.76 | |
| 1190.66 | Alkene out of plane bending |
| 1084.59 | C—C (acid) |
| 997.81 | |
| 896.56 | υ(O—O) |
| 681.53 | Aliphatic chain vibrations |
| 625.6 | |
| 555.21 | |
| 486.79 | δ(CC) aliphatic chains |

Example 18. Single Crystal Analysis of 2:1 β-GPA Fumarate Salt

Figure 42A:
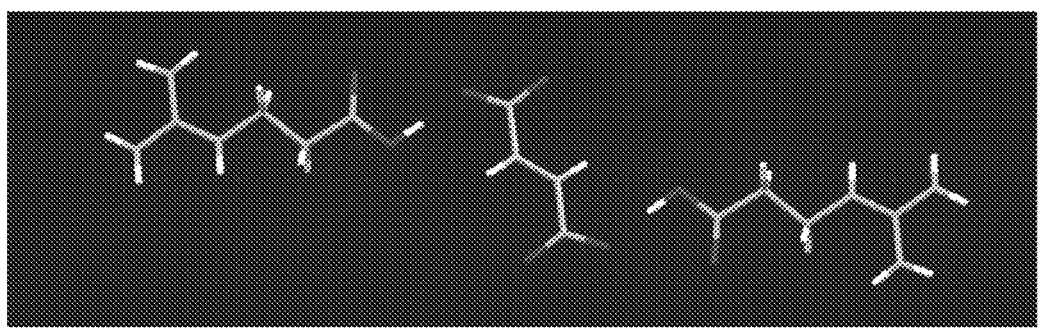
FIGS. 42A-D are images depicting three-dimensional representations of the unit cell of a crystalline form of the 2:1 fumarate salt of β-GPA based on single crystal analysis (Pattern 7A).
Figure 42B:
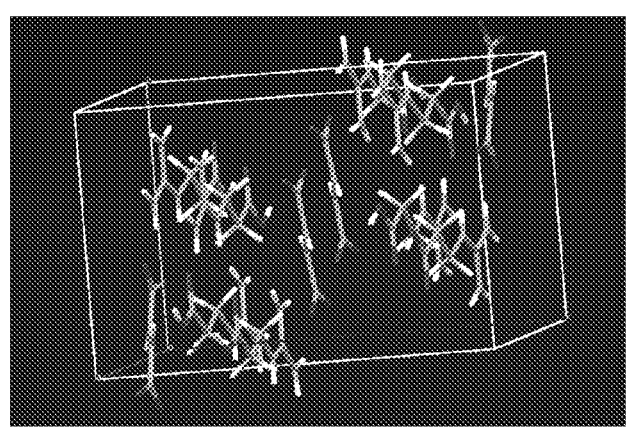

SCXRD analysis of a crystal form of the 2:1 fumarate salt confirms the 2:1 stoichiometric between the β-GPA and fumaric acid. 2:1 fumarate salt of β-GPA crystallizes in monoclinic crystal system with $P2_1/n$ space group. The asymmetric unit consists of two β-GPA and one fumaric acid molecules (FIG. 42A) whilst, the unit cell consists of four fumaric acid and eight β-GPA molecules (FIG. 42B). SCXRD data was collected at room temperature (25° C.).

Figure 42C:
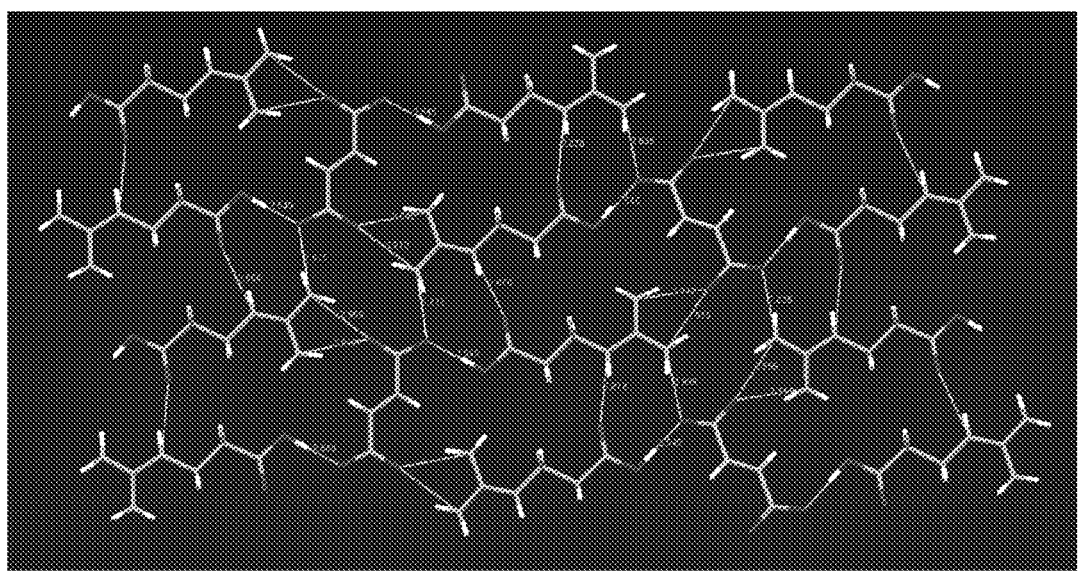

Unit Cell Parameters:
Crystal System: Monoclinic
Space Group: P $2_1$/n
a=12.4541(5) A
b=9.5447(4) A
c=14.4013(6) A
α=90°, β=100.469(2)°, γ=90°
Cell Volume: 1683.39 Å$^3$ The carboxylates moieties of two fumaric acid and two NH$_2$ moieties of two β-GPA molecules interact via O...NH hydrogen bonding thus, forming a four membered ring. The carboxylates moieties of fumaric acid also hydrogen bond with another adjacent β-GPA molecule through O...OH with a bond distance of 2.545 Å. The carboxylic acid moiety of the same β-GPA molecule interacts with the neighboring β-GPA molecule via O...NH hydrogen bond (2.835 Å). FIG. 42C below describes the several other hydrogen bonding interactions with the bond distances.

Figure 42D:
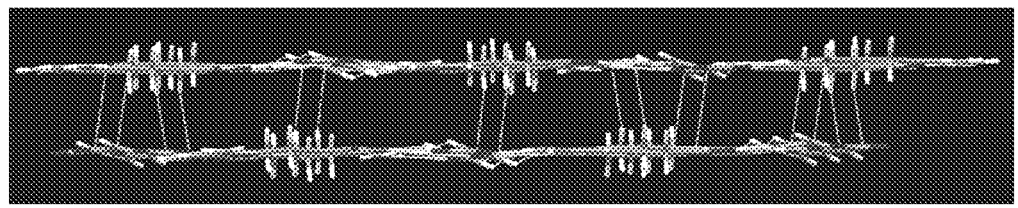

The overall hydrogen bonding between β-GPA and fumaric acid results in the formation of 2-dimensional planar sheets which interacts via weak Van der Waals forces (FIG. 42D).

Example 19. Calculated XRPD Based on Single Crystal Analysis

As shown in FIGS. 43A-C, the experimental XRPD pattern (NP-2162-163-3) of the 2:1 fumarate salt was found to be in good agreement with the calculated pattern from the single crystal (NP-2162-169-1, which was grown from NP-2162-163-3). The peak lists for the calculated and experimental XRPD pattern of the single crystal of the 2:1 fumarate salt is shown in Table 28 and 29.

TABLE 28

Peak list of NP-2162-163-3
(Calculated from SCXRD).

| Angle 2-Theta ° | Intensity % | d value Angstrom |
|---|---|---|
| 17.47 | 1.8 | 5.071 |
| 19.26 | 6.8 | 4.604 |
| 19.71 | 3.3 | 4.502 |
| 20.67 | 5.3 | 4.294 |
| 22.90 | 9.3 | 3.880 |
| 25.91 | 2.5 | 3.436 |
| 26.78 | 100 | 3.327 |
| 27.51 | 3.2 | 3.240 |
| 28.73 | 2.7 | 3.105 |
| 29.12 | 1.8 | 3.065 |
| 31.16 | 2.5 | 2.868 |
| 33.04 | 1.7 | 2.709 |
| 33.98 | 3.5 | 2.636 |
| 35.27 | 3.1 | 2.542 |
| 39.05 | 2.7 | 2.305 |
| 23.82 | 2.9 | 3.732 |
| 24.09 | 3.2 | 3.691 |
| 20.97 | 5.7 | 4.234 |

TABLE 29

Peak list of 2162-64-1.

| Angle 2-Theta ° | Intensity % | d value Angstrom |
|---|---|---|
| 11.73 | 12.1 | 7.537 |
| 13.92 | 13.8 | 6.359 |

TABLE 29-continued

Peak list of 2162-64-1.

| Angle 2-Theta ° | Intensity % % | d value Angstrom |
|---|---|---|
| 17.38 | 15.2 | 5.100 |
| 19.15 | 24.7 | 4.630 |
| 19.58 | 45.7 | 4.530 |
| 19.99 | 18.7 | 4.439 |
| 20.53 | 64.9 | 4.323 |
| 20.97 | 17 | 4.233 |
| 22.83 | 31.6 | 3.892 |
| 23.69 | 13.4 | 3.753 |
| 25.53 | 13.5 | 3.487 |
| 26.69 | 100 | 3.338 |
| 27.48 | 12.1 | 3.243 |
| 28.64 | 26.4 | 3.115 |
| 29.02 | 11.8 | 3.074 |
| 31.07 | 18.1 | 2.876 |
| 35.25 | 13 | 2.544 |
| 38.94 | 14.8 | 2.311 |

Example 20. Capsule Fill Evaluation of 2:1 Succinate Salt

The purpose of the following experiments was to determine the maximum allowable fill weight of β-Guanidiopropionic Acid into size 0 capsules and resulting disintegration behavior. Jet milling and roller compaction feasibility were also performed to determine the effect on resulting net capsule fill weight. The free acid and the 2:1 succinate salt form of β-GPA were both evaluated.

The two β-GPA samples evaluated are given in Table 30.

TABLE 30

Samples evaluated.

| Description From Label | Lot |
|---|---|
| 3-Guanidinopropionic Acid | Batch #10 |
| β-Guanidinopropionic Acid Succinate Salt | ELS-104-76-25 |

Hand Fill Assessment

Both lots of material were hand filled using a Torpac size 0 capsule loader into size 0 Swedish orange V-cap capsules. Two hand filling methods were evaluated. Free flow capsules were prepared by gravity filling, without the use of tamping, until the bottom section of the size 0 capsule was filled to the brim. Excess material was gently scraped using a spatula. Tamp filled capsules were prepared by constantly filling and then tamping the material until reaching the brim of the size 0 capsule bottom. A total of N=5 capsules were filled for each lot for each method. The average net fill weight results are given below in Table 31.

TABLE 31

Net fill weight of size 0 capsule filled with API

| API | Lot Number | Fill Method | Average Net Weight (mg) |
|---|---|---|---|
| 3-Guanidinopropionic Acid | 1366-1-2-A | Free Flow | 207.0 |
|  | 1366-1-2-B | Tamp | 471.6 |
| β-Guanidinopropionic Acid Succinate Salt | 1366-1-7-A | Free Flow | 320.2 |
|  | 1366-1-7-B | Tamp | 451.3 |

As expected capsules filled by the tamp method had a significantly higher fill amount compared those which were free flow filled. However, it should be noted that these methods of filling will not be represent of performance on an automated encapsulation machine. Based on the data it can be determined that the Succinate Salt form allowed for better free flow filling into capsules allowing for 113 mg more material to be filled into a size 0 capsule. Tamp filling however both forms performed relatively the same.

Roller Compaction Feasibility

Roller compaction feasibility was performed by producing slugs using a single station hand press then carefully hand milling those slugs so that all granules were small enough to pass through a size US 18 mesh. These granules were then filled into size 0 capsules by both the free flow and tamp method. A total of N=5 capsules were filled for each lot for each method. The average net fill weight results are given below in Error! Reference source not found.2.

TABLE 32

Net fill weight of size 0 capsules filled with roller compacted API

| API | Lot Number | Fill Method | Average Net Weight (mg) |
|---|---|---|---|
| 3-Guanidinopropionic Acid | 1366-1-7-A | Free Flow | 303.6 |
|  | 1366-1-7-B | Tamp | 568.2 |
| β-Guanidinopropionic Acid Succinate Salt | 1366-1-14-A | Free Flow | 335.4 |
|  | 1366-1-14-B | Tamp | 574.6 |

While it does appear from the data set that roller compaction of the free acid API does provide a benefit to capsule filling it should be noted that slugs produced in this fashion had an extremely low tensile strength. Slugs produced using up to 2000 psi (36 mPa, 9 kN) worth of force were so soft that a proper hardness value was not able to be obtained when tested using a tablet hardness tester. The calculated solid fraction for these slugs was 74%. The historical range for solid fraction of acceptable ribbons for roller compaction is between 50% to 80%. Slugs were milled by hand as any other method would have been too energy intensive and most likely cause any granules produced to be destroyed. That being said maximum capsule fill weight increased by roughly 100 mg for both free flow and tamp filled capsules.

The same issue was not seen when compressing the succinate salt form of β-GPA. Slugs produced around 1500 PSI produced slugs hard enough to be tested for hardness. The resulting slug parameters can be seen in Table 33.

TABLE 33

Slug Parameters for β-Guanidinopropionic Acid Succinate Salt

|  | Tablet Weight (mg) | Tablet Thickness (mm) | Tablet Hardness (kp) | Compression Force PSI | Compression Stress (MPa) | Tensile Strength (MPa) | Calculated Solid Fraction |
|---|---|---|---|---|---|---|---|
|  | 1505.7 | 4.77 | 6.8 | 2000 | 36 | 0.50 | 0.85 |
|  | 1521.4 | 5.2 | 4.4 | 1500 | 27 | 0.30 | 0.79 |
|  | 1545.2 | 5.28 | 4.3 | 1500 | 27 | 0.29 | 0.79 |
|  | 1493.6 | 5.09 | 5.1 | 1500 | 27 | 0.35 | 0.79 |
|  | 1502.1 | 5.12 | 3.7 | 1500 | 27 | 0.25 | 0.79 |
| Average | 1513.60 | 5.09 | 4.86 | 1600.00 | 28.67 | 0.34 | 0.80 |
| Std | 20.34 | 0.19 | 1.19 | 223.61 | 4.01 | 0.10 | 0.03 |
| RSD | 1.34 | 3.82 | 24.55 | 13.98 | 13.98 | 28.89 | 3.41 |

However, it should be noted that slugs produced on the single station were extremely difficult to remove. This high ejection force was due to the material sticking and smearing along the die wall. The free flow maximum capsule fill weight for the salt form remained relatively the same after roller compaction however the tamp filled maximum capsule fill weight increased by 120 mg.

Jet Milling Feasibility

Jet Milling feasibility was performed using a Jet-O-Mizer 2 inch jet mill. Roughly 5 grams of material was milled for each form of β-GPA. The parameters used and the resulting yields can be seen in Table 34.

TABLE 34

Jet Mill Feasibility Parameters

| Lot Number | 1366-1-11 | 1366-1-12 |
|---|---|---|
| API | β-Guanidinopropionic Acid Succinate Salt | 3-Guanidinopropionic Acid |
| Supply Air | 140 | 140 |
| Grinding Nozzle Pressure | 100 | 100 |
| Pusher Nozle Pressure | 80 | 80 |
| Vibratory Feeder Setting | 3 | 3 |
| Amount before milling (g) | 8.1477 | 6.6893 |
| Amount after milling (g) | 5.2610 | 4.4165 |
| Yield (%) | 64.6 | 66.0 |

The milled API was hand filled into size 0 capsules using the free flow and tamp filled method. Resulting net average capsule fill weights are given in Table 35.

TABLE 35

Net fill weight of size 0 capsules filled with et milled API

| API | Lot Number | Fill Method | Average Net Weight (mg) |
|---|---|---|---|
| 3-Guanidinopropionic Acid | 1366-1-13-A | Free Flow | 119.2 |
|  | 1366-1-13-B | Tamp | 356.8 |
| β-Guanidinopropionic Acid Succinate Salt | 1366-1-14-A | Free Flow | 118.0 |
|  | 1366-1-14-B | Tamp | 426.4 |

Jet milling of the API caused a decrease in the maximum fill of size 0 capsule. This is most likely because the jet milling process can produce powders that are often highly cohesive and have poor flowability properties, as well as lower bulk density.

DSC and XRPD were performed on both API's before and after jet milling in order to determine if any change in material structure occurred due to the milling process.

Figure 44:
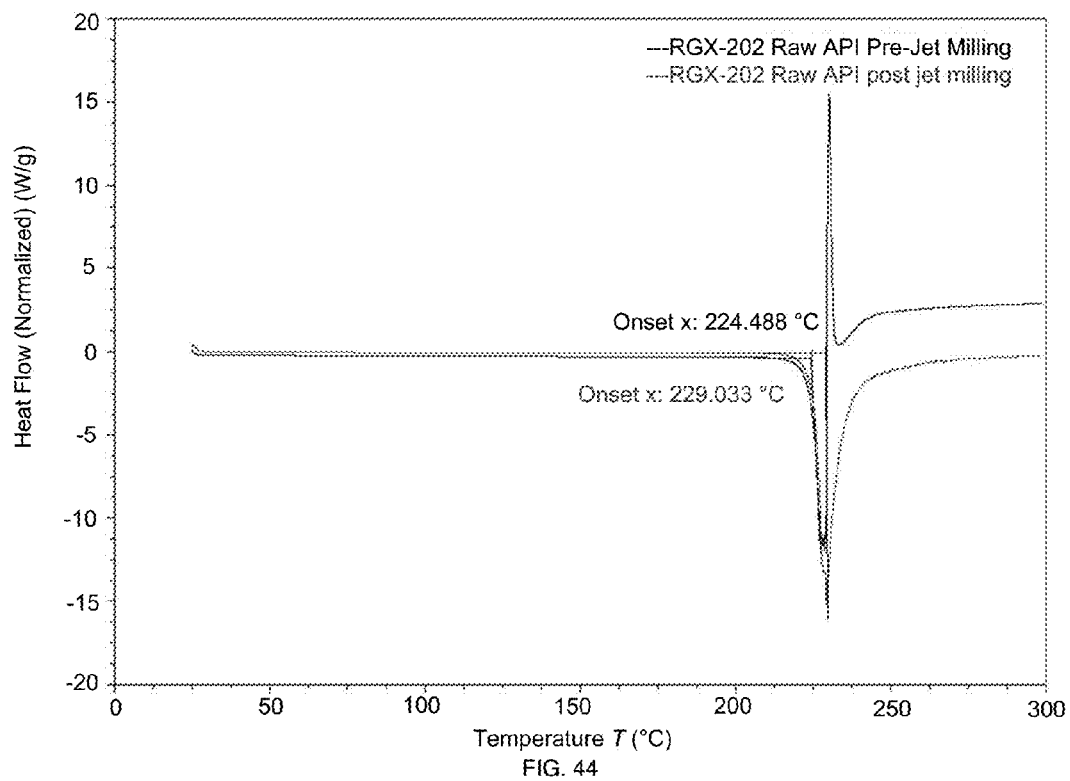
FIG. 44 is an image depicting an overlay of the DSC of β-GPA Pre and Post Jet Milling.
Figure 45:
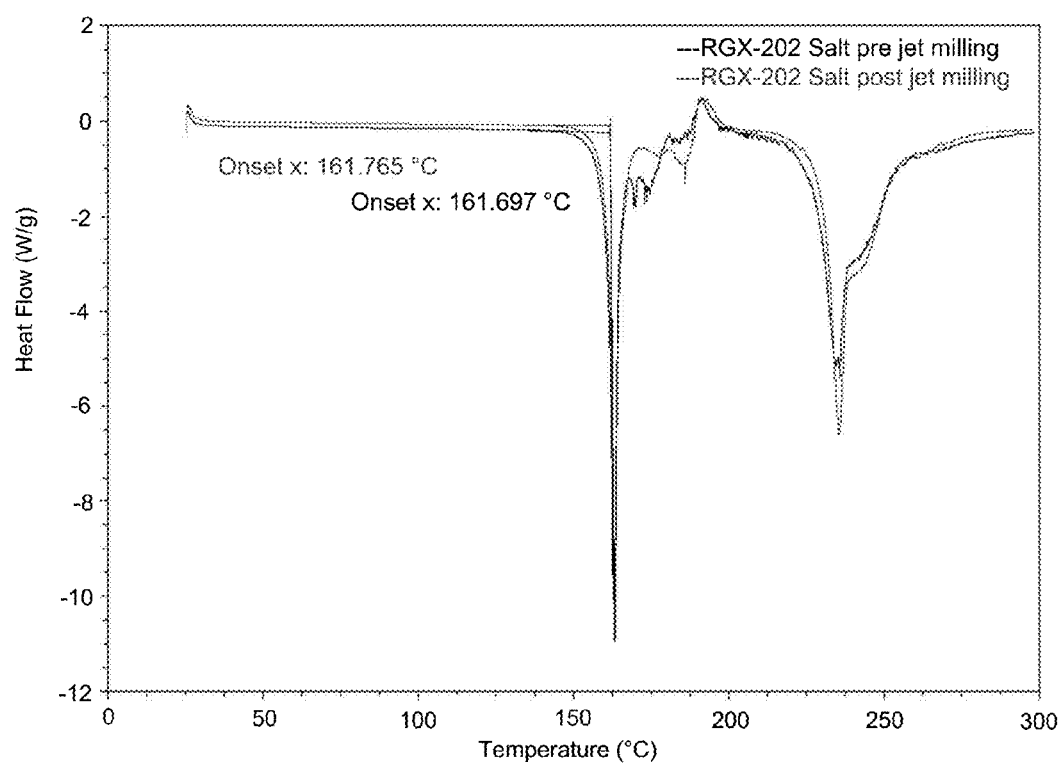
FIG. 45 is an image depicting an overlay of the DSC of β-GPA succinate salt Pre and Post Jet Milling.

Looking at the traces there was no change in the DSC trace for either API. There is a degradation peak present on the DSC for the non-salt form before jet milling which does not appear to on the post jet milling trace, but this is most likely degradation. The overlay DSC traces can be seen in FIG. 44 and FIG. 45.

Figure 46:
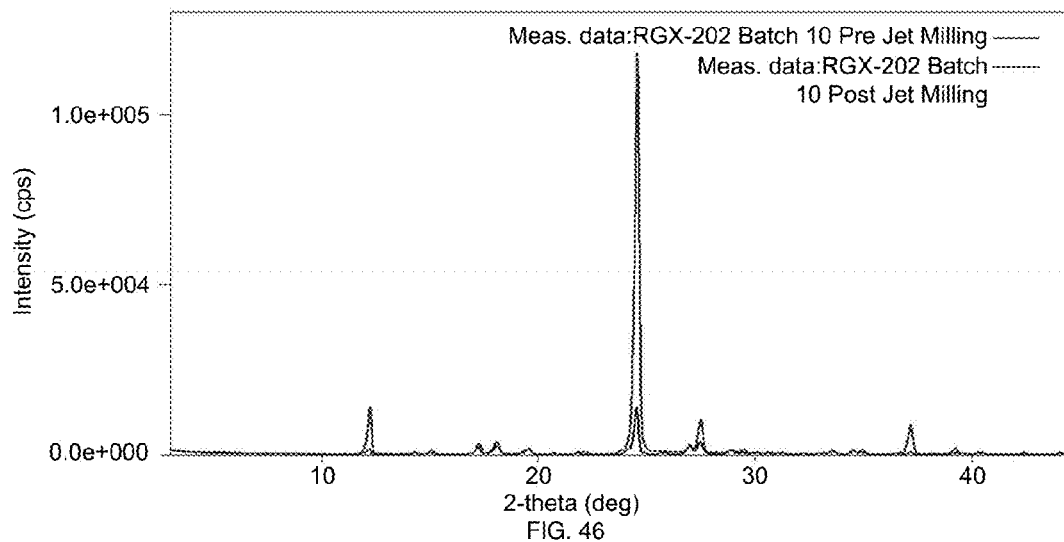
FIG. 46 is an image depicting the PXRD trace of β-GPA Pre and Post Jet Milling.
Figure 47:
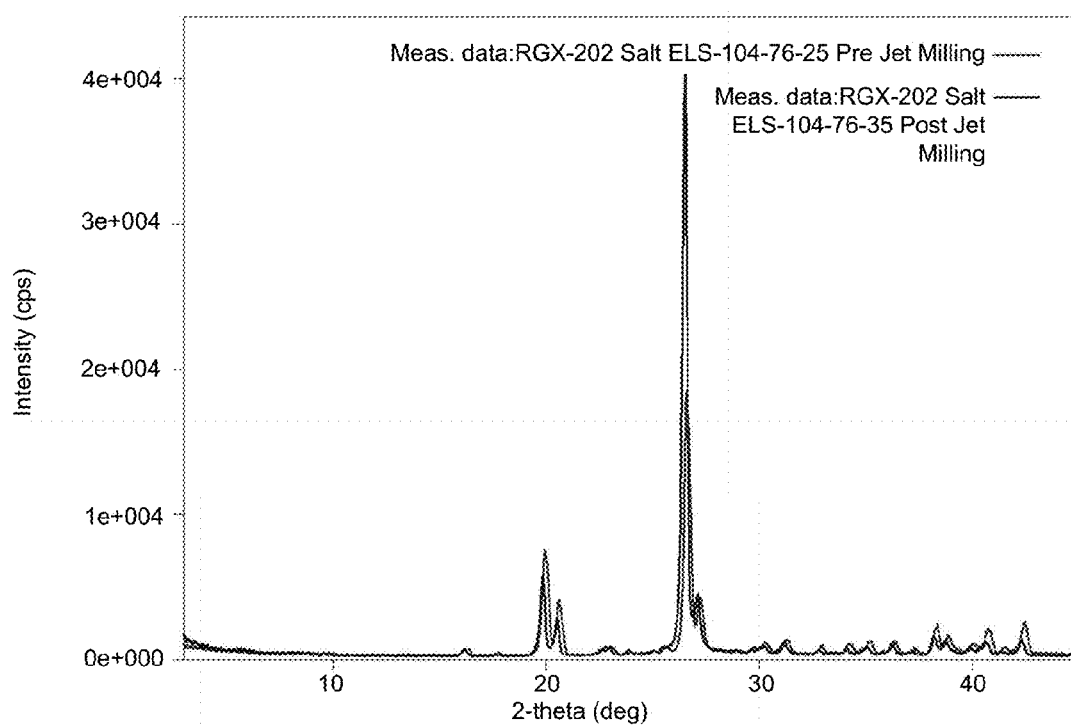
FIG. 47 is an image depicting the PXRD trace of β-GPA succinate salt Pre and Post Jet Milling.

The XRPD traces for each API also remained unchanged. The intensities of the peaks do differ between pre and post jet milling, however this most likely due to preferred orientation and the peaks are still consistent with one another. The PXRD traces can be seen in FIGS. 46 and 47.

Disintegration Evaluation

Filled capsules from each feasibility study were tested for disintegration in water. Water was brought to a temperature of 37±3° C. before beginning testing. Results of these disintegration trials are giving below in Table 36.

TABLE 36

Disintegration Results

| Lot | Description | API | Disintegration Time (min:sec) | Initial Temp (° C.) | Final Temp (° C.) | Observation |
|---|---|---|---|---|---|---|
| 1366-1-2-A | Free Flow | 3-Guanidinopropionic Acid | 03:44 | 36.9 | 37.0 | All solids dissolved soon as capsule breached |
| 1366-1-2-B | Tamp Fill | 3-Guanidinopropionic Acid | 03:44 | 36.9 | 37.0 | All solids dissolved soon as capsule breached |
| 1366-1-5-A | RC, Free Fill | 3-Guanidinopropionic Acid | 03:44 | 36.9 | 37.0 | All solids dissolved soon as capsule breached |

TABLE 36-continued

Disintegration Results

| Lot | Description | API | Disintegration Time (min:sec) | Initial Temp (° C.) | Final Temp (° C.) | Observation |
|---|---|---|---|---|---|---|
| 1366-1-5-B | RC, Tamp Fill | 3-Guanidinopropionic Acid | 04:32 | 36.9 | 37.0 | Some Small Granules observed during capsule breaking |
| 1366-1-7-A | Free Flow | β-Guanidinopropionic Acid Succinate Salt | 03:59 | 38.1 | 38.0 | All solids dissolved soon as capsule breached |
| 1366-1-7-B | Tamp Fill | β-Guanidinopropionic Acid Succinate Salt | 04:17 | 38.1 | 38.0 | All solids dissolved soon as capsule breached |
| 1366-1-13-A | JM, Free Flow | 3-Guanidinopropionic Acid | 05:27 | 38.1 | 38.0 | All solids dissolved soon as capsule breached |
| 1366-1-13-B | JM, Tamp Fill | 3-Guanidinopropionic Acid | 05:27 | 38.1 | 38.0 | All solids dissolved soon as capsule breached |
| 1366-1-14-A | JM, Free Flow | β-Guanidinopropionic Acid Succinate Salt | 02:39 | 36.9 | 37.1 | All solids dissolved soon as capsule breached |
| 1366-1-14-B | JM, Tamp Fill | β-Guanidinopropionic Acid Succinate Salt | 03:09 | 36.9 | 37.1 | All solids dissolved soon as capsule breached |
| 1366-1-15-A | RC, Free Flow | β-Guanidinopropionic Acid Succinate Salt | 02:53 | 36.9 | 37.1 | All solids dissolved soon as capsule breached |
| 1366-1-15-B | RC, Tamp Fill | β-Guanidinopropionic Acid Succinate Salt | 02:58 | 36.9 | 37.1 | Some Small Granules observed during capsule breaking |

RC = Roller Compacted granules,
JM = Jet milled material

There were not significant differences in the disintegration times of the capsules produced. The only observations made were that some of the capsules which contained roller compacted material did have small granules escape after the capsule breaching. These granules dissolved within 30 seconds of being released in the disintegration media.

Compression Profile Evaluation

Compression profiling was also performed on both the free base and the salt form of the API. A standard formulation containing plastic diluent, brittle diluent, disintegrant and lubricant was evaluated at a loading of 25% and 50% API. The diluent level was adjusted accordingly, but the ratio of plastic to brittle filler was set a 1:1. It was decided to use a representative tablet formulation to perform compression profiling to mitigate the cohesion and sticking issues seen in the free base and the salt form during the roller compaction feasibility evaluation. Table 37 details the formulation compositions tested.

TABLE 37

Compression Profiling Formulations

| Component | Description | 1366-1-18 % (w/w) | 1366-1-19 % (w/w) | 1366-1-20 % (w/w) | 1366-1-20 % (w/w) |
|---|---|---|---|---|---|
| 3-GPA | API | 50.0 | 25.0 | | |
| β-GPA Salt | API | | | 50.0 | 25.0 |
| Avicel PH200 | Plastic Diluent | 22.0 | 34.5 | 22.0 | 34.5 |
| Lactose 316 | Brittle Diluent | 22.0 | 34.5 | 22.0 | 34.5 |
| Croscarmellose Sodium | Disintegrant | 5.0 | 5.0 | 5.0 | 5.0 |
| Mag Stearate | Lubricant | 1.0 | 1.0 | 1.0 | 1.0 |

These blends were then compressed into 100 mg compacts using 0.25-inch flat faced tooling at increasing compaction pressures. A total of N=3 compacts were produced at each compaction pressure and were measured for weight, thickness and hardness. The compression stresses used were calculated by dividing the force applied to the compact by the surface area of the 0.25 in flat faced tooling. The tensile strength of the compacts was calculated using the equations derived for flat faced tablets. For each formulation, a tabletability (tensile strength vs. compression pressure) was generated. For the purposes of this study the tabletability profile was examined to determine the compaction pressure required in order to produce a tablet of acceptable tensile strength. Historically a tablet with a tensile strength of 2.0 Mpa is sufficient to both withstand friability and to not impact disintegration and dissolution.

Figure 48:
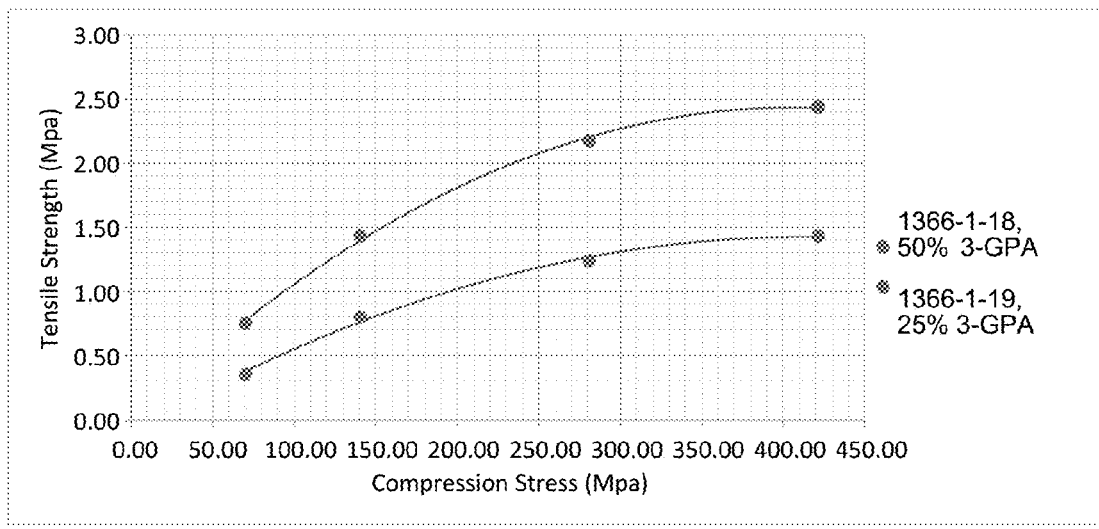
FIG. 48 is a graph depicting the tabletability of β-GPA.

FIG. 48 shows the tabletability profile for the free base form of β-GPA. It is observed that the 50% API loading formulation seems to be incapable of reaching a tablet with 2.0 Mpa even at upwards of 400 mPa of compression force. As the API loading is reduced to 25% API the tabletability of the formulation increases. It would still require roughly 235 Mpa of compression stress to produce a tablet of 2.0 Mpa of strength at the 25% loading.

Figure 49:
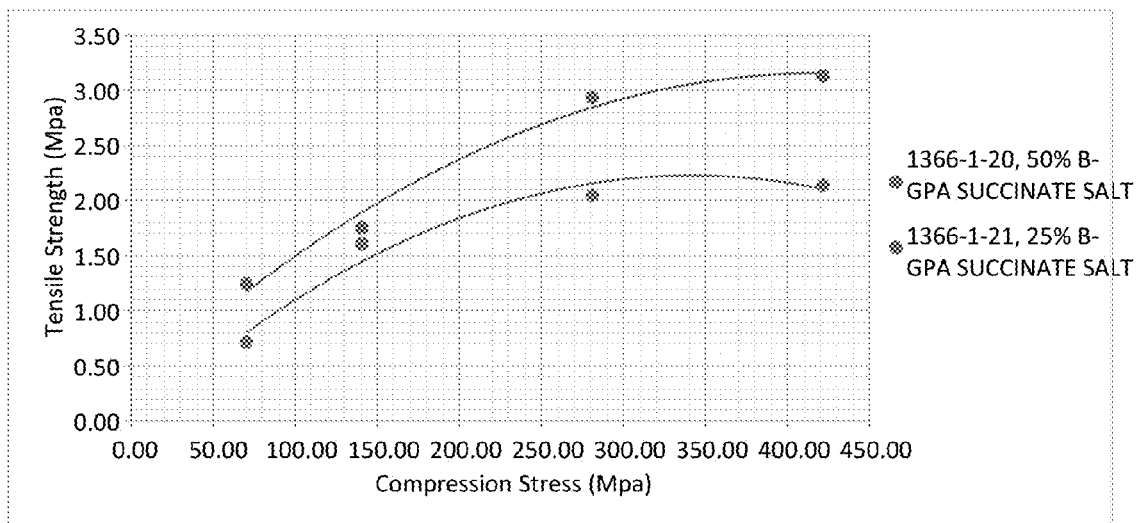
FIG. 49 is a graph depicting the tabletability of β-GPA succinate salt.

FIG. 49 shows the tabletability profile for the β-GPA salt form. Like the free base, tabletability improves with additional diluent in the formulation when moving from a 50% to a 25% API loading. For the 50% API formulation, an estimated 230 Mpa of compaction pressure or a compaction force of 34.8 kN would be required to produce a tablet of 2.0 Mpa tensile strength. At 25% API loading the compaction pressure required is reduced to 150 Mpa or a compaction force of 22.7 kN. This tablet would provide a 250 mg dose of the API salt form. During compaction, there were no signs of "sticking" to the die wall during ejection.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features herein before set forth.

What is claimed is:

1. A pharmaceutically acceptable salt of β-guanidinopropionic acid, wherein said pharmaceutically acceptable salt is a 2:1 fumarate salt wherein said salt is crystalline and has at least one peak at diffraction angle 2θ (°) selected from 27±0.5, 20±0.5, 20.5±0.5 or 23.5±0.5 as measured by X-ray diffractometry or calculated from X-ray diffractometry.

2. The pharmaceutically acceptable salt of claim 1 comprising less than 40% by weight of amorphous compound.

3. The pharmaceutically acceptable salt of claim 1 having an endothermic onset at about 187° C. and/or 251° C. in differential scanning calorimetry (DSC) profile.

4. The pharmaceutically acceptable salt of claim 1 having at least one peak at diffraction angle 2θ (°) of 27±0.5 as measured by X-ray diffractometry or calculated from X-ray diffractometry.

5. The pharmaceutically acceptable salt of claim 1 having at least one peak at diffraction angle 2θ (°) of 20±0.5 as measured by X-ray diffractometry or calculated from X-ray diffractometry.

6. The pharmaceutically acceptable salt of claim 1 having at least one diffraction angle 2θ (°) of 20.5±0.5 as measured by X-ray diffractometry or calculated from X-ray diffractometry.

7. The pharmaceutically acceptable salt of claim 1 having at least one diffraction angle 2θ (°) of 23±0.5 as measured by X-ray diffractometry or calculated from X-ray diffractometry.

8. The pharmaceutically acceptable salt of claim 1, wherein the crystal has a unit cell of the space group P $2_1$/n, having dimensions of a=about 12.4541 Å, b=about 9.5447 Å, c=about 14.4013 Å and α=about 90°, β=about 100.5°, γ=about 90° and/or a cell volume of about 1683 Å$^3$ as measured by X-ray diffractometry.

9. The pharmaceutically acceptable salt of claim 1 in the form of plate-like crystals.

10. The pharmaceutically acceptable salt of claim 1 having a loss of weight from 31° C. to 140° C. of less than 1% as measured by thermal gravimetric analysis.

11. The pharmaceutically acceptable salt of claim 1 having at least one peak at 2941±1 cm−1 as measured by Raman spectroscopy.

12. The pharmaceutically acceptable salt of claim 1 having at least one peak at 1653±1 cm−1 as measured by Raman spectroscopy.

13. The pharmaceutically acceptable salt of claim 1 having at least one peak at 997±1 cm−1 as measured by Raman spectroscopy.

14. A composition comprising a pharmaceutically acceptable salt of claim 1 which contains less than 10% by weight of amorphous compound and a pharmaceutically acceptable excipient.

15. A composition comprising a pharmaceutically acceptable salt of claim 1, wherein at least 80% of the fumarate salt of β-guanidinopropionic acid in said composition is a 2:1 salt.

16. The composition of claim 14, wherein said composition is substantially free of the 1:1 fumarate salt of β-guanidinopropionic acid.

17. A pharmaceutical composition in unit dosage form comprising a pharmaceutically acceptable salt of claim 1 and a pharmaceutically acceptable excipient.

18. A pharmaceutical composition comprising a pharmaceutically acceptable salt of claim 1 and a pharmaceutically acceptable excipient, wherein said pharmaceutical composition is formulated for intravenous infusion.

19. A method of treating cancer in a subject in need thereof, said method comprising administering an effective amount of a pharmaceutically acceptable salt of claim 1 to said subject.

20. The method of claim 19, wherein said cancer is metastatic cancer.

21. The method of claim 20, wherein said effective amount comprises an amount effective to suppress metastatic colonization of said cancer.

22. The method of claim 21, wherein said cancer is gastrointestinal cancer.

23. The method of claim 19, wherein said subject is identified to have, or to be at risk of having, metastatic cancer on the basis of the expression level of miR-483-5p and/or miR-551a is below a predetermined reference value or the expression level of CKB and/or SLC6a8 is above a predetermined reference value.

24. A method for treating metastatic cancer in a subject in need thereof, comprising injecting into the subject an aqueous composition comprising a pharmaceutically acceptable salt of claim 1 and a pharmaceutically acceptable excipient in an amount effective to suppress metastatic colonization of said cancer.

25. The method of claim 24, wherein said metastatic cancer is gastrointestinal cancer.

26. A method of treating cancer in a subject in need thereof comprising:
    (a) providing a subject identified to have, or to be at risk of having, metastatic cancer on the basis of the expression level of miR-483-5p and/or miR-551a is below a predetermined reference value or the expression level of CKB and/or SLC6a8 is above a predetermined reference value; and
    (b) administering to the subject an effective amount of a pharmaceutically acceptable salt of claim 1.

27. The method of claim 26, wherein said metastatic cancer is gastrointestinal cancer.

28. A method of producing a pharmaceutically acceptable 2:1 fumarate salt of β-guanidinopropionic acid, said method comprising combining β-guanidinopropionic acid wherein said method further comprises dissolving said 2:1 fumarate salt of β-guanidinopropionic acid in a solvent wherein said 2:1 fumarate salt of β-guanidinopropionic acid precipitates from said solvent and fumaric acid in an amount sufficient to produce a pharmaceutically acceptable 2:1 fumarate salt of β-guanidinopropionic acid.

\* \* \* \* \*

UNITED STATES PATENT AND TRADEMARK OFFICE
CERTIFICATE OF CORRECTION

| | | |
|---|---|---|
| PATENT NO. | : 9,884,813 B1 | Page 1 of 3 |
| APPLICATION NO. | : 15/449428 | |
| DATED | : February 6, 2018 | |
| INVENTOR(S) | : Eduardo J. Martinez et al. | |

It is certified that error appears in the above-identified patent and that said Letters Patent is hereby corrected as shown below:

In the Specification

Column 1, Line 40, replace "6-guanidinopropionic" with --β-guanidinopropionic--.

Column 3, Line 26, replace "a=about 90°, β3=about 100.5°" with --α=about 90°, β=about 100.5°--.

Column 9, Line 1, replace "the PXRD trace" with --the XRPD trace--;
    Line 3, replace "the PXRD trace" with --the XRPD trace--.

Column 11, Line 16, replace "lypohilization" with --lyophilization--;
    Line 18, replace "stiochiometry" with --stoichiometry--;
    Line 49, replace "about means±0.5" with --about means ±0.5--.

Column 13, Line 33, replace "agent with a excipient" with --agent with an excipient--.

Column 14, Line 27, replace "loweralkyl" with --lower alkyl--.

Column 15, Line 40, replace "orpolyoxyethylated" with --or polyoxyethylated--.

Column 16, Line 19, replace "refers a composition" with --refers to a composition--.

Column 21, in TABLE 9-continued, replace "MLN518 (Millenium)" with --MLN518 (Millennium)--.

Column 23, Line 22, replace "found to be crystalline" with --found to be crystalline.--.

Column 25, in TABLE 12-continued, replace "L-Latic Acid" with --L-Lactic Acid--.

Signed and Sealed this
Seventh Day of August, 2018

Andrei Iancu
*Director of the United States Patent and Trademark Office*

Column 30, Lines 55-61, replace

"
| Time (minutes) | A % | B % |
|---|---|---|
| 0 | 25 | 75 |
| 15.0 | 25 | 75 |
| 23.0 | 80 | 20 |
| 25.0 | 80 | 20 |
| 25.1 | 25 | 75 |
| 30.0 | 25 | 75 |
"

with

--
| Time (minutes) | A % | B % |
|---|---|---|
| 0 | 25 | 75 |
| 15.0 | 25 | 75 |
| 23.0 | 80 | 20 |
| 25.0 | 80 | 20 |
| 25.1 | 25 | 75 |
| 30.0 | 25 | 75 |
--.

Column 32, Line 55, in TABLE 17, replace "Hausner Ration" with --Hausner Ratio--.

Column 34, Line 44, replace "β-GPA HCl. β-GPA" with --β-GPA HCl, β-GPA--;
  Line 55, replace "Foursalts" with --Four salts--;
  Line 66, replace "of the salt. Indicating that" with --of the salt, indicating that--.

Column 35, Line 67, replace "(Pattern 7A)" with --(Pattern 7A).--.

Column 36, Line 58, in TABLE 24, replace "EtOH=ethano" with --EtOH=ethanol--;
  Line 61, replace "fourty-five" with --forty-five--.

Column 37, Line 47, replace "lyophilized sample" with --lyophilized sample.--.

Column 38, in TABLE 26, replace "The started turned yellow to brown in color upon heating" with --Started to turn yellow to brown in color upon heating--.

Column 40, Line 6, replace "a=12.4541(5) A" with --a=12.4541(5) Å--;
  Line 7, replace "b=9.5447(4) A" with --b=9.5447(4) Å--;
  Line 8, replace "c=14.4013(6) A" with --c=14.4013(6) Å--;
  Line 13, replace "O...NH" with --O•••NH--;
  Line 16, replace "O...NH" with --O•••OH--;
  Line 19, replace "O...NH" with --O•••NH--.

Column 41, Lines 27-28, replace "β-Guanidiopropionic" with --β-Guanidinopropionic--.

Column 42, Line 2, replace "compared those which" with --compared to those which--;
  Line 5, replace "will not be represent of performance" with --will not be representative of performance--;
  Line 25, replace "below in Error! Reference source was not found.2." with --Table 32--.

Column 43, Line 37, in TABLE 34, replace "Pusher Nozle" with --Pusher Nozzle--.

Column 44, Line 18, in TABLE 35, replace "et milled API" with --jet milled API--;
       Line 44, replace "however this most likely due" with --however this is most likely due--.

Column 45, Line 48, replace "set a 1:1" with --set at 1:1--.